US012680098B2

(12) United States Patent
Jaschinski et al.

(10) Patent No.: US 12,680,098 B2
(45) Date of Patent: Jul. 14, 2026

(54) MODIFIED ANTISENSE OLIGONUCLEOTIDE FOR INHIBITION OF FoxP3 EXPRESSION

(71) Applicant: Secarna Pharmaceuticals GmbH & Co. KG, Marburg (DE)

(72) Inventors: Frank Jaschinski, Puchheim (DE); Richard Klar, Munich (DE); Sven Michel, Bernried (DE); Julia Festag, Eggenfelden (DE)

(73) Assignee: Secarna Pharmaceuticals GmbH & Co. KG, Marburg (DE)

( * ) Notice: Subject to any disclaimer, the term of this patent is extended or adjusted under 35 U.S.C. 154(b) by 978 days.

(21) Appl. No.: 17/789,579

(22) PCT Filed: Dec. 30, 2020

(86) PCT No.: PCT/EP2020/088032
§ 371 (c)(1),
(2) Date: Jun. 28, 2022

(87) PCT Pub. No.: WO2021/136807
PCT Pub. Date: Jul. 8, 2021

(65) Prior Publication Data
US 2022/0372482 A1 Nov. 24, 2022

(30) Foreign Application Priority Data
Dec. 30, 2019 (EP) ..................................... 19220140

(51) Int. Cl.
*C12N 15/113* (2010.01)
*A61K 45/06* (2006.01)

(52) U.S. Cl.
CPC ............ *C12N 15/113* (2013.01); *A61K 45/06* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2320/31* (2013.01); *C12N 2320/35* (2013.01)

(58) Field of Classification Search
CPC .............. C12N 15/113; C12N 2310/11; C12N 2310/315; C12N 2310/321; C12N 2310/322; C12N 2310/3231; C12N 2320/31; C12N 2320/35; C12N 2310/3525; C12N 2310/3533; A61K 45/06; A61K 31/7088; A61K 48/005; A61P 31/00; A61P 35/00
See application file for complete search history.

(56) References Cited

U.S. PATENT DOCUMENTS

| | | | |
|---|---|---|---|
| 11,547,718 B2 * | 1/2023 | Revenko ............ | A61K 31/7125 |
| 2009/0214533 A1 * | 8/2009 | Clynes .................. | C07K 16/32 424/173.1 |

| | | | |
|---|---|---|---|
| 2015/0337310 A1 | 11/2015 | Walker et al. | |
| 2019/0284529 A1 | 9/2019 | Benson et al. | |
| 2019/0336520 A1 * | 11/2019 | Cabon .................. | A61K 31/713 |

FOREIGN PATENT DOCUMENTS

| | | |
|---|---|---|
| CN | 106929509 A | 7/2017 |
| CN | 112969799 A | 6/2021 |
| WO | 2013151490 A1 | 10/2013 |
| WO | 2014154843 A1 | 10/2014 |
| WO | 2017181026 A1 | 10/2017 |
| WO | 2019232425 A1 | 12/2019 |
| WO | 2020069044 A1 | 4/2020 |
| WO | 2020102558 A1 | 5/2020 |

OTHER PUBLICATIONS

Morse, M.A. et al. "Depleting regulatory T cells with arginine-rich, cell-penetrating, peptide-conjugated morpholino oligomer targeting FOXP3 inhibits regulatory T-cell function". Cancer Gene Therapy , vol. 19 (2012), pp. 30-37. (Year: 2012).*
Miguel, A. et al. "Silencing of Foxp3 enhances the antitumor efficacy of GM-CSF genetically modified tumor cell vaccine against B16 melanoma". OncoTargets and Therapy, vol. 10 (2017), pp. 503-514. (Year: 2017).*
Kurreck, J. et al. "Design of antisense oligonucleotides stabilized by locked nucleic acids". Nucleic Acids Research, vol. 30, No. 9 ( 2002), pp. 1911-1918. (Year: 2002).*
Bennett et al., "The immune dysregulation, polyendocrinopathy, enteropathy, X-linked syndrome (IPEX) is caused by mutations of FOXP3", Nature Genetics, vol. 27, Jan. 2001, p. 20-21.
Chemical Prevention and Drug Therapy of Cancer in the New Century / Edited by Han Rui and Sun Yan. Beijing: People's Military Medical Press, Jan. 2005, ISBN 7-80194-153-5 (see CN original & English translation of "non-patent literature 1").
Zhang et al., "Down-modulation of cancer targets using locked nucleic acid (LNA)-based antisense oligonucleotides without transfection", Gene Therapy, (2011), vol. 18, pp. 326-333.
Stanton et al., "Chemical Modification Study of Antisense Gapmers", Nucleic Acid Therapeutics, vol. 22, No. 5, 2012, pp. 344-359.

(Continued)

*Primary Examiner* — Nancy J Leith
*Assistant Examiner* — Alexandra Geraldine Dace Denito
(74) *Attorney, Agent, or Firm* — Adams & Reese, LLP

(57) ABSTRACT

The present invention refers to an oligonucleotide comprising 12 to 25 nucleotides, wherein at least one of the nucleotides comprises a modification selected from the group consisting of a bridged nucleic acid such as LNA, ENA, a 2'Fluoro modified nucleotide, a 2 O-Methyl modified nucleotide, a 2 O-Methoxy modified nucleotide, a FANA and a combination thereof. The oligonucleotide hybridizes with a nucleic acid sequence of Foxp3 of SEQ ID NO. 1 and/or of SEQ ID NO. 2 resulting in a reduction of the expression of FoxP3 mRNA, FoxP3 pre-mRNA or a combination thereof. The invention is further directed to a pharmaceutical composition comprising an oligonucleotide of the present invention and to the oligonucleotide and pharmaceutical composition, respectively for use in a method of preventing and/or treating a disorder, where FoxP3 imbalance is involved.

14 Claims, 20 Drawing Sheets
Specification includes a Sequence Listing.

(56) References Cited

OTHER PUBLICATIONS

Sinclair et al., Discovery and characterization of AZD8701, a high affinity antisense oligonucleotide targeting FOXP3 to relieve immunosuppression in cancer [abstract]. In: Proceedings of the American Association for Cancer Research Annual Meeting 2019; (2019) 79 (13_Supplement), Abstract nr 2713, 4 pages.

Sinclair, Charles, Biosis Database, Accession No. PREV201900948488, doi:10.1158/1538-7445. AM2019-2713, XP-002799345, Retrieved from: cancerres.aacrjournals.org [retrieved on Jul. 2019] 1 page.

Ma Morse et al., "Depleting regulatory T cells with arginine-rich, cell-penetrating, peptide-conjugated morpholino oligomer targeting FOXP3 inhibits regulatory T-cell function", Cancer Gene Therapy (2012), 19, p. 30-37.

C. Veldman et al., "Inhibition of the Transcription Factor Foxp3 Converts Desmoglein 3-Specific Type 1 Regulatory T Cells into Th2-Like Cells", J. Immunol 2006; 173:3215-3222.

* cited by examiner

Fig. 1A: First screening round of human FoxP3-specific ASOs in CD4+ T cells of donor 1

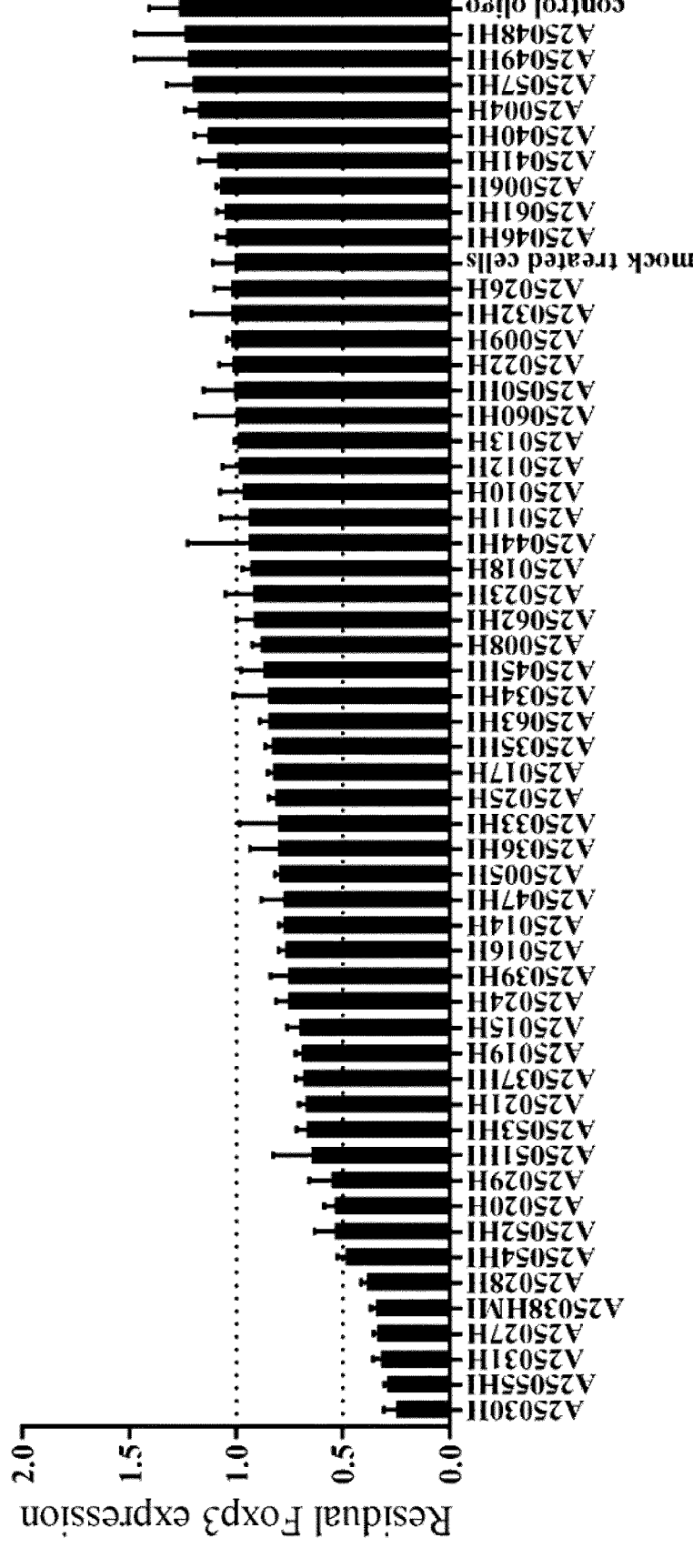
Fig. 1B: First screening round of human FoxP3-specific ASOs in CD4+ T cells of donor 2

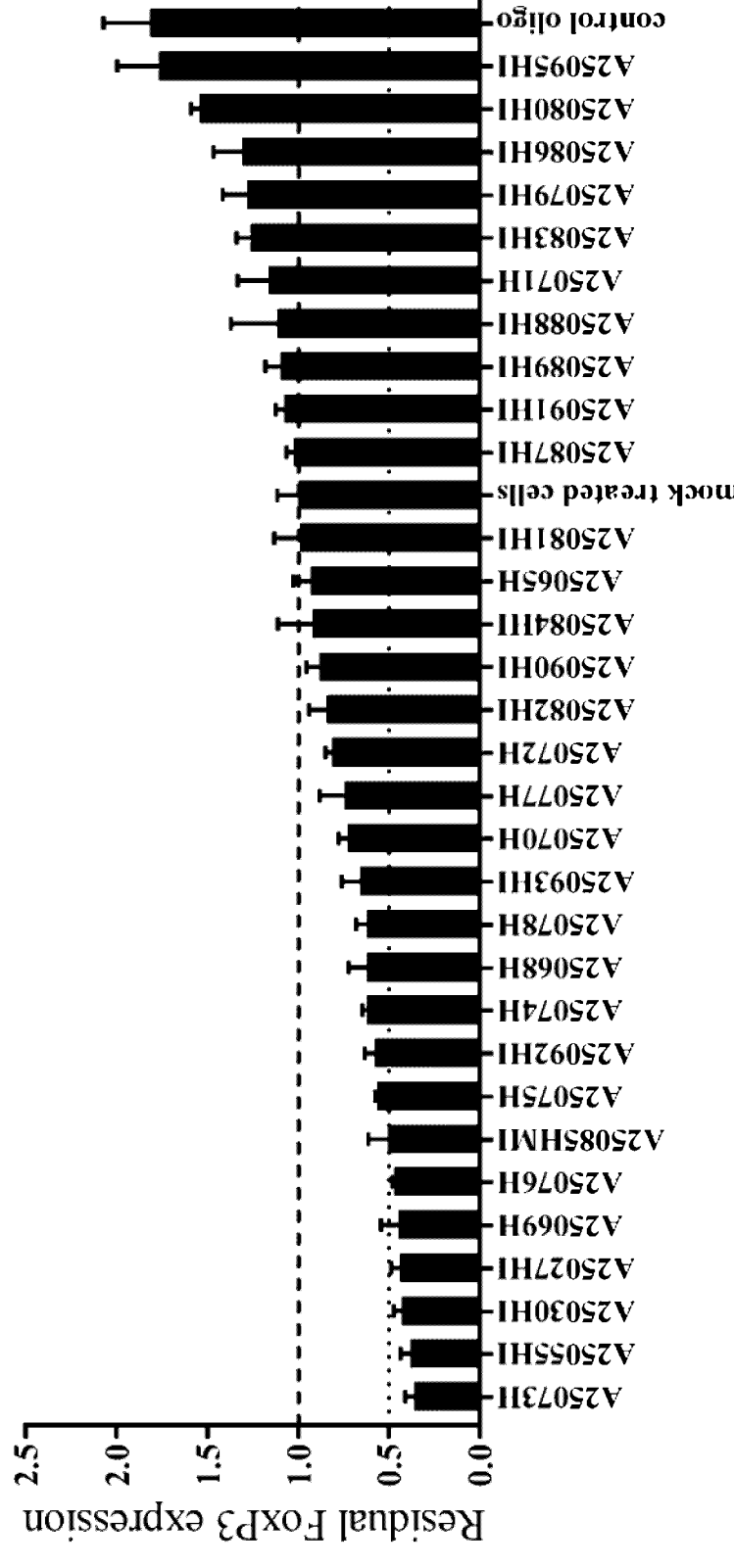
Fig. 2A: Second screening round of human FoxP3-specific ASOs in CD4+ T cells of donor 1

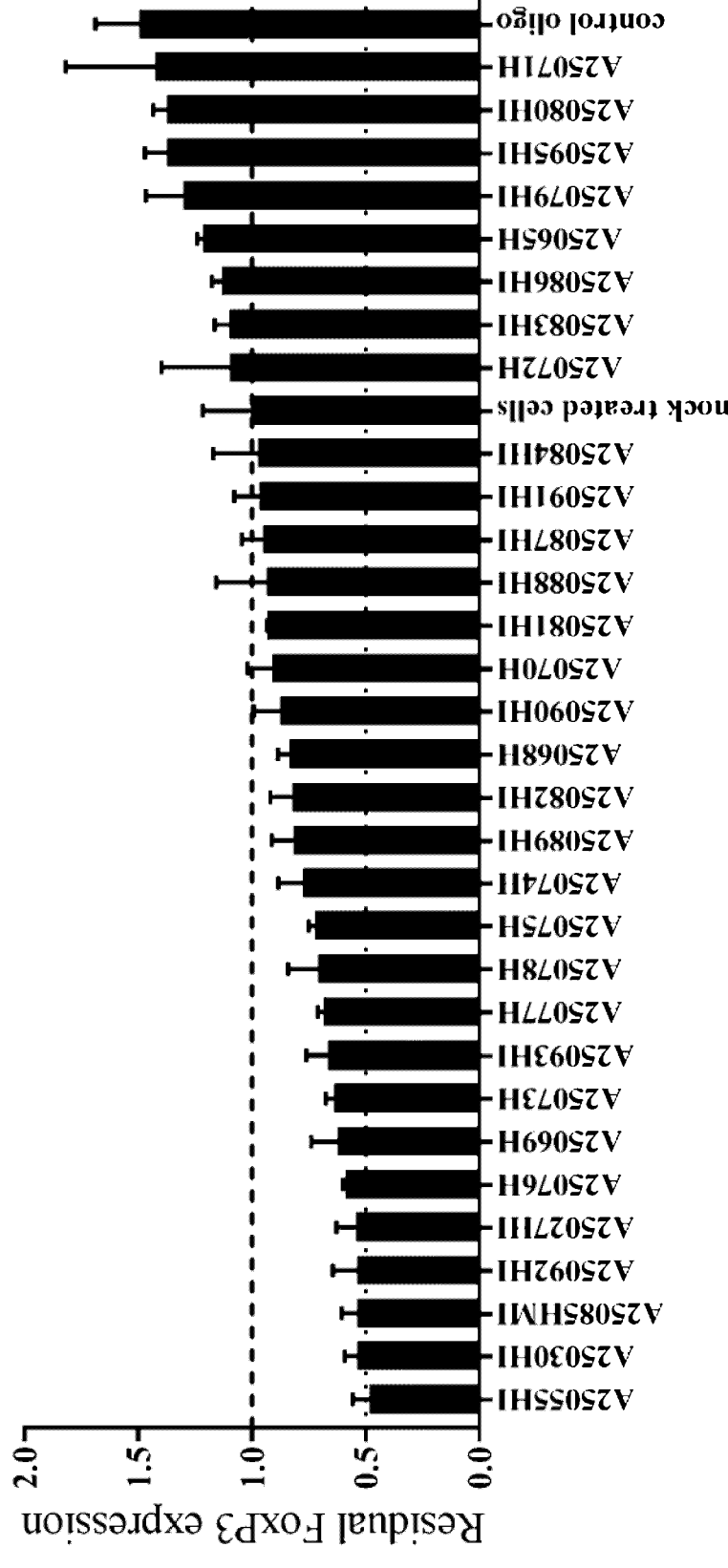
Fig. 2B: Second screening round of human FoxP3-specific ASOs in CD4+ T cells of donor 2

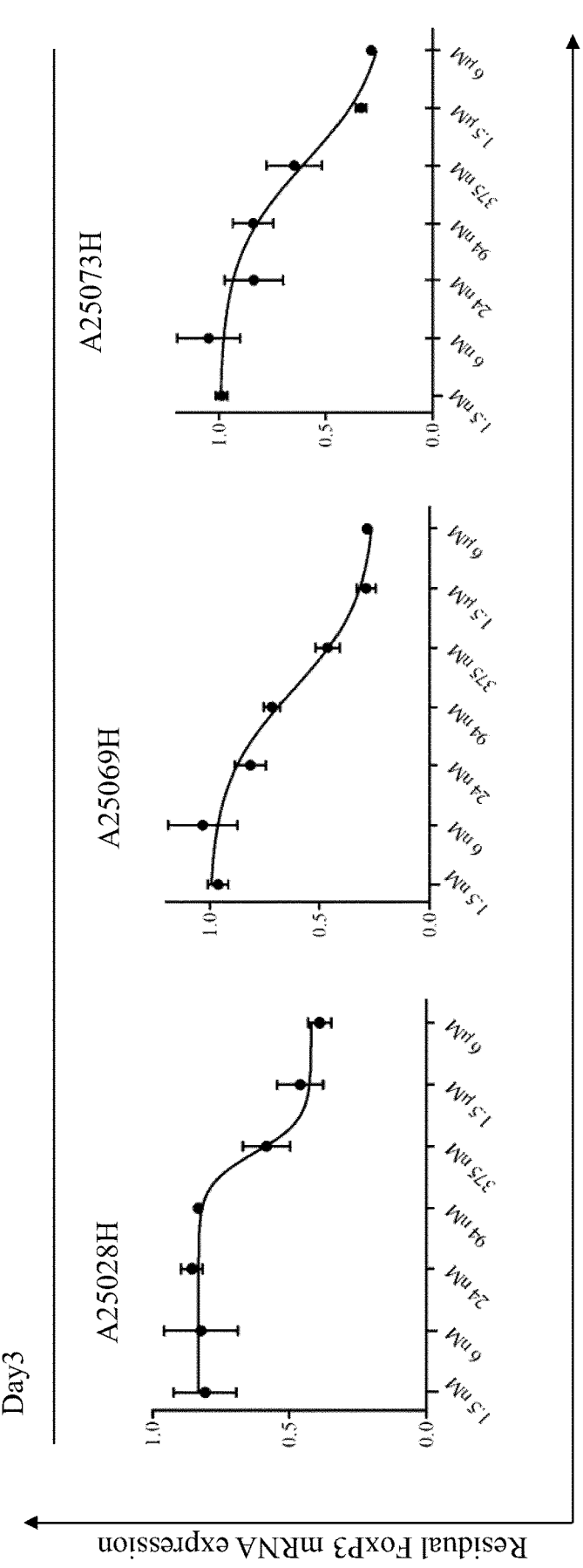
Fig. 3: Dose-dependent FoxP3 mRNA knockdown by selected FoxP3 ASOs in regulatory T cells after 3, 7 and 9 days Fig. 3: Dose-dependent FoxP3 mRNA knockdown by selected FoxP3 ASOs in regulatory T cells after 3, 7 and 9 days (continued)
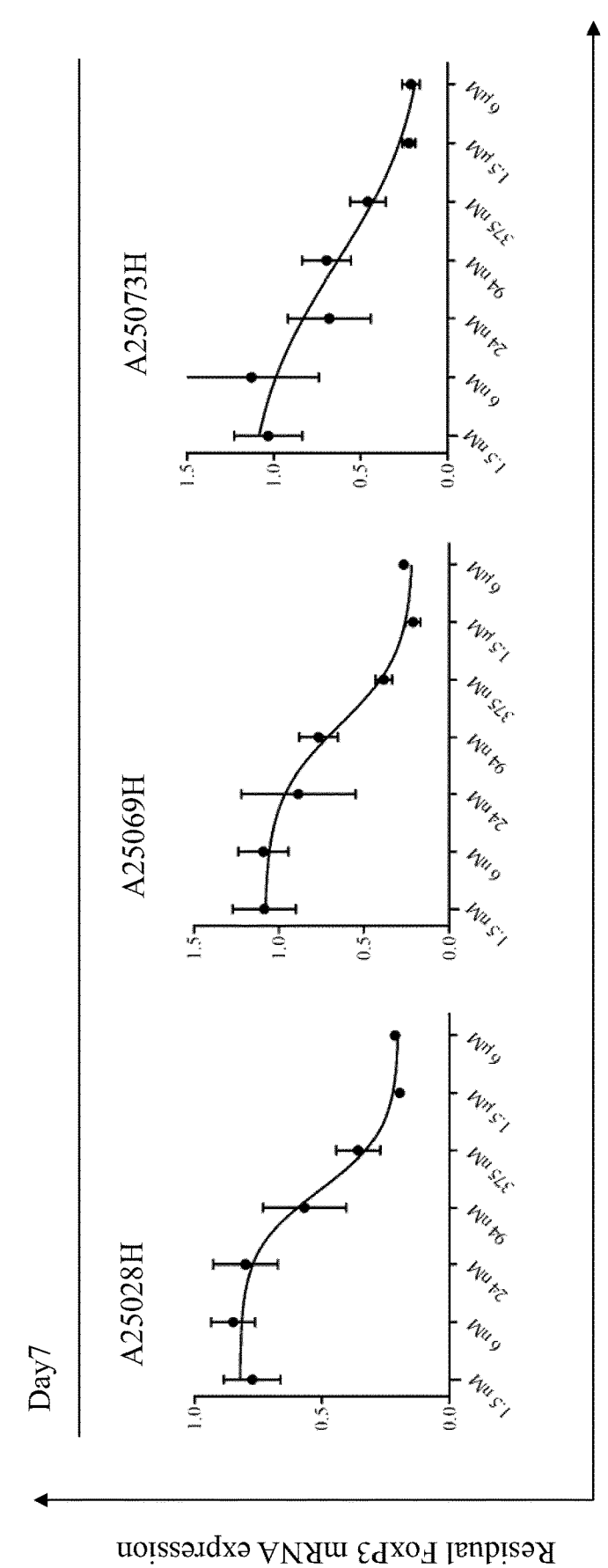

Fig. 3: Dose-dependent FoxP3 mRNA knockdown by selected FoxP3 ASOs in regulatory T cells after 3, 7 and 9 days (continued)
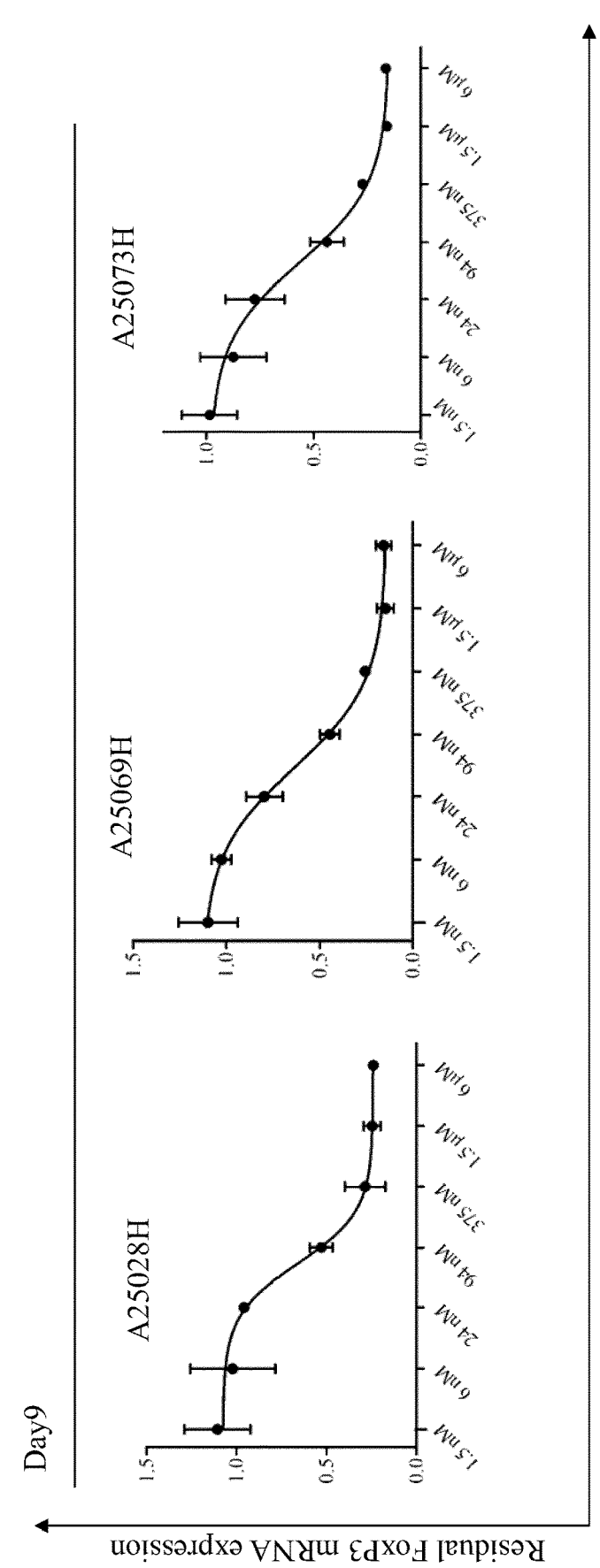

Fig. 4A: Effect of FoxP3 knockdown in natural T$_{regs}$ on their suppressive capacity
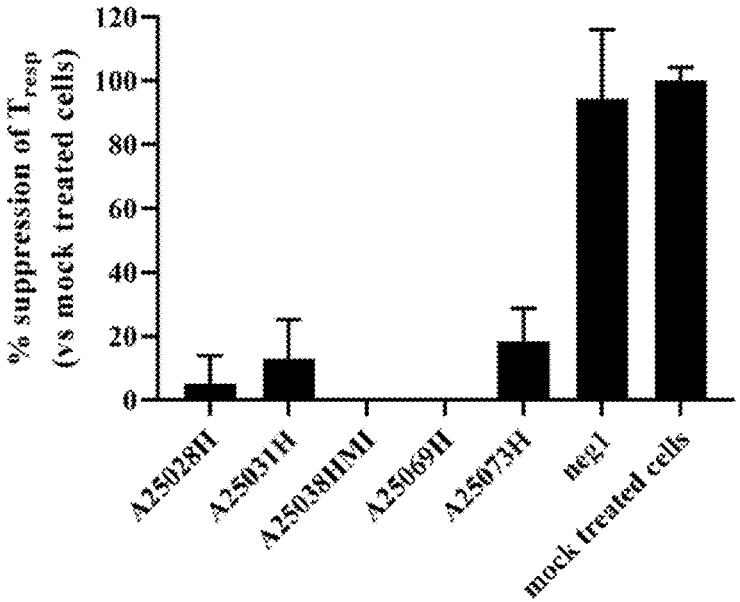

Fig. 4B: Effect of FoxP3 knockdown in natural T$_{regs}$ on their suppressive capacity
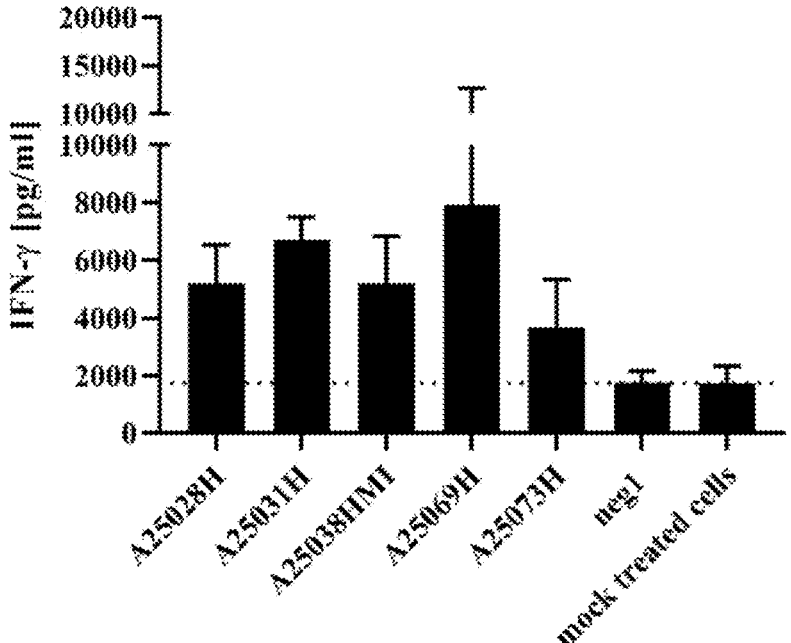

Fig. 4C: Effect of FoxP3 knockdown in natural T$_{regs}$ on their suppressive capacity
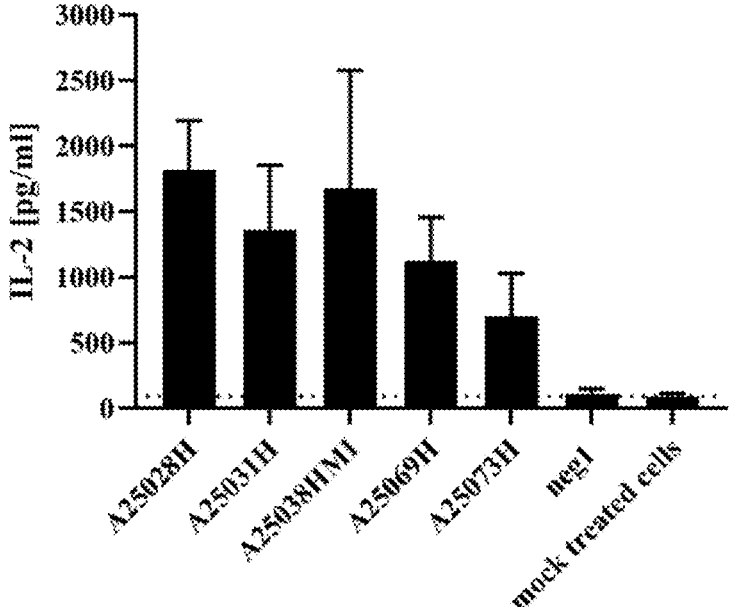

Fig. 5A: Target knockdown efficacy screening of mouse FoxP3-specific ASOs in CD4⁺ T cells of donor mouse 1

Fig. 5B: Target knockdown efficacy screening of mouse FoxP3-specific ASOs in CD4+ T cells of donor mouse 2
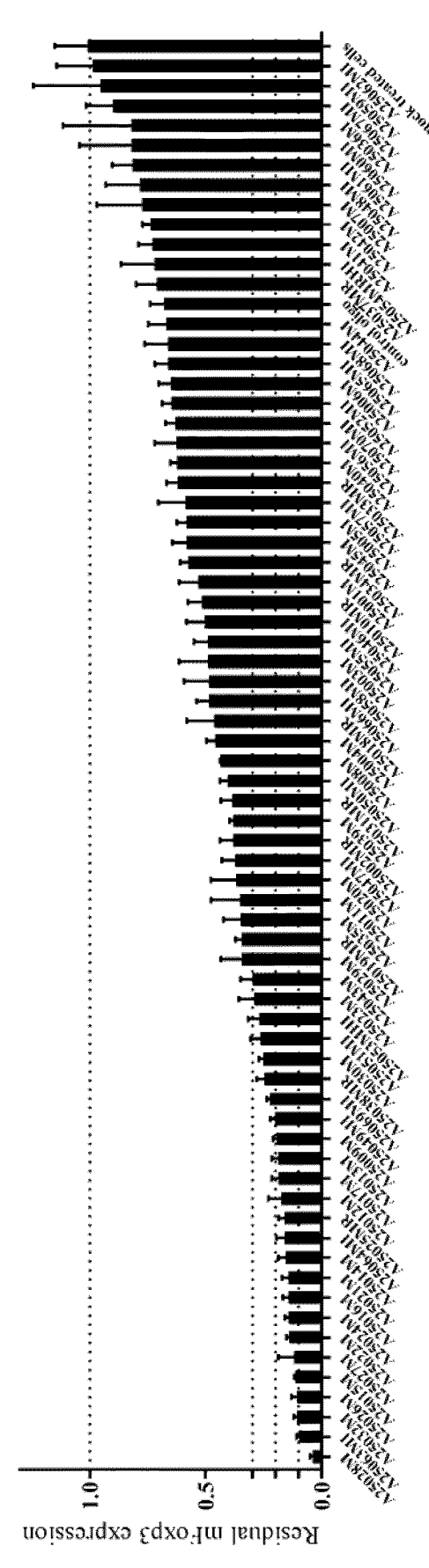

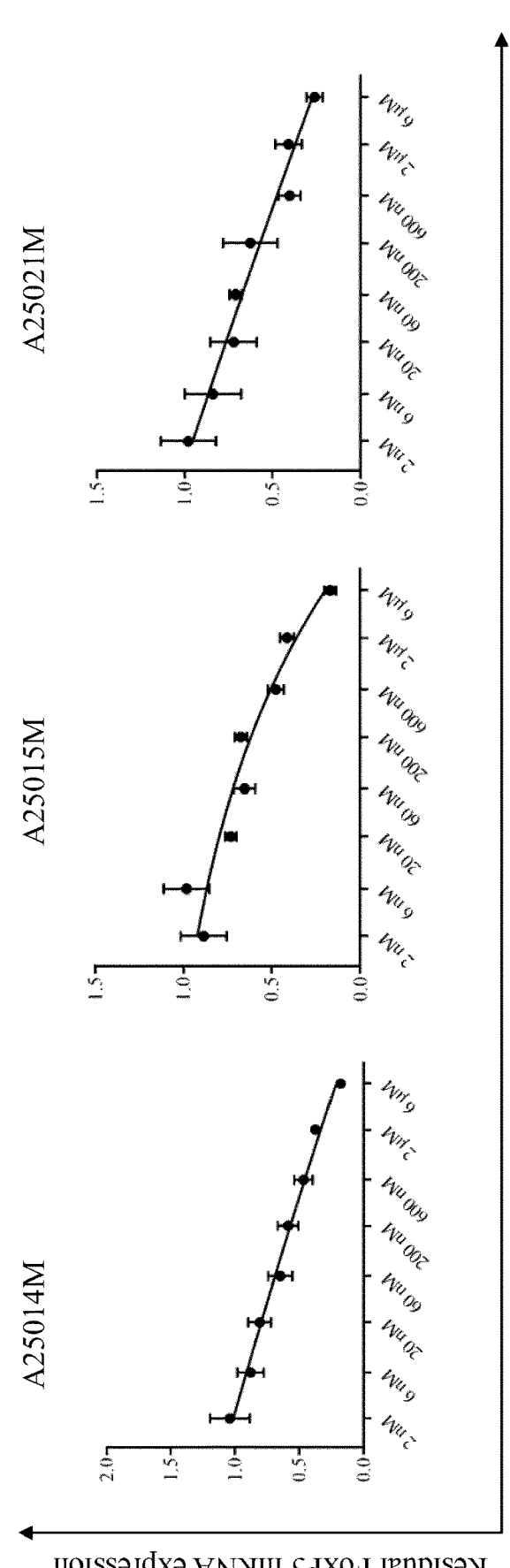
Fig. 6: Dose-dependent FoxP3 mRNA knockdown by selected FoxP3 ASOs in CD4+ T cells

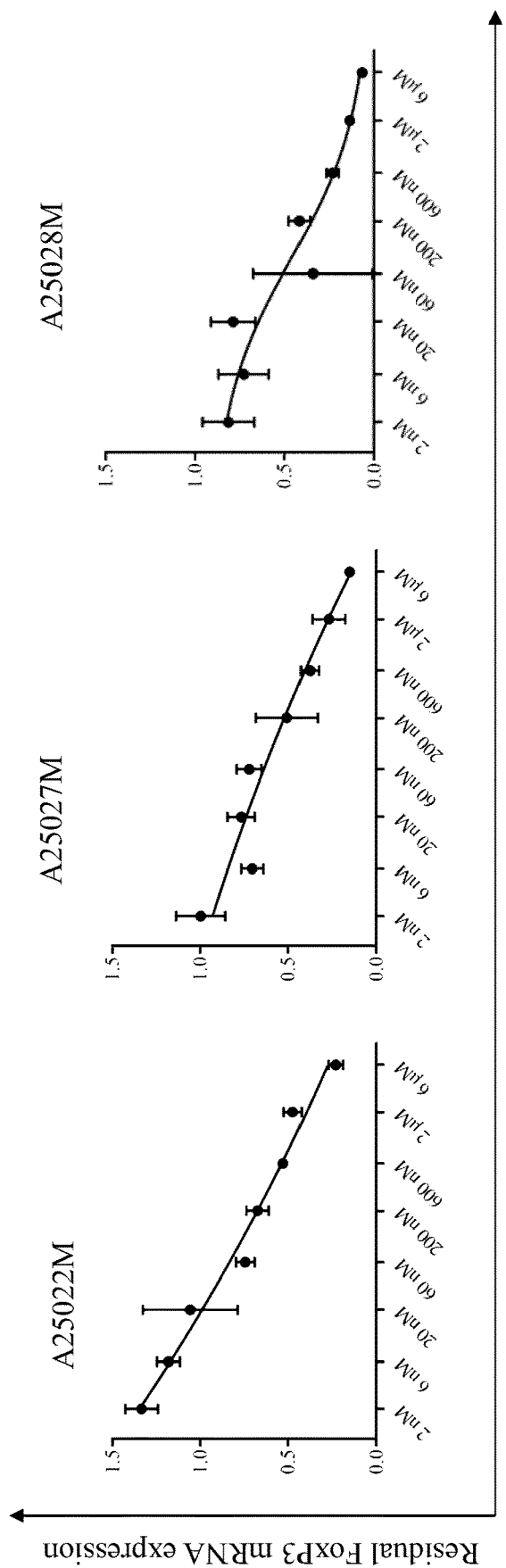
Fig. 6: Dose-dependent FoxP3 mRNA knockdown by selected FoxP3 ASOs in CD4+ T cells (continued)

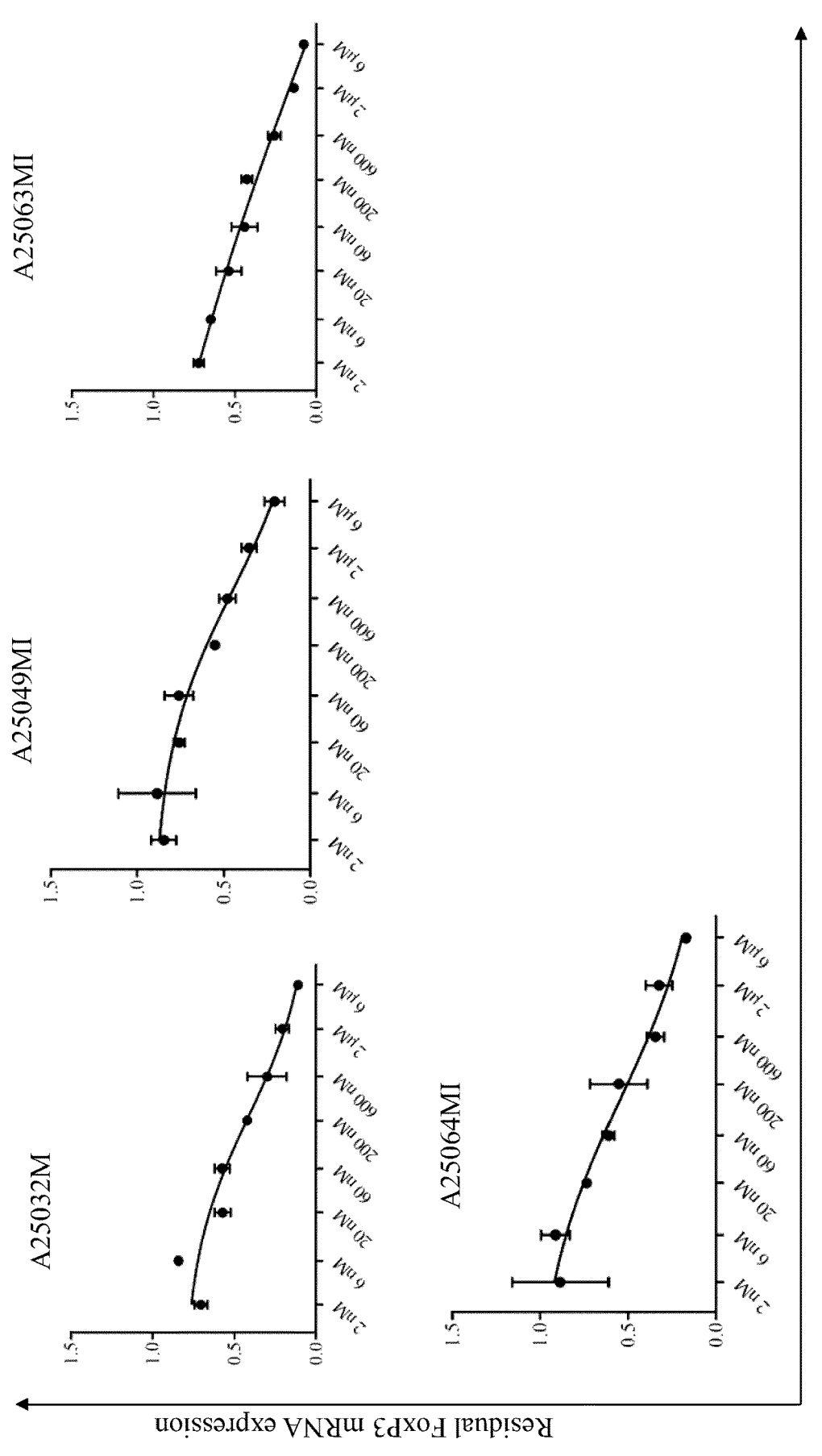
Fig. 6: Dose-dependent FoxP3 mRNA knockdown by selected FoxP3 ASOs in CD4+ T cells (continued)

Fig. 7A and 7B: Effect of FoxP3 knockdown in natural T$_{regs}$ on their suppressive capacity
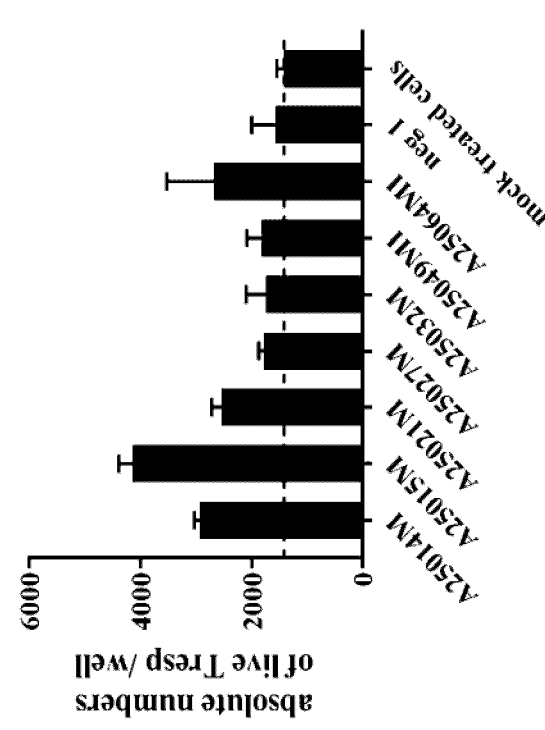
B)
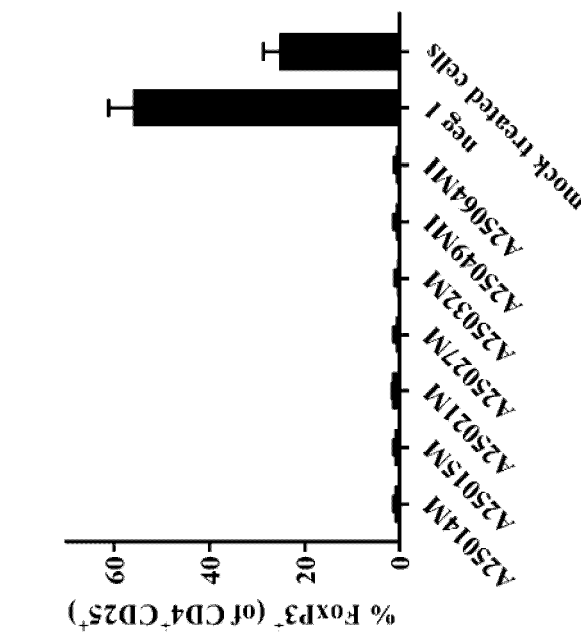
A)

Figure 8A: Third screening round of human FoxP3-specific ASOs in CD4+ T cells of donor 1

Figure 8B: Third screening round of human FoxP3-specific ASOs in CD4⁺ T cells of donor 2
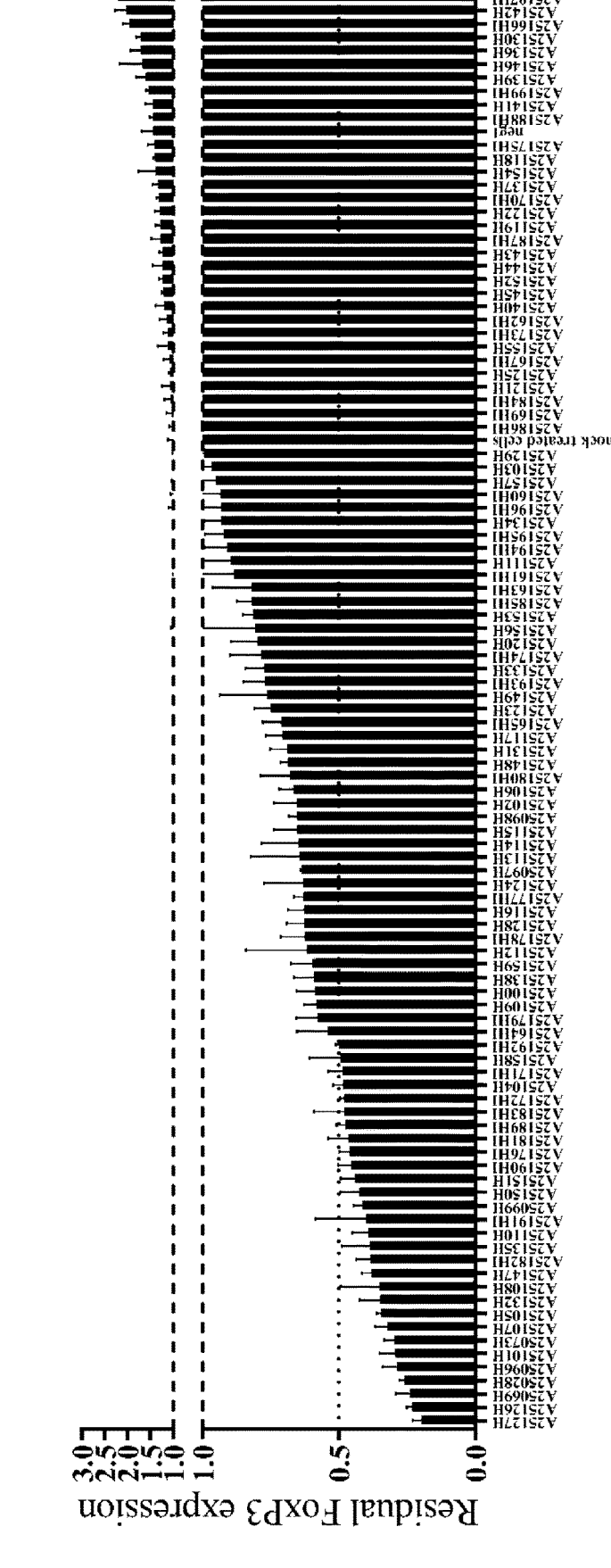

Fig. 9: Dose-dependent FoxP3 mRNA knockdown by selected FoxP3 ASOs in regulatory T cells after 3 days ASO treatment
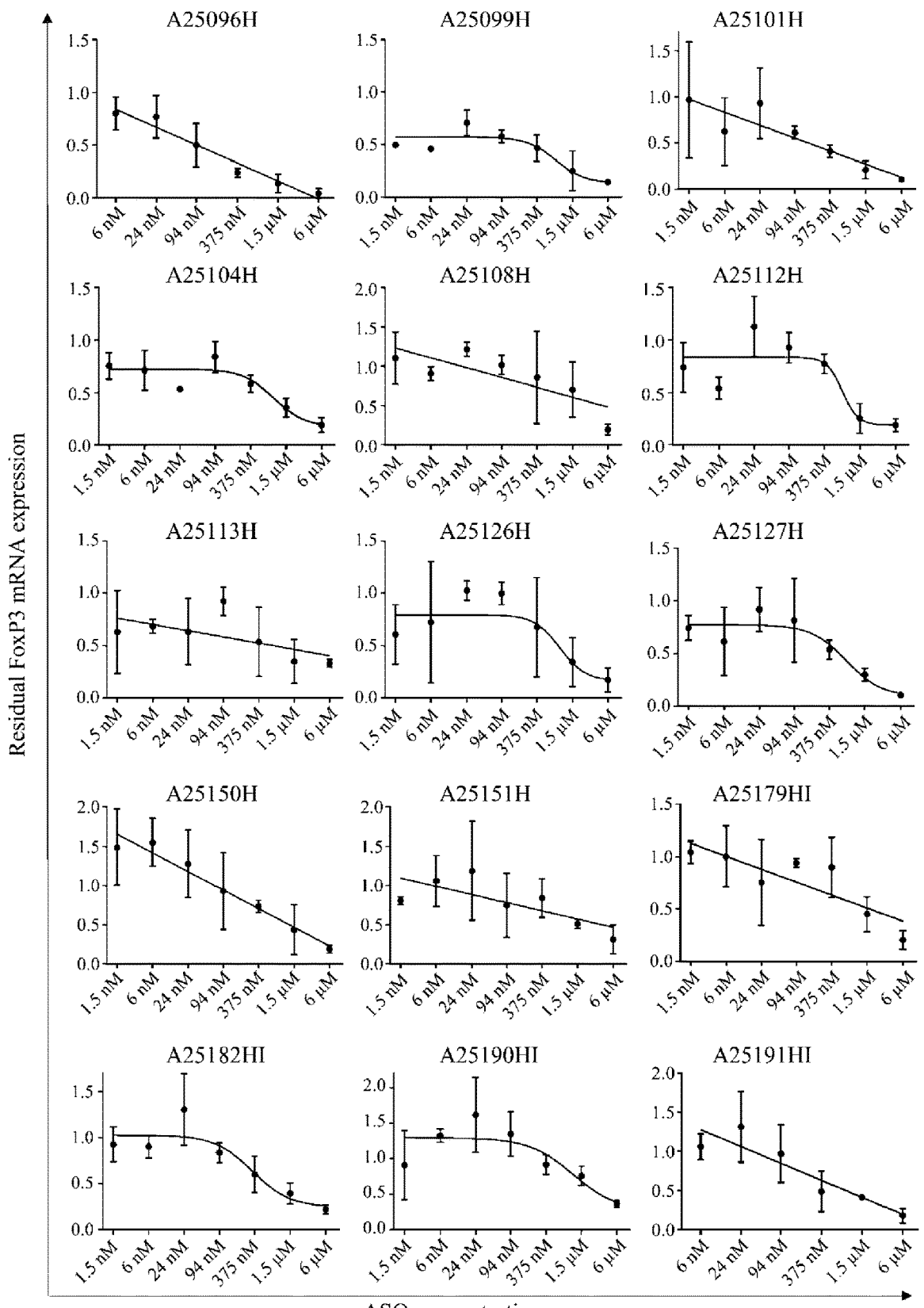

Fig. 10: Dose-dependent FoxP3 mRNA knockdown by selected FoxP3 ASOs in regulatory T cells after 3, 6 and 10 days
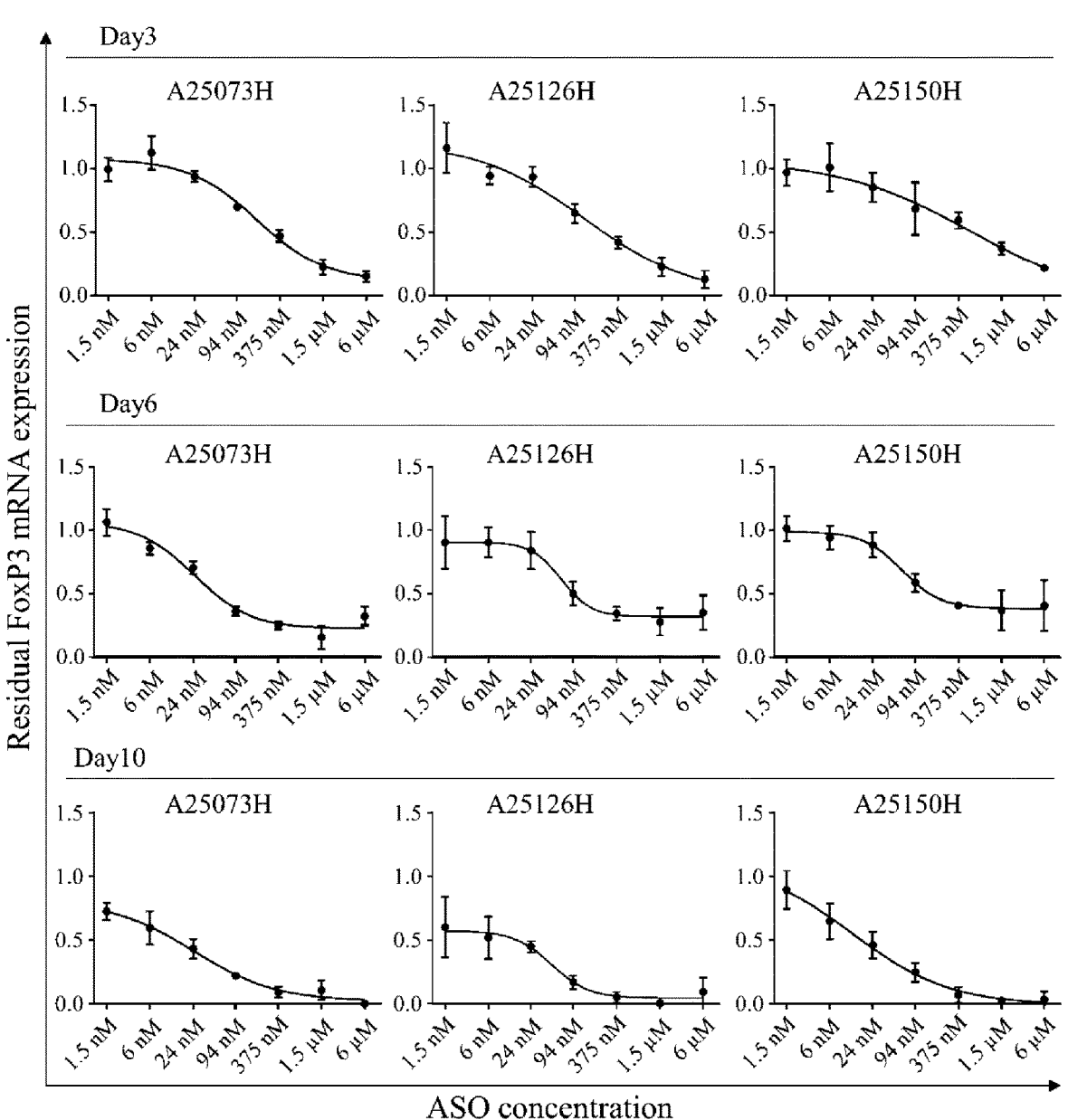

MODIFIED ANTISENSE OLIGONUCLEOTIDE FOR INHIBITION OF FoxP3 EXPRESSION

The present invention refers to an oligonucleotide such as an antisense oligonucleotide hybridizing with a nucleic acid sequence of FoxP3 for inhibiting the expression of FoxP3 as well as to a pharmaceutical composition comprising such antisense oligonucleotide, wherein the antisense oligonucleotide and the pharmaceutical composition, respectively, are used in a method of preventing and/or treating a disorder where FoxP3 imbalance is involved.

TECHNICAL BACKGROUND

FoxP3 (forkhead box P3), also known as scurfin, is a protein involved in immune system responses. It is a member of the FOX protein family. FOX proteins belong to the forkhead/winged-helix family of transcriptional regulators. FoxP3 functions as a master regulator of the regulatory pathway in the development and function of regulatory T cells ($T_{regs}$). $T_{regs}$ generally turn the immune response down. In cancer, $T_{reg}$ functionality can prevent the immune system from destroying cancer cells. In infectious diseases, $T_{reg}$ functionality can prevent the immune system from fighting the disease and in vaccination approaches, $T_{reg}$ activity can prevent successful induction of vaccine-induced immune responses.

Foxp3 is a specific marker of natural $T_{regs}$ ($nT_{regs}$, a lineage of T cells) and adaptive/induced $T_{regs}$ ($a/iT_{regs}$), also identified by other less specific markers such as CD25 or CD45RB. FoxP3 is a $T_{reg}$ specific transcription factor which regulates different genes. On the one hand FoxP3 inhibits the expression of pro-inflammatory genes such as interleukin-2 (IL2) and/or interferon gamma (IFNγ), on the other hand FoxP3 induces genes such as CD25, Ctla4, Tnfrsf18 which contribute to the suppressive activities of $T_{regs}$ (Xie X. et al., Plos Genetics, 2015). $T_{regs}$ play an important role in the suppression of the immune response in the micro milieu of a tumor (Tanaka A. et al., Cell Research, 2017). The capacity of $T_{regs}$ to suppress antitumor responses is reduced by reduction/inhibition of FoxP3 expression as the suppression of pro-inflammatory genes as well as the induction of suppressive genes is reduced.

FoxP3 is a transcription factor acting within the nucleus of $T_{regs}$. Therefore, antisense oligonucleotides (ASOs) are the ideal way to target FoxP3, as antibodies are not able to bind intracellular targets and small molecules are ineffective in preventing activity of transcription factors. Accordingly, an agent which is safe and effective in inhibiting the function of the transcription factor FoxP3 represents a promising strategy for treatment of patients suffering from diseases or conditions affected by high numbers of immunosuppressive $T_{regs}$.

$T_{regs}$ are one major subtype of immunosuppressive immune cells within the tumor microenvironment. They account for 10-50% of $CD4^+$ T cell in tumors compared to 2-5% of $CD4^+$ T cells in peripheral blood of individuals without cancer. Infiltration of $T_{regs}$ into tumors are associated with poor prognosis in patients with divers types of cancer, e.g. melanoma, non-small cell lung, ovarian and gastric cancers (Togashi Y et al, Nat Rev Clin Oncol, 2019). $T_{regs}$ inhibit effector T cells in their function to recognize and eliminate tumor cells. Locked-nucleic acid (LNA) modified ASOs that inhibit expression of FoxP3 and therefore impair $T_{regs}$ in their immunosuppressive function represent a promising possibility to give rise to highly functional effector T cells that are able to eliminate tumor cells.

Enhanced numbers of $T_{regs}$ with their immune suppressive capacity have also been reported for chronic viral infections, e.g. chronic hepatitis B and C virus infections (Jung M K et al, Immune Netw, 2016). $T_{regs}$ hereby also promote progression to hepatitis-related liver diseases like hepatocellular carcinoma (Li W et al, Chronic Dis Transl Med, 2016). Therefore, $T_{regs}$ represent a potential target for treating e.g. patients with chronic hepatitis B virus infections (Yang J et al, Cell Mol Immunol, 2017). The detrimental role of $T_{regs}$ is also described for e.g. human immunodeficiency virus (HIV) (Kleinman A J et al, Front Immunol, 2018), cytomegalovirus (CMV) (Aandahl E M et al, J Virol, 2004), Herpes Simplex virus and respiratory syncytial virus infections (Veiga-Parga T et al, Immunol Rev, 2013). Hereby, $T_{regs}$ reduce the magnitude of the protective T cell response, display an inhibitory effect on antiviral cytokine production produced by effector cells and exhibit an inhibitory effect on cell trafficking of protective T cells to the site of infection (Veiga-Parga T et al, Immunol Rev, 2013).

The efficacy of therapeutic vaccinations could be enhanced by a combination with FoxP3-specific ASOs as the balance of T-effectors/$T_{regs}$ could be shifted towards effectors to improve vaccine-specific immune-responses, e.g. for therapeutic HIV-1 vaccines, (Hubert A et al, Hum Vaccin Immunother, 2018), numerous cancer such as metastatic breast cancer (Reach A J et al, Sci Trans Med, 2012), chronic retroviral infection (Knuschke T et al., Retrovirology, 2016), chronic HBV infection or persistent *Helicobacter pylori* infections.

So far cET and FANA-modified antisense oligonucleotides and CD25 antibodies have been prepared, however, their activity appears to be improvable. Hence, there is a need for compounds such as an oligonucleotide, e.g., an antisense oligonucleotide, having improved activity with regard to inhibition of FoxP3 expression. It is known from the literature, that for example cET-modified antisense oligonucleotides need to be administered in vivo over three weeks at 80 mg/kg per week to achieve a target knockdown of about 50% (DOI: 10.1126/scitranslmed.aal5253) or over three weeks at 250 mg/kg per week to achieve a target knockdown of about 50% (doi: 10.1126/scitranslmed.aac5272).

Therefore, FoxP3 ASOs have been investigated having higher activity with regard to target knockdown compared to compounds of the prior art, leading to potent target knockdown at a lower dose of the compound and preferably resulting in target knockdown at an earlier time point. Reduced doses inhibit for example the appearance of class-specific toxicity. In addition or alternatively, use of FoxP3-specific antisense oligonucleotides instead of an anti-CD25 antibody avoids the depletion of activated CD25-expressing T-cells during administration.

A solution to this problem is provided by the oligonucleotides such as antisense oligonucleotides of the present invention which inhibit the expression of FoxP3 very potently and efficiently.

An antisense oligonucleotide of the present invention is very successful in the inhibition of the expression of FoxP3. The mode of action of an antisense oligonucleotide differs from the mode of action of an antibody or small molecule, and antisense oligonucleotides are highly advantageous regarding for example (i) the penetration of tumor tissue in solid tumors, (ii) the blocking of multiple functions, activities and downstream effects, respectively, of a target, (iii) the combination of antisense oligonucleotides with each other or an antibody or a small molecule, and (iv) the inhibition of intracellular effects which are not accessible for an antibody or inhibitable via a small molecule.

SUMMARY

The present invention refers to an oligonucleotide comprising 12 to 25 nucleotides, wherein at least one of the nucleotides comprises a modification selected from the group consisting of a bridged nucleic acid such as LNA (locked nucleic acid), ENA (2'-O,4'-C-ethylene-bridged nucleic acid), a 2'Fluoro modified nucleotide, a 2 O-Methyl modified nucleotide, a 2 O-Methoxy modified nucleotide, a FANA (2'-deoxy-2-fluoro-D-arabinonucleic acid) and a combination thereof, and hybridizing with a nucleic acid sequence of Foxp3 of SEQ ID NO. 1 and/or of SEQ ID NO. 2 resulting in a reduction of FoxP3, FoxP3 mRNA, FoxP3 pre-mRNA or a combination thereof of 40% to 99% within 6 to 240 h or within 12 to 120 h from first administration of the oligonucleotide compared to an untreated control.

The oligonucleotide of the present invention reduces for example FoxP3, FoxP3 mRNA, FoxP3 pre-mRNA or a combination thereof of 40% to 99% within 24 to 72 h from first administration of the oligonucleotide.

The oligonucleotide of the present invention hybridizes for example with Foxp3 of SEQ ID NO. 1 and/or SEQ ID NO. 2, wherein the oligonucleotide is for example selected from one of SEQ ID NO. 3 to SEQ ID NO. 322 hybridizes for example within a region of position 1510 to 2109 of SEQ ID NO. 2. The oligonucleotide hybridizes for example within a region of position 1510 to 2109 of SEQ ID NO. 2. The oligonucleotide inhibits the expression of FoxP3, FoxP3 mRNA, FoxP3 pre-mRNA or a combination for example at a nanomolar or micromolar concentration.

The present invention further refers to a pharmaceutical composition comprising an oligonucleotide of the present invention and a pharmaceutically acceptable carrier, excipient, diluent or a combination thereof. The pharmaceutical composition further comprises optionally an antitumor active agent such as a chemotherapeutic (e.g., platinum, gemcitabine), an immune stimulating agent, disease specific agent or an agent that reverses tumor- or infection-mediated immunosuppression, another oligonucleotide, an antibody, a carbohydrate-modified antibody, a peptide-based therapeutic, a protein-based therapeutic, a therapeutic vaccine, a HERA fusion protein, a ligand trap, a Fab fragment, a nanobody, a BiTe® (bispecific T-cell engager), a DARPin® (Designed Ankyrin Repeat Proteins), a small molecule or a combination thereof. The antitumor active agent, the disease specific agent, the other oligonucleotide, the antibody, the carbohydrate-modified antibody, the peptide-based therapeutic, the protein-based therapeutic, the therapeutic vaccine, the HERA fusion protein, the ligand trap, the Fab fragment, the nanobody, the BiTe®, the DARPin® and/or the small molecule comprised by the pharmaceutical composition inhibits for example expression or activity of an immune suppressive factor selected from the group consisting of IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, MTDH, Xbp1, Chop and a combination thereof, or stimulates expression or activity of an immune stimulatory factor selected from the group consisting of 4-1BB, Ox40, KIR, GITR, CD27, 2B4 and a combination thereof.

The disease specific agent, the other oligonucleotide, the antibody, the carbohydrate-modified antibody, the peptide-based therapeutic, the protein-based therapeutic, the therapeutic vaccine, the HERA fusion protein, the ligand trap, the Fab fragment, the nanobody, the BiTe®, the DARPin® and/or the small molecule comprised by the pharmaceutical composition inhibits for example expression or activity of a factor involved in cancer progression and/or metastasis selected from the group consisting of SND1, HER-2, BRAF, KRAS, VEGF, EGFR1, EGFR2, BCR/ABL, ABL, MET, ALK, JAK2, BTK, miR-223, CCL18, CCL20, Lcn2, CCL5/CCR9, DDR2, PHD2, IL6, SDF-1/CXCL12 and a combination thereof.

The oligonucleotide and/or the pharmaceutical composition of the present invention are for example for use in a method of preventing and/or treating a disorder, where an imbalance of FoxP3, FoxP3 mRNA, FoxP3 pre-mRNA or a combination is involved. The disorder is for example a malignant and/or benign tumor, a chronic infectious disease, a chronic inflammatory disease caused by infection or a combination thereof.

The malignant tumor is for example selected from the group consisting of breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomata tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythemia vera, adenocarcinoma, anaplastic astrocytoma, glioblastoma multiforme, leukemia, epidermoid carcinoma and a combination thereof.

The chronic infectious disease is for example selected from the group consisting of hepatitis B and/or C virus, human immune deficiency virus, cytomegalovirus, Herpes Simplex virus, Measles virus, respiratory syncytial virus, *Helicobacter pylori* infection or a combination thereof. The chronic inflammatory disease caused by infection is for example selected from the group consisting of chronic inflammatory diseases of the liver such as liver fibrosis, liver cirrhosis or a combination thereof.

The oligonucleotide and/or the pharmaceutical composition of the present invention is for example suitable to be administered locally or systemically.

The oligonucleotide of the present invention is for example an antisense oligonucleotide.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

DESCRIPTION OF FIGURES

FIGS. 1A and 1B depict a first screening round of human FoxP3-specific antisense oligonucleotides (ASOs) in CD4$^+$ T cells of donor 1 (FIG. 1A) and donor 2 (FIG. 1B). CD4$^+$ T cells were treated with human Foxp3-specific antisense oligonucleotides of the present invention at a concentration of 5 μM for three days without the addition of a transfection reagent. FoxP3 and HPRT1 mRNA expression was analyzed using the QuantiGene® (RNA Assays for Gene Expression Profiling) Singleplex assay (ThermoFisher) and the FoxP3 expression values were normalized to HPRT1 values.

FIGS. 2A and 2B show the second screening round of human FoxP3-specific ASOs in CD4$^+$ T cells of donor 1 (FIG. 2A) and donor 2 (FIG. 2B). Treatment with all tested ASOs from the first screening round and A25073H (SEQ ID NO. 58), A25069H (SEQ ID NO. 56) and A25076H (SEQ ID NO. 26) from the second screening round resulted in a target inhibition of >50% (FIG. 2A). All tested ASOs from the first screening round and A25085HMI (SEQ ID NO. 66), A25092HI (SEQ ID NO. 73) and A25076H (SEQ ID NO. 26) from the second screening round resulted in a target inhibition of >40% (FIG. 2B).

FIG. 3 shows dose-dependent FoxP3 mRNA knockdown by selected FoxP3 ASOs in regulatory T cells after 3, 7 and 9 days. T$_{regs}$ were treated for three, seven or nine days with human antisense oligonucleotides of the present invention in concentrations of 6 μM, 1.5 μM, 375 nM, 94 nM, 24 nM, 6 nM, and 1.5 nM.

FIG. 4A to 4C depicts the effect of FoxP3 knockdown in natural T$_{regs}$ on their suppressive capacity, shown as % suppression of T$_{resp}$ (FIG. 4A), IFN-γ (FIG. 4B) and IL-2 (FIG. 4C) concentration in supernatant of a T$_{reg}$ suppression assay.

FIGS. 5A and 5B show a target knockdown efficacy screening of mouse FoxP3-specific ASOs in CD4$^+$ T cells of donor mouse 1 (FIG. 5A) and donor mouse 2 (FIG. 5B). CD4$^+$ T cells were treated with mouse FoxP3 antisense oligonucleotides of the present invention at a concentration of 5 μM for three days without the addition of a transfection reagent. FoxP3 and HPRT1 mRNA expression was analyzed using the QuantiGene® Singleplex assay (ThermoFisher) and the FoxP3 expression values were normalized to HPRT1 values.

FIG. 6 depicts dose-dependent FoxP3 mRNA knockdown by selected FoxP3 ASOs in CD4$^+$ T cells. CD4$^+$ T cells were treated for three days with mouse ASOs of the present invention at concentrations of 6 μM, 2 μM, 600 nM, 200 nM, 60 nM, 20 nM, 6 nM, 2 nM.

FIGS. 7A and 7B depict the effect of FoxP3 knockdown in mouse natural T$_{regs}$ on their suppressive capacity. The percentage of FoxP3$^+$ cells (pre-gated on CD4$^+$ CD25$^+$ cells) was reduced by more than 90% after treatment with all ASOs investigated, resulting in less than 2% CD4$^+$CD25$^+$ FoxP3$^+$ cells (FIG. 7A). Treatment with four of the seven analyzed mouse FoxP3-specific ASOs potently reduced the suppressive capacity of the T$_{regs}$, as T$_{resp}$ could proliferate better than in co-cultures with mock- or control oligo-treated T$_{regs}$ (FIG. 7B).

Figure 8A:
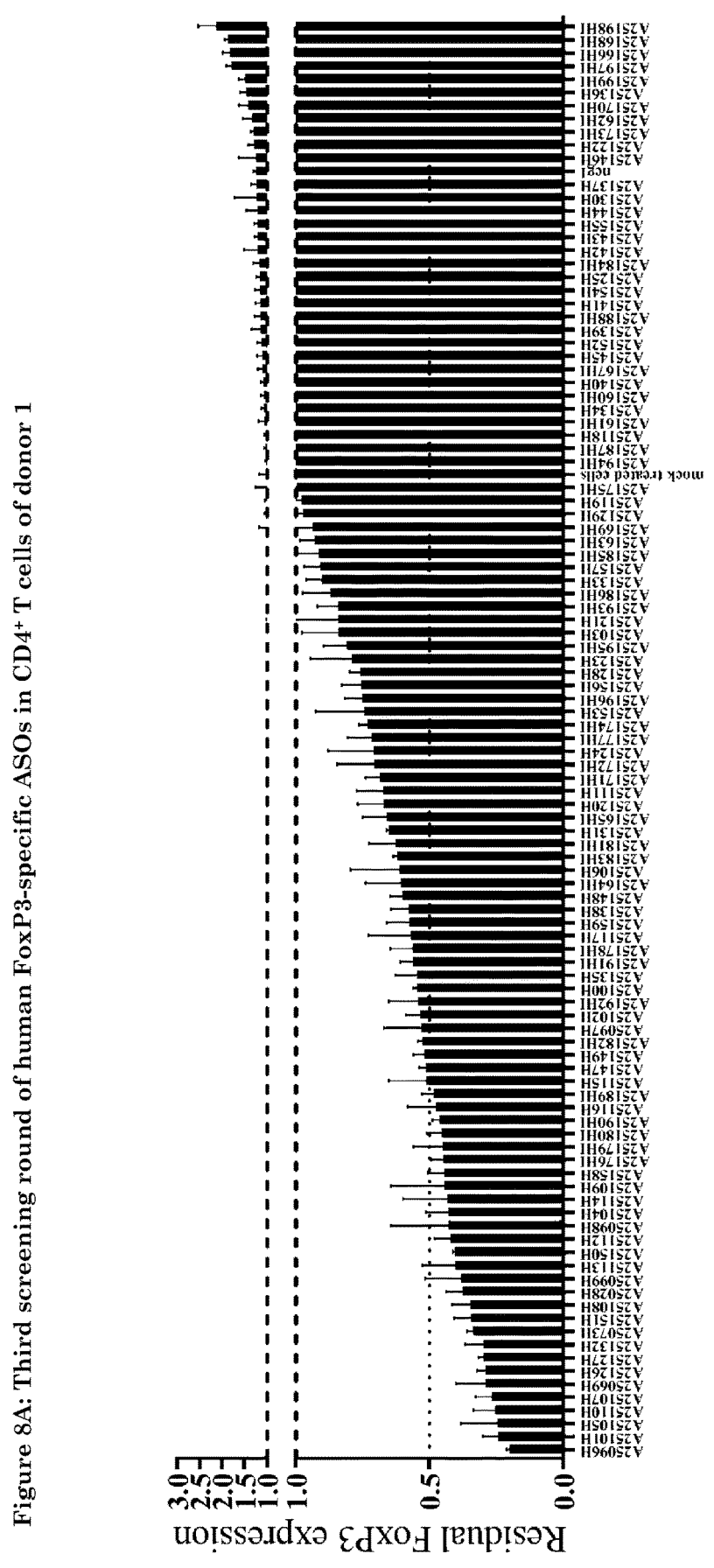

FIGS. 8A and 8B show a third screening round of human FoxP3-specific ASOs in CD4$^+$ T cells of donor 1 (FIG. 8A) and donor 2 (FIG. 8B).

FIG. 9 depicts the dose-dependent FoxP3 mRNA knockdown by selected FoxP3 ASOs in regulatory T cells after 3 days ASO treatment.

FIG. 10 depicts the dose-dependent FoxP3 mRNA knockdown by selected FoxP3 ASOs in regulatory T cells after 3, 6 and 10 days.

DETAILED DESCRIPTION

The present invention provides human and mouse-specific oligonucleotides such as antisense oligonucleotides which hybridize with mRNA and pre-mRNA sequences of FoxP3 and inhibit the expression, functionality and downstream effects, respectively, of FoxP3, FoxP3 mRNA, FoxP3 pre-mRNA or a combination thereof. Thus, the oligonucleotides such as antisense oligonucleotides of the present invention represent promising and highly efficient tools for use in a method of preventing and/or treating disorders, where the FoxP3 expression, functionality, and downstream effects, respectively, deviates from the expression, functionality and downstream effects in a healthy subject. The FoxP3 expression for example is involved in the induction and/or maintenance of the disease and/or mediates resistance to another therapy. The oligonucleotide such as the antisense oligonucleotide of the present invention hybridizes for example with a nucleic acid sequence of FoxP3 of SEQ ID NO. 1 (human mRNA), of SEQ ID NO. 2 (human pre-mRNA), of SEQ ID NO. 324 (mouse mRNA) and/or of SEQ ID NO. 325 (mouse pre-mRNA), wherein the antisense oligonucleotide inhibits at least 40% of the FoxP3 expression within 6 to 240 h, 12 to 216 h, 18 to 120 h or 24 to 72 h, or 12 h, 24 h, 36 h, 48 h, 60 h, 72 h, 84 h, 96 h, 108 h, 120 h, 132 h, 144 h, 156 h, 168 h, 180 h, 192 h, 204 h, 216 h, 228 h or 240 h from administration of the antisense oligonucleotide.

An oligonucleotide of the present invention is an aptamer, a siRNA, preferably an antisense oligonucleotide.

The present invention provides for example oligonucleotides for reducing the levels of the transcription factor FoxP3. In particular, the present invention relates to compounds, particularly oligonucleotides, which in preferred embodiments, hybridize with mRNA and/or pre-mRNA encoding FoxP3 thereby subsequently recruiting RNaseH. Such compounds reduce FoxP3 mRNA and/or FoxP3 pre-mRNA levels and decrease the amount of functional FoxP3 transcription factor, such that the effect and/or expression of further downstream effectors are impaired.

Inhibiting according to the present invention includes reducing an effect such as expression in different percentages and amounts, respectively.

The concept of the present invention is the provision of an oligonucleotide such as an antisense oligonucleotide mediating the limitation of available FoxP3 mRNA for protein expression. In order to limit protein expression, the oligonucleotide requires the presence of a complementary mRNA and/or pre-mRNA representing a hybridization target which allows the formation of heteroduplexes. The oligonucleotides of the present invention hybridize with RNAs of SEQ ID NO. 1 and/or SEQ ID NO. 2. The formation of a heteroduplex between the oligonucleotide and the target RNA leads to RNaseH-mediated degradation or inactivation of the target RNA and thus, reduces the amount of available FoxP3 mRNA for protein expression.

In the following, the elements of the present invention will be described in more detail. These elements are listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

The oligonucleotide such as an antisense oligonucleotide of the present invention consists of or comprises for example 12 to 25 nucleotides, 12 to 15 nucleotides, 15 to 20 nucleotides, 12 to 16 nucleotides, or 15 to 19 nucleotides. The oligonucleotide such as an antisense oligonucleotides for example consist of or comprise 12, 13, 14, 15, 16, 17, 18, 19, 20, 21, 22, 23, 24 or 25 nucleotides. The oligonucleotide such as an antisense oligonucleotide of the present invention comprises at least one nucleotide which is modified. The modified nucleotide is for example a bridged nucleotide such as a locked nucleic acid (LNA, e.g., 2',4'-LNA), ENA, a 2 Fluoro modified nucleotide, a 2'O-Methyl modified nucleotide, a 2 O-Methoxy modified nucleotide, a FANA or a combination thereof. The oligonucleotide such as an antisense oligonucleotide of the present invention comprises nucleotides that have for example the same or different modifications. The oligonucleotide such as an antisense oligonucleotide of the present invention comprises for example a modified phosphate backbone, wherein the phosphate is for example a phosphorothioate.

The oligonucleotide such as an antisense oligonucleotide of the present invention comprises the one or more modified nucleotides at the 3'- and/or 5'-end of the oligonucleotide and/or at any position within the oligonucleotide, wherein modified nucleotides follow for example in a row of 1, 2, 3, 4, 5, or 6 modified nucleotides, or a modified nucleotide is combined with one or more unmodified nucleotides. The following Table 1 presents embodiments of oligonucleotides such as antisense oligonucleotides comprising modified nucleotides for example LNA which are indicated by (+) and phosphorothioate (PTO) indicated by (*). The oligonucleotides such as antisense oligonucleotides consisting of or comprising the sequences of Table 1 may comprise any other modified nucleotide and/or any other combination of modified and unmodified nucleotides. Antisense oligonucleotides of Table 1 hybridize with the mRNA of human FoxP3 (SEQ ID NO. 1; NM_014009.3) or with intronic regions of the pre-mRNA of human FoxP3 (SEQ ID NO. 2; GRCh38.p13 (GCF_000001405.39, Chr X (NC_000023.11): 49,249, 986K-49,226,382-pre-mRNA positions), indicated by "I" in the following Table 1:

TABLE 1

List of human FoxP3-specific antisense oligonucleotides and a control oligonucleotide. An "H" after the antisense oligonucleotide ID indicates a human FoxP3-specific sequence that binds to the FoxP3 mRNA and/or an exonic region of the pre-mRNA, a "HM" after the antisense oligonucleotide ID indicates a human/mouse cross-reactive FoxP3 sequence that binds to an exonic region of the pre-mRNA and a "HI" after the antisense oligonucleotide ID indicates a human FoxP3-specific sequence that binds to an intronic region of the pre-mRNA. *refers to exon spanning oligonucleotides such as antisense oligonucleotides, position depicted in Table 1 indicates position on mRNA SEQ ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 3 | A25004H | TTCGAAGACCTTCTCAC | +T*+T*+C*G*A*A*G*A*C*C*T*T*C*T*+C*+A*+C | 7838 |
| 4 | A25005H | GAAGATGGTCCGCCTGG | +G*+A*+A*G*A*T*G*G*T*C*C*G*C*C*+T*+G*+G | 6847 |
| 5 | A25006H | CAGAAGATGGTCCGCCT | +C*+A*+G*A*A*G*A*T*G*G*T*C*C*G*+C*+C*+T | 6845 |
| 6 | A25008H | TCCAGAAGATGGTCCGC | +T*+C*+C*A*G*A*A*G*A*T*G*G*T*C*+C*+G*+C | 6843 |
| 7 | A25009H | ATCCAGAAGATGGTCCG | +A*+T*+C*C*A*G*A*A*G*A*T*G*G*T*+C*+C*+G | 6842 |
| 8 | A25011H | CTTGTCGGATGATGCC | +C*+T*+T*G*T*C*G*G*A*T*G*A*T*+G*+C*+C | 5119 |
| 9 | A25012H | CTACGATGCAGCAGGAG | +C*+T*+A*C*G*A*T*G*C*A*G*C*A*G*+G*+A*+G | 5101 |
| 10 | A25013H | CGTGGCGTAGGTGAAAG | +C*+G*+T*G*G*C*GMT*A*G*G*T*G*A*+A*+A*+G | 4205 |
| 11 | A25014H | ATGAGCGTGGCGTAGGT | +A*+T*+G*A*G*C*G*T*G*G*C*G*T*A*+G*+G*+T | 4200 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 12 | A25015H | ATGAGCGTGGCGTAGG | +A*+T*+G*A*G*C*G*T*G*G*C*G*T*+A*+G*+G | 4199 |
| 13 | A25016H | GATGAGCGTGGCGTAGG | +G*+A*+T*G*A*G*C*G*T*G*G*C*G*T*+A*+G*+G | 4199 |
| 14 | A25017H | ATGAGCGTGGCGTAG | +A*+T*+G*A*G*C*G*T*G*G*C*G*+T*+A*+G | 4198 |
| 15 | A25018H | GATGAGCGTGGCGTAG | +G*+A*+T*G*A*G*C*G*T*G*G*C*G*+T*+A*+G | 4198 |
| 16 | A25019H | GGATGAGCGTGGCGTAG | +G*+G*+A*T*G*A*G*C*G*T*G*G*C*G*+T*+A*+G | 4198 |
| 17 | A25020H | GGATGAGCGTGGCGTA | +G*+G*+A*T*G*A*G*C*G*T*G*G*C*+G*+T*+A | 4197 |
| 18 | A25021H | CGGATGAGCGTGGCGTA | +C*+G*+G*A*T*G*A*G*C*G*T*G*G*C*+G*+T*+A | 4197 |
| 19 | A25022H | CCAGCGGATGAGCGTG | +C*+C*+A*G*C*G*G*A*T*G*A*G*C*+G*+T*+G | 4192 |
| 20 | A25023H | CAGTGGTAGATCTCATT | +C*+A*+G*T*G*G*T*A*G*A*T*C*T*C*A*+T*+T | 2780 |
| 21 | A25025H | GACTCAGGTTGTGGCGG | +G*+A*C*T*C*A*G*G*T*T*G*T*G*G*C*+G*+G | 2526 |
| 22 | A25026H | GCGGAACTCCAGCTCAT | +G*+C*+G*G*A*A*C*T*C*C*A*G*C*T*+C*+A*+T | 2455 |
| 23 | A25027H | CGCTGCTTCTGTGTAGG | +C*+G*C*T*G*C*T"T*C*T*G*T*G*T*+A*+G*+G | 1820 |
| 24 | A25028H | TGAGCGAGCACGTGTTG | +T*+G*+A*G*C*G*A*G*C*A*C*G*T*G*+T*+T*+G | 1778 |
| 25 | A25029H | GCCGTGTGTGTGAGCGA | +G*+C*C*G*T*G*T*G*T*G*T*G*A*G*+C*+G*+A | 1768 |
| 26 | A25030H | GCGTGAGATACACAGGT | +G*+C*+G*T*G*A*G*A*T*A*C*A*C*A*+G*+G*+T | 1739 |
| 27 | A25031H | AGCTCGGCTGCAGTTTA | +A*+G*C*T*C*G*G*C*T*G*C*A*G*T*+T*+T*+A | 1510 |
| 28 | A25032HI | GATCGATGGAGTGTGGT | +G*+A*+T*C*G*A*T*G*G*A*G*T*G*T*+G*+G*+T | 15174 |
| 29 | A25033HI | TCGGCGACATTACTATT | +T*+C*G*G*C*G*A*C*A*T*T*A*C*T*+A*+T*+T | 15058 |
| 30 | A25034HI | CCTCGGCGACATTACT | +C*+C*+T*C*G*G*C*G*A*C*A*T*T*+A*+C*+T | 15055 |
| 31 | A25035HI | GTCCAACAATCGGCACT | +G*+T*C*C*A*A*C*A*A*T*C*G*G*C*+A*+C*+T | 14551 |
| 32 | A25036HI | CGTGGATCGTCCAACCT | +C*G*+T*G*G*A*T*C*G*T*C*C*A*A*+C*+C*+T | 12736 |
| 33 | A25037HI | TCGTGGATCGTCCAAC | +T*+C*+G*T*G*G*A*T*C*G*T*C*C*+A*+A*+C | 12734 |
| 34 | A25038HMI | CACAGGTTTCGTTCCGA | +C*+A*+C*A*G*T*T*T*C*G*TT*C*+C*+G*+A | 11933 |
| 35 | A25039HI | GCTTCATCGCACACCACG | +G*+C*+T*T*C*A*T*C*G*A*C*A*C*C*+A*+C*+G | 11886 |
| 36 | A25040HI | TTTCCGCCATTGACGTC | +T*+T**C*C*G*C*C*A*T*T*G*A*C*G*+T*+C | 11849 |
| 37 | A25041HI | TTTCGTTCCGAGAACT | +T*+T*+T*C*G*T*T*C*C*G*A*G*A*+A*+C*+T | 11938 |
| 38 | A25044HI | TCAGATGCCGAGTTCCG | +T*+C*+A*G*A*T*G*C*C*G*A*G*T*T*+C*+C*+G | 10832 |
| 39 | A25045HI | CCGAGTTCCGTAGTCC | +C*+C*+G*A*G*T*T*C*C*G*T*A*G*T*+C*+C | 10838 |
| 40 | A25046HI | GATCATGCACGGATCCA | +G*+A*+T*C*A*T*G*C*A*C*G*G*A*T*C*+C*+A | 10450 |
| 41 | A25047HI | CGGACTTTCTCCTCGGA | +C*+G*+G*A*C*T*T*T*C*T*C*C*T*C*G*+G*+A | 9995 |
| 42 | A25048HI | GATACTCGACCACCTGA | +G*+A*+T*A*C*T*C*G*A*C*C*A*C*C*+T*+G*+A | 9645 |
| 43 | A25049HI | GTATGAGATACTCGACC | +G*+T*+A*T*G*A*G*A*T*A*C*T*C*G*+A*+C*+C | 9639 |
| 44 | A25050HI | ACGGCCATTCGCAGGTG | +A*+C*+G*G*C*C*A*T*T*C*G*C*A*G*+G*+T*+G | 8247 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 45 | A25051HI | AAGACGGCCATTCGCAG | +A*+A*+G*A*C*G*G*C*C*A*T*T*C*G*+C*+A*+G | 8244 |
| 46 | A25052HI | AAGACGGCCATTCGCA | +A*+A*+G*A*C*G*G*C*C*A*T*T*C*+G*+C*+A | 8243 |
| 47 | A25053HI | GTGCGGATGTCGTATGT | +G*+T*+G*C*G*G*A*T*G*T*C*G*T*A*+T*+G*+T | 5608 |
| 48 | A25054HI | CAGGTGCGGATGTCGTA | +C*+A*+G*G*T*G*C*G*G*A*T*G*T*C*+G*+T*+A | 5605 |
| 49 | A25055HI | CAGGTGCGGATGTCGT | +C*+A*+G*G*T*G*C*G*G*A*T*G*T*+C*+G*+T | 5604 |
| 50 | A25057HI | TTAGGTGTGGCGCTAGG | +T*+T*+A*G*G*T*G*T*G*G*C*G*C*T*+A*+G*+G | 3617 |
| 51 | A25060HI | GTTCAGAGACAGTCGG | +G*+T*+T*C*A*G*A*G*A*C*A*G*T*+C*+G*+G | 3558 |
| 52 | A25061HI | GTTCGGTGTGGAGTGA | +G*+T*T*C*G*G*T*G*T*G*G*A*G*+T*+G*+A | 3431 |
| 53 | A25062HI | TCGAGTATCTTACGTG | +T*+C*G*A*G*T*A*T*C*T*T*A*C*+G*+T*+G | 3361 |
| 54 | A25063HI | CGAGTATCTTACGTG | +C*+G*+A*G*T*A*T*C*T*T*A*C*+G*+T*+G | 3361 |
| 55 | A25065H | GTCGCATGTTGTGGAAC | +G*T*+C*G*C*A*T*G*T*T*G*T*G*G*+A*+A*+C | 4225 |
| 23 | A25068H | CGCTGCTTCTGTGTAGG | +C*+G*C*T*G*C*T*T*C*T*G*T*G*T*+A*+G*+G | 1820 |
| 56 | A25069H | GAGCGAGCACGTGTTGG | +G*+A*+G*C*G*A*G*C*A*C*G*T*G*T*T*+G*+G | 1779 |
| 24 | A25070H | TGAGCGAGCACGTGTTG | +T*+G*+A*G*C*G*A*G*C*A*C*G*T*G*+T*T*+G | 1778 |
| 57 | A25071H | GTGAGCGAGCACGTGTT | +G*+T*G*A*G*C*G*A*G*C*A*C*G*T*G*+T*+T | 1777 |
| 25 | A25072H | GCCGTGTGTGTGAGCGA | +G*+C*C*G*T*G*T*G*T*G*T*G*A*G*+C*+G*+A | 1768 |
| 58 | A25073H | CGTGAGATACACAGGTG | +C*+G*+T*G*A*G*A*T*A*C*A*C*A*G*+G*T*+G | 1740 |
| 26 | A25074H | GCGTGAGATACACAGGT | +G*+C*+G*T*G*A*G*A*T*A*C*A*C*A*G*+G*+T | 1739 |
| 26 | A25075H | GCGTGAGATACACAGGT | +G*+C*+G*T*G*A*G*A*T*A*C*A*C*A*+G*G*+T | 1739 |
| 26 | A25076H | GCGTGAGATACACAGGT | +G*+C*G*T*G*A*G*A*T*A*C*A*C*A*+G*+G*+T | 1739 |
| 59 | A25077H | ATGCGTGAGATACACAG | +A*+T*+G*C*G*T*G*A*G*A*T*A*C*A*C*+A*+G | 1737 |
| 27 | A25078H | AGCTCGGCTGCAGTTTA | +A*G*+C*T*C*G*G*C*T*G*C*A*G*T*+T*+T*+A | 1510 |
| 60 | A25079HI | TCGATGGAGTGTGGTCA | +T*+C*+G*A*T*G*G*A*G*T*G*T*G*G*+T*+C*+A | 15176 |
| 61 | A25080HI | AGATCGATGGAGTGTGG | +A*+G*+A*T*C*G*A*T*G*G*A*G*T*G*+T*+G*+G | 15173 |
| 62 | A25081HI | CCTCGGCGACATTACTA | +C*+C*+T*C*G*G*C*G*A*C*A*T*T*A*+C*+T*+A | 15056 |
| 63 | A25082HI | CTCGGCGACATTACTA | +C*+T*+C*G*G*C*G*A*C*A*T*T*A*+C*+T*+A | 15056 |
| 64 | A25083HI | GCTAAACTACGGTTGAC | +G*+C*+T*A*A*A*C*T*A*C*G*G*TT*+G*+A*+C | 14882 |
| 65 | A25084HI | GTTTCGTTCCGAGAACT | +G*+T*+T*T*C*G*T*T*C*C*G*A*G*A*A*+C*+T | 11938 |
| 66 | A25085HMI | AGGTTTCGTTCCGAGAA | +A*+G*+G*T*T*C*G*T*T*C*C*G*A*+G*+A*+A | 11936 |
| 67 | A25086HI | GATGCCGAGTTCCGTAG | +G*+A*T*G*C*C*G*A*G*T*T*C*C*G*+T*+A*+G | 10835 |
| 68 | A25087HI | AGATGCCGAGTTCCGTA | +A*+G*+A*T*G*C*C*G*A*G*TT*C*C*G*+T*+A | 10834 |
| 69 | A25088HI | GTGATCATGCACGGATC | +G*+T*G*A*T*C*A*T*G*C*A*C*G*G*+A*+T*+C | 10448 |

TABLE 1-continued

List of human FoxP3-specific antisense oligonucleotides and a control oligonucleotide. An "H" after the antisense oligonucleotide ID indicates a human FoxP3-specific sequence that binds to the FoxP3 mRNA and/or an exonic region of the pre-mRNA, a "HM" after the antisense oligonucleotide ID indicates a human/mouse cross-reactive FoxP3 sequence that binds to an exonic region of the pre-mRNA and a "HI" after the antisense oligonucleotide ID indicates a human FoxP3-specific sequence that binds to an intronic region of the pre-mRNA. *refers to exon spanning oligonucleotides such as antisense oligonucleotides, position depicted in Table 1 indicates position on mRNA SEQ ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 70 | A25089HI | TTAAAGACGGCCATTCG | +T*+T*+A*A*A*G*A*C*G*G*C*C*A*T*+T*+C*+G | 8241 |
| 71 | A25090HI | AGGTGCGGATGTCGTAT | +A*+G*+G*T*G*C*G*G*A*T*G*T*C*G*+T*+A*+T | 5606 |
| 72 | A25091HI | GTGCGGATGTCGTATG | +G*+T*+G*C*G*G*A*T*G*T*C*G*T*A*+T*+G | 5607 |
| 73 | A25092HI | AGGTGCGGATGTCGTA | +A*+G*+G*T*G*C*G*G*A*T*G*T*C*+G*+T*+A | 5605 |
| 74 | A25093HI | ACAGGTGCGGATGTCG | +A*C*+A*G*G*T*G*C*G*G*A*T*G*+T*+C*+G | 5603 |
| 75 | A25095HI | GTTAGGTGTGGCGCTAG | +G*+T*+T*A*G*G*T*G*T*G*G*C*G*C*+T*+A*+G | 3616 |
| 56 | A25096H | GAGCGAGCACGTGTTGG | +G*+A*+G*C*G*A*G*C*A*C*G*T*G*T*T*+G*+G | 1779 |
| 56 | A25097H | GAGCGAGCACGTGTTGG | +G*A*+G*C*G*A*G*C*A*C*G*T*G*T*T*+G*+G | 1779 |
| 56 | A25098H | GAGCGAGCACGTGTTGG | +G*+A*G*C*G*A*G*C*A*C*G*T*G*T*T*+G*+G | 1779 |
| 58 | A25099H | CGTGAGATACACAGGTG | +C*G*+T*G*A*G*A*T*A*C*A*C*A*G*+G*+T*+G | 1740 |
| 58 | A25100H | CGTGAGATACACAGGTG | +C*G*+T*G*A*G*A*T*A*C*A*C*A*G*+G*T*+G | 1740 |
| 58 | A25101H | CGTGAGATACACAGGTG | +C*+G*+T*G*A*G*A*T*A*C*A*C*A*G*+G*T*+G | 1740 |
| 24 | A25102H | TGAGCGAGCACGTGTTG | +T*G*+A*G*C*G*A*G*C*A*C*G*T*G*+T*+T*+G | 1778 |
| 24 | A25103H | TGAGCGAGCACGTGTTG | +T*G*+A*G*C*G*A*G*C*A*C*G*T*G*+T*T*+G | 1778 |
| 24 | A25104H | TGAGCGAGCACGTGTTG | +T*+G*+A*G*C*G*A*G*C*A*C*G*T*G*+T*T*+G | 1778 |
| 23 | A25105H | CGCTGCTTCTGTGTAGG | +C*G*+C*T*G*C*T*T*C*T*G*T*G*T*+A*+G*+G | 1820 |
| 25 | A25106H | GCCGTGTGTGTGAGCGA | +G*+C*C*G*T*G*T*G*T*G*T*G*A*G*+C*+G*+A | 1768 |
| 26 | A25107H | GCGTGAGATACACAGGT | +G*+C*G*T*G*A*G*A*T*A*C*A*C*A*+G*+G*+T | 1739 |
| 26 | A25108H | GCGTGAGATACACAGGT | +G*+C*G*T*G*A*G*A*T*A*C*A*C*A*+G*G*+T | 1739 |
| 27 | A25109H | AGCTCGGCTGCAGTTTA | +A*G*+C*T*C*G*G*C*T*G*C*A*G*T*+T*+T*+A | 1510 |
| 26 | A25110H | GCGTGAGATACACAGGT | +G*C*+G*T*G*A*G*A*T*A*C*A*C*A*+G*+G*+T | 1739 |
| 59 | A25111H | ATGCGTGAGATACACAG | +A*T*+G*C*G*T*G*A*G*A*T*A*C*A*C*+A*+G | 1737 |
| 34 | A25112H | CACAGGTTTCGTTCCGA | +C*+A*+C*A*G*G*T*T*T*C*G*T*T*C*C*+G*+A | 11933 |
| 34 | A25113H | CACAGGTTTCGTTCCGA | +C*A*+C*A*G*G*T*T*T*C*G*T*T*C*+C*G*+A | 11933 |
| 34 | A25114H | CACAGGTTTCGTTCCGA | +C*+A*+C*A*G*G*T*T*T*C*G*T*T*C*+C*G*+A | 11933 |
| 49 | A25115H | CAGGTGCGGATGTCGT | +C*+A*+G*G*T*G*C*G*G*A*T*G*T*C*+G*+T | 5604 |
| 66 | A25116H | AGGTTTCGTTCCGAGAA | +A*+G*G*T*TT*C*G*T*T*C*C*G*A*+G*A*+A | 11936 |
| 73 | A25117H | AGGTGCGGATGTCGTA | +A*G*+G*T*G*C*G*G*A*T*G*T*C*+G*+T*+A | 5605 |
| 76 | A25118H | GAAAAACCACGCTGTACG | +G*+A*+A*A*A*A*C*C*A*C*G*C*T*G*T*+A*+C*+G | 15817 |
| 77 | A25120H | ATCCAGAAGATGGTCCGC | +A*+T*+C*C*A*G*A*A*G*A*T*G*G*T*C*+C*+G*+C | 6843 |
| 78 | A25122H | CGTGGCGTAGGTGAAAGG | +C*+G*+T*G*G*C*G*T*A*G*G*T*G*A*A*+A*+G*+G | 4206 |
| 79 | A25123H | GGATGAGCGTGGCGTAGG | +G*+G*+A*T*G*A*G*C*G*T*G*G*C*G*T*+A*+G*+G | 4199 |
| 80 | A25125H | TGCGGAACTCCAGCTCAT | +T*+G*+C*G*G*A*A*C*T*C*C*A*G*C*T*+C*+A*+T | 2455 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 81 | A25126H | GAAGTAATCTGTGCGAGC | +G*+A*+A*G*T*A*A*T*C*T*G*T*G*C*G*+A*+G*+C | 2069 |
| 82 | A25127H | GTTGTTTGAGTGTACTGA | +G*+T*+T*G*T*T*T*G*A*G*T*G*T*A*C*+T*+G*+A | 1966 |
| 83 | A25128H | GTGAGCGAGCACGTGTTG | +G*+T*+G*A*G*C*G*A*G*C*A*C*G*T*G*+T*T*+G | 1778 |
| 84 | A25129H | TGTGAGCGAGCACGTGTT | +T*G*+T*+G*A*G*C*G*A*G*C*A*C*G*T*G*+T*+T | 1777 |
| 85 | A25130H | GGCCGTGTGTGTGAGCGA | +G*+G*+C*C*G*T*G*T*G*T*G*T*G*A*G*+C*G*+A | 1768 |
| 86 | A25131H | AATTCTAACAGGCCGTGT | +A*+A*+T*T*C*T*A*A*C*A*G*G*C*C*G*+T*+G*+T | 1758 |
| 87 | A25132H | GTGAATTCTAACAGGCCG | +G*+T*+G*A*A*T*T*C*T*A*A*C*A*G*G*+C*+C*+G | 1755 |
| 88 | A25133H | TATGCGTGAGATACACAG | +T*+A*+T*G*C*G*T*G*A*G*A*T*A*C*A*C*+A*+G | 1737 |
| 89 | A25134H | CATATGCGTGAGATACAC | +C*+A*+T*A*T*G*C*G*T*G*A*G*A*T*A*+C*+A*+C | 1735 |
| 90 | A25135H | CTCGGCTGCAGTTTATTG | +C*+T*+C*G*C*T*G*C*A*G*T*T*T*A*+T*+T*+G | 1513 |
| 91 | A25136H | AGAAAAACCACGCTGTACG | +A*+G*+A*A*A*A*A*C*C*A*C*G*C*T*G*T*+A*+C*+G | 15817 |
| 92 | A25138H | TCGCATGTTGTGGAACTTG | +T*+C*+G*C*A*T*G*T*T*G*T*G*G*A*A*C*+T*+T*+G | 4228 |
| 93 | A25139H | GCGTGGCGTAGGTGAAAGG | +G*+C*+G*T*G*G*C*G*T*A*G*G*T*G*A*A*+A*+G*+G | 4206 |
| 94 | A25140H | AGCGTGGCGTAGGTGAAAG | +A*+G*+C*G*T*G*G*C*G*T*A*G*G*T*G*A*+A*+A*+G | 4205 |
| 95 | A25141H | GAGCGTGGCGTAGGTGAAA | +G*+A*+G*C*G*T*G*G*C*G*T*A*G*G*T*G*+A*+A*+A | 4204 |
| 96 | A25142H | TGAGCGTGGCGTAGGTGAA | +T*+G*+A*G*C*G*T*G*G*C*G*T*A*G*G*T*+G*+A*+A | 4203 |
| 97 | A25143H | ATGAGCGTGGCGTAGGTGA | +A*+T*+G*A*G*C*G*T*G*G*C*G*T*A*G*G*+T*+G*+A | 4202 |
| 98 | A25144H | ATCTCATTGAGTGTCCGCT | +A*+T*+C*T*C*A*T*T*G*A*G*T*G*T*C*C*+G*+C*+T | 2791 |
| 99 | A25145H | GATCTCATTGAGTGTCCGC | +G*+A*+T*C*T*C*A*T*T*G*A*G*T*G*T*C*+C*+G*+C | 2790 |
| 100 | A25146H | GGCTCCGTTTCTTGCGGAA | +G*+G*+C*T*C*C*G*T*TT*C*T*T*G*C*G*+G*+A*+A | 2444 |
| 101 | A25147H | CGCTGCTTCTGTGTAGGCC | +C*+G*C*+T*G*C*T*T*C*T*G*T*G*T*A*G*+G*C*+C | 1822 |
| 101 | A25148H | CGCTGCTTCTGTGTAGGCC | +C*+G*C*T*G*C*T*T*C*T*G*T*G*T*A*G*G*+C*+C | 1822 |
| 102 | A25149H | GAATTCTAACAGGCCGTGT | +G*+A*+A*T*T*C*T*A*A*C*A*G*G*C*C*G*+T*+G*+T | 1758 |
| 103 | A25150H | ATGCGTGAGATACACAGGT | +A*+T*+G*C*G*T*G*A*G*A*T*A*C*A*C*A*+G*+G*+T | 1739 |
| 104 | A25151H | TATGCGTGAGATACACAGG | +T*+A*+T*G*C*G*T*G*A*G*A*T*A*C*A*C*+A*+G*+G | 1738 |
| 105 | A25152H | ATATGCGTGAGATACACAG | +A*+T*+A*T*G*C*G*T*G*A*G*A*T*A*C*A*C*+A*+G | 1737 |
| 105 | A25153H | ATATGCGTGAGATACACAG | +A*+T*A*T*G*C*G*T*G*A*G*A*T*A*C*A*C*+A*+G | 1737 |
| 105 | A25154H | ATATGCGTGAGATACACAG | +A*T*+A*T*G*C*G*T*G*A*G*A*T*A*C*A*C*+A*+G | 1737 |
| 105 | A25155H | ATATGCGTGAGATACACAG | +A*+T*A*T*G*C*G*T*G*A*G*A*T*A*C*A*C*+A*+G | 1737 |
| 106 | A25156H | GTGCATATGCGTGAGATAC | +G*+T*G*C*A*T*A*T*G*C*G*T*G*A*G*A*+T*A*+C | 1733 |
| 106 | A25157H | GTGCATATGCGTGAGATAC | +G*+T*G*C*+A*T*A*T*G*C*G*T*G*A*G*A*T*+A*+C | 1733 |
| 107 | A25158H | GCTCGGCTGCAGTTTATTG | +G*+C*+T*C*G*G*C*T*G*C*A*G*T*T*T*A*+T*+T*+G | 1513 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 108 | A25159H | GGAGCTCGGCTGCAGTTTA | +G*+G*+A*G*C*T*C*G*G*C*T*G*C*A*G*T*+T*+T*+A | 1510 |
| 109 | A25160HI | CCTCGGCGACATTACTAT | +C*+C*+T*C*G*G*C*G*A*C*A*T*T*A*C*+T*+A*+T | 15040 |
| 110 | A25161HI | CGTGGATCGTCCAACCTG | +C*+G*+T*G*G*A*T*C*G*T*C*C*A*A*C*+C*+T*+G | 12720 |
| 111 | A25162HI | AGATGCCGAGTTCCGTAG | +A*+G*+A*T*G*C*C*G*A*G*TT*C*C*G*+T*+A*+G | 10818 |
| 112 | A25163HI | CTTAAAGACGGCCATTCG | +C*+T*+T*A*A*A*G*A*C*G*G*C*C*A*T*+T*+C*+G | 8224 |
| 113 | A25164HI | AGGTGCGGATGTCGTATG | +A*+G*+G*T*G*C*G*G*A*T*G*T*C*G*T*+A*+T*+G | 5590 |
| 114 | A25165HI | CAGGTGCGGATGTCGTAT | +C*+A*+G*G*T*G*C*G*G*A*T*G*T*C*G*+T*+A*+T | 5589 |
| 115 | A25166HI | GGTTAGGTGTGGCGCTAG | +G*+G*+T*T*A*G*G*T*G*T*G*G*C*G*C*+T*+A*+G | 3599 |
| 116 | A25167HI | ATTATCGAGTATCTTACG | +A*+T*+T*A*T*C*G*A*G*T*A*T*C*T*T*+A*+C*+G | 3342 |
| 117 | A25168HI | AGGAGATCGATGGAGTGTG | +A*+G*+G*A*G*A*T*C*G*A*T*G*G*A*G*T*+G*+T*+G | 15154 |
| 118 | A25169HI | CCTCGGCGACATTACTATT | +C*+C*+T*C*G*G*C*G*A*C*A*T*T*A*C*T*+A*+T*+T | 15040 |
| 119 | A25170HI | GGTCTCCTCTAAAGCGATA | +G*+G*+T*C*T*C*C*T*C*T*A*A*A*G*C*G*+A*+T*+A | 14919 |
| 120 | A25171HI | GGTAGGTCCACACAGCTAA | +G*+G*+T*A*G*G*T*C*C*A*C*A*C*A*G*C*+T*+A*+A | 14852 |
| 121 | A25172HI | AACAATCGGCACTTGGTCA | +A*+A*+C*A*A*T*C*G*G*C*A*C*T*T*G*G*+T*+C*+A | 14539 |
| 122 | A25173HI | TGTGCGAGAGGAGGATTGC | +T*+G*+T*G*C*G*A*G*A*G*G*A*G*G*A*T*+T*+G*+C | 13198 |
| 123 | A25174HI | CACGCTCTGGCCAACTAGG | +C*+A*+C*G*C*T*C*T*G*G*C*C*A*A*C*T*+A*+G*+G | 12632 |
| 124 | A25175HI | GCCTTCGCCAATACAGAGC | +G*+C*+C*T*T*C*G*C*C*A*A*T*A*C*A*G*+A*+G*+C | 12509 |
| 125 | A25176HI | CTCAGTATGTGTAGGCCAG | +C*+T*+C*A*G*T*A*T*G*T*G*T*A*G*G*C*+C*+A*+G | 12245 |
| 126 | A25177HI | CGTTCCGAGAACTGGCTGC | +C*+G*+TT*C*C*G*A*G*A*A*C*T*G*G*C*+T*+G*+C | 11926 |
| 127 | A25178HI | TCGTTCCGAGAACTGGCTG | +T*+C*+G*T*T*C*C*G*A*G*A*A*C*T*G*G*+C*+T*+G | 11925 |
| 128 | A25179HI | TTTCGTTCCGAGAACTGGC | +T*+T*+T*C*G*T*T*C*C*G*A*G*A*A*C*T*+G*+G*+C | 11923 |
| 129 | A25180HI | GTTTCGTTCCGAGAACTGG | +G*+T*+T*T*C*G*T*T*C*C*G*A*G*A*A*C*+T*+G*+G | 11922 |
| 130 | A25181HI | ACAGGTTTCGTTCCGAGAA | +A*+C*+A*G*G*T*T*T*C*G*T*T*C*C*G*A*+G*+A*+A | 11918 |
| 131 | A25182HI | CACAGGTTTCGTTCCGAGA | +C*+A*+C*A*G*G*T*T*T*C*G*TT*C*C*G*+A*+G*+A | 11917 |
| 132 | A25183HI | CCACAGGTTTCGTTCCGAG | +C*+C*+A*C*A*G*G*T*TT*C*G*T*T*C*C*+G*+A*+G | 11916 |
| 133 | A25184HI | TTTCGGTGCAAATGGATGT | +T*+T*+T*C*G*G*T*G*C*A*A*A*T*G*G*A*+T*+G*+T | 11469 |
| 134 | A25185HI | AGGACCGAGCTGACATTAC | +A*+G*+G*A*C*C*G*A*G*C*T*G*A*C*A*T*+T*+A*+C | 10257 |
| 135 | A25186HI | ATACTCGACCACCTGAGCC | +A*+T*+A*C*T*C*G*A*C*C*A*C*C*T*G*A*+G*+C*+C | 9630 |
| 136 | A25187HI | ATGAGATACTCGACCACCT | +A*+T*+G*A*G*A*T*A*C*T*C*G*A*C*C*A*+C*+C*+T | 9625 |
| 137 | A25188HI | CATTCGCAGGTGCTGACAT | +C*+A*+T*T*C*G*C*A*G*G*T*G*C*T*G*A*+C*+A*+T | 8236 |
| 138 | A25189HI | AAAGACGGCCATTCGCAGG | +A*+A*+A*G*A*C*G*G*C*C*A*T*T*C*G*C*+A*+G*+G | 8227 |
| 139 | A25190HI | GTACATTCGCATCATGAGA | +G*+T*+A*C*A*T*T*C*G*C*A*T*C*A*T*G*+A*+G*+A | 5717 |
| 140 | A25191HI | GTGCGGATGTCGTATGTGG | +G*+T*+G*C*G*G*A*T*G*T*C*G*T*A*T*G*+T*+G*+G | 5592 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 141 | A25192HI | AGGTGCGGATGTCGTATGT | +A*+G*+G*T*G*C*G*G*A*T*G*T*C*G*T*A*+T*+G*+T | 5590 |
| 142 | A25193HI | CAGGTGCGGATGTCGTATG | +C*+A*+G*G*T*G*C*G*G*A*T*G*T*C*G*T*+A*+T*+G | 5589 |
| 143 | A25194HI | ACAGGTGCGGATGTCGTAT | +A*+C*+A*G*G*T*G*C*G*G*A*T*G*T*C*G*+T*+A*+T | 5588 |
| 144 | A25195HI | AGCATGAGCCGTATTTATT | +A*+G*+C*A*T*G*A*G*C*C*G*T*A*T*T*T*+A*+T*+T | 5564 |
| 145 | A25196HI | GATGGCCGAATATAGTAGC | +G*+A*+T*G*G*C*C*G*A*A*T*A*T*A*G*T*+A*+G*+C | 4677 |
| 146 | A25197HI | TGTGGCGCTAGGATGAAGG | +T*+G*+T*G*G*C*G*C*T*A*G*G*A*T*G*A*+A*+G*+G | 3606 |
| 147 | A25198HI | GGTTCGGTGTGGAGTGAGG | +G*+G*+T*T*C*G*G*T*G*T*G*G*A*G*T*G*+A*+G*+G | 3415 |
| 148 | A25199HI | TTATCGAGTATCTTACGTG | +T*+T*+A*T*C*G*A*G*T*A*T*C*T*T*A*C*+G*+T*+G | 3343 |
| 149 | A25200H | CTTCGAAGACCTTCTCAC | +C*+T*+T*C*G*A*A*G*A*C*C*T*T*C*T*+C*+A*+C | 7838 |
| 150 | A25201H | AGAAGATGGTCCGCCTGG | +A*+G*+A*A*G*A*T*G*G*T*C*C*G*C*C*+T*+G*+G | 6847 |
| 151 | A25202H | CATCCAGAAGATGGTCCG | +C*+A*+T*C*C*A*G*A*A*G*A*T*G*G*T*+C*+C*+G | 6842 |
| 152 | A25204H | CTACGATGCAGCAGGAGC | +C*+T*+A*C*G*A*T*G*C*A*G*C*A*G*G*+A*+G*+C | 5102 |
| 153 | A25205H | GCCAGCAGCTACGATGCA | +G*+C*+C*A*G*C*A*G*C*T*A*C *G*A*T*+G*+C*+A | 5094 |
| 154 | A25206H | GTGCCTCCGGACAGCAAA | +G*+T*+G*C*C*T*C*C*G*G*A*C*A*G*C*+A*+A*+A | 5019 |
| 155 | A25207H | TCGCATGTTGTGGAACTT | +T*+C*+G*C*A*T*G*T*T*G*T*G*G*A*A*+C*+T*+T | 4227 |
| 156 | A25208H | GCGTGGCGTAGGTGAAAG | +G*+C*+G*T*G*G*C*G*T*A*G*G*T*G*A*+A*+A*+G | 4205 |
| 157 | A25209H | AGCGTGGCGTAGGTGAAA | +A*+G*+C*G*T*G*G*C*G*T*A*G*G*T*G*+A*+A*+A | 4204 |
| 158 | A25210H | TGAGCGTGGCGTAGGTGA | +T*+G*+A*G*C*G*T*G*G*C*G*T*A*G*G*+T*+G*+A | 4202 |
| 159 | A25211H | ATGAGCGTGGCGTAGGTG | +A*+T*+G*A*G*C*G*T*G*G*C*G*T*A*G*+G*+T*+G | 4201 |
| 160 | A25212H | CGGATGAGCGTGGCGTAG | +C*+G*+G*A*T*G*A*G*C*G*T*G*G*C*G*+T*+A*+G | 4198 |
| 161 | A25213H | GCGGATGAGCGTGGCGTA | +G*+C*+G*G*A*T*G*A*G*C*G*T*G*G*C*+G*+T*+A | 4197 |
| 162 | A25214H | AGCGGATGAGCGTGGCGT | +A*+G*+C*G*G*A*T*G*A*G*C*G*T*G*G*+C*+G*+T | 4196 |
| 163 | A25215H | CAGCGGATGAGCGTGGCG | +C*+A*+G*C*G*G*A*T*G*A*G*C*G*T*G*+G*+C*+G | 4195 |
| 164 | A25216H | ATCTCATTGAGTGTCCGC | +A*+T*+C*T*C*A*T*T*G*A*G*T*G*T*C*+C*+G*+C | 2790 |
| 165 | A25217H | AGACTCAGGTTGTGGCGG | +A*+G*+A*C*T*C*A*G*G*T*T*G*T*G*G*+C*+G*+G | 2526 |
| 166 | A25218H | TGAAGTAATCTGTGCGAG | +T*+G*+A*A*G*T*A*A*T*C*T*G*T*G*C*+G*+A*+G | 2068 |
| 167 | A25219H | TCGGCTGCAGTTTATTGG | +T*+C*+G*G*C*T*G*C*A*G*T*T*T*A*T*+T*+G*+G | 1514 |
| 168 | A25220H | GAAGAAAACCACGCTGTA | +G*+A*+A*G*A*A*A*A*C*C*A*C*G*C*T*+G*+T*+A | 15815 |
| 169 | A25221H | TTGGTGAAGTGGACTGACA | +T*+T*+G*G*T*G*A*A*G*T*G*G*A*C*T*G*+A*+C*+A | 15731 |
| 170 | A25223H | TCGAAGACCTTCTCACATC | +T*+C*+G*A*A*G*A*C*C*T*T*C*T*C*A*C*+A*+T*+C | 7841 |
| 171 | A25224H | TTCGAAGACCTTCTCACAT | +T*+T*+C*G*A*A*G*A*C*C*T*T*C*T*C*A*+C*+A*+T | 7840 |
| 172 | A25225H | TCATCCAGAAGATGGTCCG | +T*+C*+A*T*C*C*A*G*A*A*G*A*T*G*G*T*+C*+C*+G | 6842 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 173 | A25227H | CTACGATGCAGCAGGAGCC | +C*+T*+A*C*G*A*T*G*C*A*G*C*A*G*G*A*+G*+C*+C | 5103 |
| 174 | A25228H | GGTGCCTCCGGACAGCAAA | +G*+G*+T*G*C*C*T*C*C*G*G*A*C*A*G*C*+A*+A*+A | 5019 |
| 175 | A25229H | CATGTTGTGGAGGAACTCT | +C*+A*+T*G*T*T*G*T*G*G*A*G*G*A*A*C*+T*+C*+T | 4255 |
| 176 | A25230H | TAGTCCATGTTGTGGAGGA | +T*+A*+G*T*C*C*A*T*G*T*T*G*T*G*G*A*+G*+G*+A | 4250 |
| 177 | A25231H | GATGAGCGTGGCGTAGGTG | +G*+A*+T*G*A*G*C*G*T*G*G*C*G*T*A*G*+G*+T*+G | 4201 |
| 178 | A25232H | CGGATGAGCGTGGCGTAGG | +C*+G*+G*A*T*G*A*G*C*G*T*G*G*C*G*T*+A*+G*+G | 4199 |
| 179 | A25233H | GCGGATGAGCGTGGCGTAG | +G*+C*+G*G*A*T*G*A*G*C*G*T*G*G*C*G*+T*+A*+G | 4198 |
| 180 | A25234H | CAGCGGATGAGCGTGGCGT | +C*+A*+G*C*G*G*A*T*G*A*G*C*G*T*G*G*+C*+G*+T | 4196 |
| 181 | A25235H | GCGTGTGAACCAGTGGTAG | +G*+C*+G*T*G*T*G*A*A*C*C*A*G*T*G*G*+T*+A*+G | 2772 |
| 182 | A25237H | ACTCAGGTTGTGGCGGATG | +A*+C*+T*C*A*G*G*T*T*G*T*G*G*C*G*G*+A*+T*+G | 2529 |
| 183 | A25238H | CTTGTGCAGACTCAGGTTG | +C*+T*+T*G*T*G*C*A*G*A*C*T*C*A*G*G*+T*+T*+G | 2520 |
| 184 | A25239H | TGCGGAACTCCAGCTCATC | +T*+G*+C*G*G*A*A*C*T*C*C*A*G*C*T*C*+A*+T*+C | 2456 |
| 185 | A25240H | TTGCGGAACTCCAGCTCAT | +T*+T*+G*C*G*G*A*A*C*T*C*C*A*G*C*T*+C*+A*+T | 2455 |
| 186 | A25241H | TCTGGCTCCGTTTCTTGCG | +T*+C*+T*G*G*C*T*C*C*G*T*T*T*C*T*T*+G*+C*+G | 2441 |
| 187 | A25242H | CTGAAGTAATCTGTGCGAG | +C*+T*+G*A*A*G*T*A*A*T*C*T*G*T*G*C*+G*+A*+G | 2068 |
| 188 | A25243H | CCTGAAGTAATCTGTGCGA | +C*+C*+T*G*A*A*G*T*A*A*T*C*T*G*T*G*+C*+G*+A | 2067 |
| 189 | A25244H | GTTGTTTGAGTGTACTGAG | +G*+T*+T*G*T*T*T*G*A*G*T*G*T*A*C*T*+G*+A*+G | 1967 |
| 190 | A25245H | GGTTGTTTGAGTGTACTGA | +G*+G*+T*T*G*T*T*T*G*A*G*T*G*T*A*C*+T*+G*+A | 1966 |
| 191 | A25246H | ACGCTGCTTCTGTGTAGGC | +A*+C*+G*C*T*G*C*T*T*C*T*G*T*G*T*A*+G*+G*+C | 1821 |
| 192 | A25247H | GACGCTGCTTCTGTGTAGG | +G*+A*+C*G*C*T*G*C*T*T*C*T*G*T*G*T*+A*+G*+G | 1820 |
| 193 | A25248H | GGTACTGACGCTGCTTCTG | +G*+G*+T*A*C*T*G*A*C*G*C*T*G*C*T*T*+C*+T*+G | 1814 |
| 194 | A25249H | TGTGAGCGAGCACGTGTTG | +T*+G*+T*G*A*G*C*G*A*G*C*A*C*G*T*G*+T*+T*+G | 1778 |
| 195 | A25250H | GTGTGAGCGAGCACGTGTT | +G*+T*+G*T*G*A*G*C*G*A*G*C*A*C*G*T*+G*+T*+T | 1777 |
| 196 | A25251H | GGCCGTGTGTGTGAGCGAG | +G*+G*C*C*G*T*G*T*G*T*G*T*G*A*G*C*G*+A*+G | 1769 |
| 197 | A25252H | TCTAACAGGCCGTGTGTGT | +T*C*+T*+A*A*C*A*G*G*C*C*G*T*G*T*G*+T*+G*+T | 1762 |
| 198 | A25253H | AATTCTAACAGGCCGTGTG | +A*+A*+T*T*C*T*A*A*C*A*G*G*C*C*G*T*+G*+T*+G | 1759 |
| 199 | A25254H | TGAATTCTAACAGGCCGTG | +T*+G*+A*A*T*T*C*T*A*A*C*A*G*G*C*C*+G*+T*+G | 1757 |
| 200 | A25255H | GTGAATTCTAACAGGCCGT | +G*+T*+G*A*A*T*T*C*T*A*A*C*A*G*G*C*+C*+G*+T | 1756 |
| 201 | A25256H | GGTGAATTCTAACAGGCCG | +G*+G*+T*G*A*A*T*T*C*T*A*A*C*A*G*G*C*+C*+G | 1755 |
| 201 | A25257H | GGTGAATTCTAACAGGCCG | +G*+G*+T*G*A*A*T*T*C*T*A*A*C*A*G*G*+C*C*+G | 1755 |
| 202 | A25258H | CATATGCGTGAGATACACA | +C*+A*+T*A*T*G*C*G*T*G*A*G*A*T*A*C*+A*+C*+A | 1736 |
| 203 | A25259H | GTTCCTCTGCAGTCTAAGC | +G*+T*+T*C*C*T*C*T*G*C*A*G*T*C*T*A*+A*+G*+C | 1579 |
| 204 | A25260H | GTAGTTCCTCTGCAGTCTA | +G*+T*+A*G*T*T*C*C*T*C*T*G*C*A*G*T*+C*+T*+A | 1576 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 205 | A25261H | CTCGGCTGCAGTTTATTGG | +C*+T*+C*G*G*C*T*G*C*A*G*T*T*T*A*T*+T*+G*+G | 1514 |
| 206 | A25262HI | GTGTAGCGACAGACAGAT | +G*+T*+G*T*A*G*C*G*A*C*A*G*A*C*A*+G*+A*+T | 15244 |
| 207 | A25263HI | TCGATGGAGTGTGGTCAA | +T*+C*+G*A*T*G*G*A*G*T*G*T*G*G*T*+C*+A*+A | 15160 |
| 208 | A25264HI | AGATCGATGGAGTGTGGT | +A*+G*+A*T*C*G*A*T*G*G*A*G*T*G*T*+G*+G*+T | 15157 |
| 209 | A25265HI | CTCGGCGACATTACTATT | +C*+T*+C*G*G*C*G*A*C*A*T*T*A*C*T*+A*+T*+T | 15041 |
| 109 | A25266HI | CCTCGGCGACATTACTAT | +C*+C*+T*C*G*G*C*G*A*C*A*T*T*A*C*+T*+A*+T | 15040 |
| 210 | A25267HI | TCCTCGGCGACATTACTA | +T*+C*+C*T*C*G*G*C*G*A*C*A*T*T*A*+C*+T*+A | 15039 |
| 211 | A25268HI | CCTCTAAAGCGATACAAG | +C*+C*+T*C*T*A*A*A*G*C*G*A*T*A*C*+A*+A*+G | 14924 |
| 212 | A25269HI | GCTAAACTACGGTTGACA | +G*+C*+T*A*A*A*C*T*A*C*G*G*T*T*G*+A*+C*+A | 14866 |
| 213 | A25270HI | AGCTAAACTACGGTTGAC | +A*+G*+C*T*A*A*A*C*T*A*C*G*G*T*T*+G*+A*+C | 14865 |
| 214 | A25271HI | ACAATCGGCACTTGGTCA | +A*+C*+A*A*T*C*G*G*C*A*C*T*T*G*G*+T*+C*+A | 14540 |
| 110 | A25272HI | CGTGGATCGTCCAACCTG | +C*+G*+T*G*G*A*T*C*G*T*C*C*A*A*C*+C*+T*+G | 12720 |
| 215 | A25273HI | TCGTGGATCGTCCAACCT | +T*+C*+G*T*G*G*A*T*C*G*T*C*C*A*A*+C*+C*+T | 12719 |
| 216 | A25274HI | ACGCTCTGGCCAACTAGG | +A*+C*+G*C*T*C*T*G*G*C*C*A*A*C*T*+A*+G*+G | 12633 |
| 217 | A25275HI | CTTCGCCAATACAGAGCC | +C*+T*+T*C*G*C*C*A*A*T*A*C*A*G*A*+G*+C*+C | 12511 |
| 218 | A25276HI | AATACATGGCCACTCCGC | +A*+A*+T*A*C*A*T*G*G*C*C*A*C*T*C*+C*+G*+C | 12408 |
| 219 | A25277HI | TTTCGTTCCGAGAACTGG | +T*+T*+T*C*G*T*T*C*C*G*A*G*A*A*C*+T*+G*+G | 11923 |
| 220 | A25278HI | GTTTCGTTCCGAGAACTG | +G*+T*+T*T*C*G*T*T*C*C*G*A*G*A*A*+C*+T*+G | 11922 |
| 221 | A25279HI | ACAGGTTTCGTTCCGAGA | +A*+C*+A*G*G*T*T*T*C*G*T*T*C*C*G*+A*+G*+A | 11918 |
| 222 | A25280HI | CCACAGGTTTCGTTCCGA | +C*+C*+A*C*A*G*G*T*T*T*C*G*T*T*C*+C*+G*+A | 11916 |
| ill | A25281HI | AGATGCCGAGTTCCGTAG | +A*+G*+A*T*G*C*C*G*A*G*TT*C*C*G*+T*+A*+G | 10818 |
| 223 | A25282HI | GATCATGCACGGATCCAG | +G*+A*+T*C*A*T*G*C*A*C*G*G*A*T*C*+C*+A*+G | 10434 |
| 224 | A25283HI | CCGAGCTGACATTACCTG | +C*+C*+G*A*G*C*T*G*A*C*A*T*T*A*C*+C*+T*+G | 10261 |
| 225 | A25284HI | GTATGAGATACTCGACCA | +G*+T*+A*T*G*A*G*A*T*A*C*T*C*G*A*+C*+C*+A | 9623 |
| 226 | A25285HI | AAGACGGCCATTCGCAGG | +A*+A*+G*A*C*G*G*C*C*A*T*T*C*G*C*+A*+G*+G | 8228 |
| 112 | A25286HI | CTTAAAGACGGCCATTCG | +C*+T*+T*A*A*A*G*A*C*G*G*C*C*A*T*+T*+C*+G | 8224 |
| 227 | A25287HI | GCTTAAAGACGGCCATTC | +G*+C*+TT*A*A*A*G*A*C*G*G*C*C*A*+T*+T*+C | 8223 |
| 228 | A25288HI | GCGTGTGACCTATGTGGT | +G*+C*+G*T*G*T*G*A*C*C*T*A*T*G*T*+G*+G*+T | 5798 |
| 229 | A25289HI | GTACATTCGCATCATGAG | +G*+T*+A*C*A*T*T*C*G*C*A*T*C*A*T*+G*+A*+G | 5717 |
| 230 | A25290HI | GGTGCGGATGTCGTATGT | +G*+G*+T*G*C*G*G*A*T*G*T*C*G*T*A*+T*+G*+T | 5591 |
| 113 | A25291HI | AGGTGCGGATGTCGTATG | +A*+G*+G*T*G*C*G*G*A*T*G*T*C*G*T*+A*+T*+G | 5590 |
| 114 | A25292HI | CAGGTGCGGATGTCGTAT | +C*+A*+G*G*T*G*C*G*G*A*T*G*T*C*G*+T*+A*+T | 5589 |

TABLE 1-continued

List of human FoxP3-specific antisense oligonucleotides and a control oligonucleotide. An "H" after the antisense oligonucleotide ID indicates a human FoxP3-specific sequence that binds to the FoxP3 mRNA and/or an exonic region of the pre-mRNA, a "HM" after the antisense oligonucleotide ID indicates a human/mouse cross-reactive FoxP3 sequence that binds to an exonic region of the pre-mRNA and a "HI" after the antisense oligonucleotide ID indicates a human FoxP3-specific sequence that binds to an intronic region of the pre-mRNA. *refers to exon spanning oligonucleotides such as antisense oligonucleotides, position depicted in Table 1 indicates position on mRNA SEQ ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 231 | A25293HI | GAGCCGTATTTATTAGAG | +G*+A*+G*C*C*G*T*A*T*T*T*A*T*T*A*+G*+A*+G | 5569 |
| 232 | A25294HI | CAGCATGAGCCGTATTTA | +C*+A*+G*C*A*T*G*A*G*C*C*G*T*A*T*+T*+T*+A | 5563 |
| 233 | A25295HI | CGTGTAGTGCAAGGACCA | +C*+G*+T*G*T*A*G*T*G*C*A*A*G*G*A*+C*+C*+A | 4943 |
| 234 | A25296HI | CGACACTCGAGACCATAT | +C*+G*+A*C*A*C*T*C*G*A*G*A*C*C*A*+T*+A*+T | 4755 |
| 235 | A25297HI | GATGGCCGAATATAGTAG | +G*+A*+T*G*G*C*C*G*A*A*T*A*T*A*G*+T*+A*+G | 4677 |
| 236 | A25298HI | GCGGAGTAACTTGCACAC | +G*+C*+G*G*A*G*T*A*A*C*T*T*G*C*A*+C*+A*+C | 4470 |
| 237 | A25299HI | CACATTTGAGGCACGGCT | +C*+A*+C*A*T*T*T*G*A*G*G*C*A*C*G*+G*+C*+T | 4022 |
| 238 | A25300HI | GTGTGGCGCTAGGATGAA | +G*+T*+G*T*G*G*C*G*C*T*A*G*G*A*T*+G*+A*+A | 3605 |
| 239 | A25301HI | TTAGGTGTGGCGCTAGGA | +T*+T*+A*G*G*T*G*T*G*G*C*G*C*T*A*+G*+G*+A | 3601 |
| 115 | A25302HI | GGTTAGGTGTGGCGCTAG | +G*+G*+T*T*A*G*G*T*G*T*G*G*C*G*C*+T*+A*+G | 3599 |
| 240 | A25303HI | GGTTCGGTGTGGAGTGAG | +G*+G*+T*T*C*G*G*T*G*T*G*G*A*G*T*+G*+A*+G | 3415 |
| 241 | A25304HI | CGAGTATCTTACGTGTCA | +C*+G*+ A*G*T*A*T*C*T*T*A*C*G*T*G*+T*+C*+A | 3347 |
| 242 | A25305HI | TATCGAGTATCTTACGTG | +T*+A*+T*C*G*A*G*T*A*T*C*T*T*A*C*+G*+T*+G | 3344 |
| 116 | A25306HI | ATTATCGAGTATCTTACG | +A*+T*+T*A*T*C*G*A*G*T*A*T*C*T*T*+A*+C*+G | 3342 |
| 243 | A25307HI | TACCTGGCTGGAATCACGG | +T*+A*+C*C*T*G*G*C*T*G*G*A*A*T*C*A*+C*+G*+G | 15579 |
| 244 | A25308HI | CGTATCAATTGATGAATTC | +C*+G*+T*A*T*C*A*A*T*T*G*A*T*G*A*A*+T*+T*+C | 15478 |
| 245 | A25309HI | TAGCGACAGACAGATGGCG | +T*+A*+G*C*G*A*C*A*G*A*C*A*G*A*T*G*+G*+C*+G | 15247 |
| 246 | A25310HI | TAAACGCCAGCTGTGTACA | +T*+A*+A*A*C*G*C*C*A*G*C*T*G*T*G*T*+A*+C*+A | 15061 |
| 247 | A25311HI | ATTAAACGCCAGCTGTGTA | +A*+T*+T*A*A*A*C*G*C*C*A*G*C*T*G*T*+G*+T*+A | 15059 |
| 248 | A25312HI | CTCGGCGACATTACTATTA | +C*+T*+C*G*G*C*G*A*C*A*T*T*A*C*T*A*+T*+T*+A | 15041 |
| 249 | A25313HI | TAAAGGTCCTCGGCGACAT | +T*+A*+A*A*G*G*T*C*C*T*C*G*G*C*G*A*+C*+A*+T | 15033 |
| 250 | A25314HI | TCCTCTAAAGCGATACAAG | +T*+C*+C*T*C*T*A*A*A*G*C*G*A*T*A*C*+A*+A*+G | 14923 |
| 251 | A25315HI | CGGTTGACAATGGTGTGAA | +C*+G*+G*T*T*G*A*C*A*A*T*G*G*T*G*T*+G*+A*+A | 14875 |
| 252 | A25316HI | AGCTAAACTACGGTTGACA | +A*+G*+C*T*A*A*A*C*T*A*C*G*G*T*T*G*+A*+C*+A | 14865 |
| 253 | A25317HI | AATCGGCACTTGGTCAAAT | +A*+A*+T*C*G*G*C*A*C*TT*G*G*T*C*A*+A*+A*+T | 14542 |
| 254 | A25318HI | ACAATCGGCACTTGGTCAA | +A*+C*+A*A*T*C*G*G*C*A*C*T*T*G*G*T*+C*+A*+A | 14540 |
| 255 | A25319HI | CAACAATCGGCACTTGGTC | +C*+A*+A*C*A*A*T*C*G*G*C*A*C*T*T*G*+G*+T*+C | 14538 |
| 256 | A25320HI | AATAGTCAGTCCATTATCC | +A*+A*+T*A*G*T*C*A*G*T*C*C*A*T*T*A*+T*+C*+C | 13537 |
| 257 | A25321HI | GTGCGAGAGGAGGATTGCC | +G*+T*+G*C*G*A*G*A*G*G*A*G*G*A*T*T*+G*+C*+C | 13199 |
| 258 | A25322HI | GGTTAAGTCATTAGGTGTC | +G*+G*+T*T*A*A*G*T*C*A*T*T*A*G*G*T*+G*+T*+C | 13015 |
| 259 | A25323HI | CTTCTACGCTGTCTGGTTA | +C*+T*+T*C*T*A*C*G*C*T*G*T*C*T*G*G*+T*+T*+A | 13001 |
| 260 | A25324HI | CGTGGATCGTCCAACCTGT | +C*+G*+T*G*G*A*T*C*G*T*C*C*A*A*C*+T*+G*+T | 12720 |
| 261 | A25325HI | TCGTGGATCGTCCAACCTG | +T*+C*+G*T*G*G*A*T*C*G*T*C*C*A*A*C*+C*+T*+G | 12719 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 262 | A25326HI | ATCATCACCACGCTCTGGC | +A*+T*+C*A*T*C*A*C*C*A*C*G*C*T*C*T*+G*+G*+C | 12624 |
| 263 | A25327HI | CCTTCGCCAATACAGAGCC | +C*+C*+T*T*C*G*C*C*A*A*T*A*C*A*G*A*+G*+C*+C | 12510 |
| 264 | A25328HI | AGCCTTCGCCAATACAGAG | +A*+G*+C*C*T*T*C*G*C*C*A*A*T*A*C*A*+G*+A*+G | 12508 |
| 265 | A25329HI | CAGCCTTCGCCAATACAGA | +C*+A*+G*C*C*T*T*C*G*C*C*A*A*T*A*C*+A*+G*+A | 12507 |
| 266 | A25330HI | TCAGCCTTCGCCAATACAG | +T*+C*+A*G*C*C*T*T*C*G*C*C*A*A*T*A*+C*+A*+G | 12506 |
| 267 | A25331HI | ATAGTATAACACCAGGACC | +A*+T*+A*G*T*A*T*A*A*C*A*C*C*A*G*G*+A*+C*+C | 12142 |
| 268 | A25332HI | TTCATCGACACCACGGAGG | +T*+T*+C*A*T*C*G*A*C*A*C*C*A*C*G*G*+A*+G*+G | 11872 |
| 269 | A25333HI | GCTTCATCGACACCACGGA | +G*+C*+T*T*C*A*T*C*G*A*C*A*C*C*A*C*+G*+G*+A | 11870 |
| 270 | A25334HI | TTCCGCCATTGACGTCATG | +T*+T*+C*C*G*C*C*A*T*T*G*A*C*G*T*C*+A*+T*+G | 11834 |
| 271 | A25335HI | CAGATGCCGAGTTCCGTAG | +C*+A*+G*A*T*G*C*C*G*A*G*T*T*C*C*G*+T*+A*+G | 10817 |
| 272 | A25336HI | GCTCAGATGCCGAGTTCCG | +G*+C*+T*C*A*G*A*T*G*C*C*G*A*G*T*T*+c*+C*+G | 10814 |
| 273 | A25337HI | GATCATGCACGGATCCAGC | +G*+A*+T*C*A*T*G*C*A*C*G*G*A*T*C*C*+A*+G*+C | 10434 |
| 274 | A25338HI | TGATCATGCACGGATCCAG | +T*+G*+A*T*C*A*T*G*C*A*C*G*G*A*T*C*+C*+A*+G | 10433 |
| 275 | A25339HI | GTGTTTGCTCATCTTGCCG | +G*+T*+G*T*T*T*G*C*T*C*A*T*C*T*T*G*+C*+C*+G | 9950 |
| 276 | A25340HI | GATACTCGACCACCTGAGC | +G*+A*+T*A*C*T*C*G*A*C*C*A*C*C*T*G*+A*+G*+C | 9629 |
| 277 | A25341HI | TGAGATACTCGACCACCTG | +T*+G*+A*G*A*T*A*C*T*C*G*A*C*C*A*C*+C*+T*+G | 9626 |
| 278 | A25342HI | TATGAGATACTCGACCACC | +T*+A*+T*G*A*G*A*T*A*C*T*C*G*A*C*C*+A*+C*+C | 9624 |
| 279 | A25343HI | GTATGAGATACTCGACCAC | +G*+T*+A*T*G*A*G*A*T*A*C*T*C*G*A*C*+C*+A*+C | 9623 |
| 280 | A25344HI | GCGGTATGAGATACTCGAC | +G*+C*+G*G*T*A*T*G*A*G*A*T*A*C*T*C*+G*+A*+C | 9620 |
| 281 | A25345HI | AGTGCCACAGTAAAGGTCG | +A*+G*+T*G*C*C*A*C*A*G*T*A*A*A*G*G*+T*+C*+G | 9270 |
| 282 | A25346HI | TCATGGAGATCGAGTAACT | +T*+C*+A*T*G*G*A*G*A*T*C*G*A*G*T*A*+A*+C*+T | 8954 |
| 283 | A25347HI | ACGGCCATTCGCAGGTGCT | +A*+C*+G*G*C*C*A*T*T*C*G*C*A*G*G*T*+G*+C*+T | 8231 |
| 284 | A25348HI | AAGACGGCCATTCGCAGGT | +A*+A*+G*A*C*G*G*C*C*A*T*T*C*G*C*A*+G*+G*+T | 8228 |
| 285 | A25349HI | TTAAAGACGGCCATTCGCA | +T*+T*+A*A*A*G*A*C*G*G*C*C*A*T*T*C*+G*+C*+A | 8225 |
| 286 | A25350HI | AGCTTAAAGACGGCCATTC | +A*+G*+C*T*T*A*A*A*G*A*C*G*G*C*C*A*+T*+T*+C | 8222 |
| 287 | A25351HI | GAAGCTTAAAGACGGCCAT | +G*+A*+A*G*C*T*T*A*A*A*G*A*C*G*G*C*+C*+A*+T | 8220 |
| 288 | A25352HI | CGTGTGACCTATGTGGTTA | +C*+G*+T*G*T*G*A*C*C*T*A*T*G*T*G*G*+T*+T*+A | 5799 |
| 289 | A25353HI | TGTACATTCGCATCATGAG | +T*+G*+T*A*C*A*T*T*C*G*C*A*T*C*A*T*+G*+A*+G | 5716 |
| 290 | A25354HI | TCTGTACATTCGCATCATG | +T*+C*+T*G*T*A*C*A*T*T*C*G*C*A*T*C*+A*+T*+G | 5714 |
| 291 | A25355HI | TGAGCCGTATTTATTAGAG | +T*+G*+A*G*C*C*G*T*A*T*T*T*A*T*T*A*+G*+A*+G | 5568 |
| 292 | A25356HI | CAGCATGAGCCGTATTTAT | +C*+A*+G*C*A*T*G*A*G*C*C*G*T*A*T*T*+T*+A*+T | 5563 |
| 293 | A25357HI | ACAGCATGAGCCGTATTTA | +A*+C*+A*G*C*A*T*G*A*G*C*C*G*T*A*T*+T*+T*+A | 5562 |

TABLE 1-continued

List of human FoxP3-specific antisense oligonucleotides and a control
oligonucleotide. An "H" after the antisense oligonucleotide ID indicates a human FoxP3-
specific sequence that binds to the FoxP3 mRNA and/or an exonic region of the pre-
mRNA, a "HM" after the antisense oligonucleotide ID indicates a human/mouse cross-
reactive FoxP3 sequence that binds to an exonic region of the pre-mRNA and a "HI" after
the antisense oligonucleotide ID indicates a human FoxP3-specific sequence that binds
to an intronic region of the pre-mRNA. *refers to exon spanning oligonucleotides such as
antisense oligonucleotides, position depicted in Table 1 indicates position on mRNA SEQ
ID NO. 1 for exon spanning oligonucleotides.

| Seq ID | Name | Antisense Sequence 5'-3' | Antisense Sequence 5'-3' with PTO (*) and LNA (+) | position on pre-mRNA (GRCh38.p13 (GCF_000001405.39, Chr X (NC_000023.11) |
|---|---|---|---|---|
| 294 | A25358HI | CCGACACTCGAGACCATAT | +C*+C*+G*A*C*A*C*T*C*G*A*G*A*C*C*A*+T*+A*+T | 4754 |
| 295 | A25359HI | CGAATATAGTAGCTGGAGT | +C*+G*+A*A*T*A*T*A*G*T*A*G*C*T*G*G*+A*+G*+T | 4683 |
| 296 | A25360HI | TCTGATGGCCGAATATAGT | +T*+C*+T*G*A*T*G*G*C*C*G*A*A*T*A*T*+A*+G*+T | 4674 |
| 297 | A25361HI | AGTGGATAGGTGAGCTCGG | +A*+G*+T*G*G*A*T*A*G*G*T*G*A*G*C*T*+C*+G*+G | 4579 |
| 298 | A25362HI | GCGGAGTAACTTGCACACC | +G*+C*+G*G*A*G*T*A*A*C*T*T*G*C*A*C*+A*+C*+C | 4470 |
| 299 | A25363HI | CATTTGAGGCACGGCTTGG | +C*+A*+T*T*T*G*A*G*G*C*A*C*G*G*C*T*+T*+G*+G | 4024 |
| 300 | A25364HI | GTTTGGATTTGCGGACAGG | +G*+T*+T*T*G*G*A*T*T*T*G*C*G*G*A*C*+A*+G*+G | 3977 |
| 301 | A25365HI | TAGGTTTGGATTTGCGGAC | +T*+A*+G*G*T*TT*G*G*A*T*TT*G*C*G*+G*+A*+C | 3974 |
| 302 | A25366HI | GGCGCTAGGATGAAGGTTC | +G*+G*+C*G*C*T*A*G*G*A*T*G*A*A*G*G*+T*+T*+C | 3609 |
| 303 | A25367HI | GTGGCGCTAGGATGAAGGT | +G*+T*+G*G*C*G*C*T*A*G*G*A*T*G*A*A*+G*+G*+T | 3607 |
| 304 | A25368HI | GTGTGGCGCTAGGATGAAG | +G*+T*+G*T*G*G*C*G*C*T*A*G*G*A*T*G*+A*+A*+G | 3605 |
| 305 | A25369HI | TAGGTGTGGCGCTAGGATG | +T*+A*+G*G*T*G*T*G*G*C*G*C*T*A*G*G*+A*+T*+G | 3602 |
| 306 | A25370HI | GGTTAGGTGTGGCGCTAGG | +G*+G*+T*T*A*G*G*T*G*T*G*G*C*G*C*T*+A*+G*+G | 3599 |
| 307 | A25371HI | TTAGGTGGTTAGGCTCAGG | +T*+T*+A*G*G*T*G*G*T*T*A*G*G*C*T*C*+A*+G*+G | 3374 |
| 308 | A25372HI | GTTAGGTGGTTAGGCTCAG | +G*+T*+T*A*G*G*T*G*G*TT*A*G*G*C*T*+C*+A*+G | 3373 |
| 309 | A25373HI | CGAGTATCTTACGTGTCAG | +C*+G*+A*G*T*A*T*C*T*T*A*C*G*T*G*T*+C*+A*+G | 3347 |
| 322 | A25374HI | TCGAGTATCTTACGTGTCA | +T*+C*+G*A*G*T*A*T*C*T*T*A*C*G*T*G*+T*+C*+A | 3346 |
| 310 | A25375HI | ATTATCGAGTATCTTACGT | +A*+T*+T*A*T*C*G*A*G*T*A*T*C*T*T*A*+C*+G*+T | 3342 |
| 311 | A25376HI | ATGGTTTGAATTATCGAGT | +A*+T*+G*G*T*T**G*A*A*T*T*A*T*C*G*+A*+G*+T | 3333 |
| 312 | A25010H* | CTTGTCGGATGATGCCA | +C*+T*+T*G*T*C*G*G*A*T*G*A*T*G*+C*+C*+A | 1003 |
| 313 | A25024H* | GATGGCGTTCTTCCAGG | +G*+A*+T*G*G*C*G*T*T*C*T*T*C*C*+A*+G*+G | 1327 |
| 314 | A25119H* | CCGTTGAGAGCTGGTGCA | +C*+C*+G*T*T*G*A*G*A*G*C*T*G*G*T*+G*+C*+A | 496 |
| 315 | A25121H* | CCTTGTCGGATGATGCCA | +C*+C*+T*T*G*T*C*G*G*A*T*G*A*T*G*+C*+C*+A | 1003 |
| 316 | A25124H* | GATGGCGTTCTTCCAGGT | +G*+A*+T*G*G*C*G*T*T*C*T*T*C*C*A*+G*+G*+T | 1326 |
| 317 | A25137H* | CCGTTGAGAGCTGGTGCAT | +C*+C*+G*T*T*G*A*G*A*G*C*T*G*G*T*G*+C*+A*+T | 495 |
| 318 | A25203H* | CTTGTCGGATGATGCCAC | +C*+T*+T*G*T*C*G*G*A*T*G*A*T*G*C*+C*+A*+C | 1002 |
| 319 | A25222H* | CGTTGAGAGCTGGTGCATG | +C*+G*+TT*G*A*G*A*G*C*T*G*G*T*G*C*+A*+T*+G | 494 |
| 320 | A25226H* | TCGGATGATGC CACAGATG | +T*+C*+G*A*T*G*A*T*G*C*C*A*C*A*G*+A*+T*+G | 997 |
| 321 | A25236H* | GATGGCGTTCTTCCAGGTG | +G*+A*+T*G*G*C*G*T*T*C*T*T*C*C*A*G*+G*+T*+G | 1325 |
| 323 | Control oligo | | +C*+G*+T*T*T*A*G*G*C*T*A*T*G*T*A*+C*+T*+T | |

The oligonucleotides such as antisense oligonucleotides of the present invention hybridize for example with mRNA of human FoxP3 of SEQ ID NO. 1 and/or introns of the pre-mRNA of human FoxP3 of SEQ ID NO. 2. Such antisense oligonucleotides are called FoxP3 antisense oligonucleotides. The antisense oligonucleotides hybridize for example within a hybridizing active area which is one or more region(s) on the FoxP3 mRNA, e.g., of SEQ ID NO. 1 and/or the FoxP3 pre-mRNA, e.g., of SEQ ID NO. 2, where hybridization with an oligonucleotide highly likely results in a potent knockdown of the FoxP3 expression. In the present invention surprisingly several hybridizing active regions were identified for example selected from position 1510 to 2109, position 1510 to 1809, position 1810 to 2109, position 2410 to 2709, position 2710 to 3009, position 3310 to 3609, position 3610 to 3909, position 3910 to 4209, position 4210 to 4509, position 4510 to 4809, position 4810 to 5109, position 5110 to 5409, position 5410 to 5709, position 5710 to 6009, position 6610 to 6909, position 7810 to 8109, position 8110 to 8409, position 8710 to 9009, position 9010 to 9309, position 9610 to 9909, position 9910 to 10209, position 10210 to 10509, position 10810 to 11109, position 11410 to 11709, position 11710 to 12009, position 12010 to 12309, position 12310 to 12609, position 12610 to 12909, position 12910 to 13209, position 13510 to 13809, position 14410 to 14709, position 14710 to 15009, position 15010 to 15309, position 15310 to 15609, position 15610 to 15909 or a combination thereof (including the terminal figures of the ranges) of FoxP3 pre-mRNA for example of SEQ ID NO. 2. Antisense oligonucleotides hybridizing with these regions are indicated in the following Table 2:

| Region of SEQ ID NO. 2/ ASO name | First position on SEQ ID NO. 2 | SEQ ID NO. |
|---|---|---|
| Region 1510-1809 | | |
| A25028H | 1778 | 24 |
| A25029H | 1768 | 25 |
| A25030H | 1739 | 26 |
| A25069H | 1779 | 56 |
| A25070H | 1778 | 24 |
| A25071H | 1777 | 57 |
| A25072H | 1768 | 25 |
| A25073H | 1740 | 58 |
| A25074H | 1739 | 26 |
| A25075H | 1739 | 26 |
| A25076H | 1739 | 26 |
| A25077H | 1737 | 59 |
| A25078H | 1510 | 27 |
| A25096H | 1779 | 56 |
| A25097H | 1779 | 56 |
| A25098H | 1779 | 56 |
| A25099H | 1740 | 58 |
| A25100H | 1740 | 58 |
| A25101H | 1740 | 58 |
| A25102H | 1778 | 24 |
| A25103H | 1778 | 24 |
| A25104H | 1778 | 24 |
| A25106H | 1768 | 25 |
| A25107H | 1739 | 26 |
| A25108H | 1739 | 26 |
| A25109H | 1510 | 27 |
| A25110H | 1739 | 26 |
| A25111H | 1737 | 59 |
| A25128H | 1778 | 83 |
| A25129H | 1777 | 84 |
| A25130H | 1768 | 85 |
| A25131H | 1758 | 86 |
| A25132H | 1755 | 87 |
| A25133H | 1737 | 88 |

-continued

| Region of SEQ ID NO. 2/ ASO name | First position on SEQ ID NO. 2 | SEQ ID NO. |
|---|---|---|
| A25134H | 1735 | 89 |
| A25135H | 1513 | 90 |
| A25149H | 1758 | 102 |
| A25150H | 1739 | 103 |
| A25151H | 1738 | 104 |
| A25152H | 1737 | 105 |
| A25153H | 1737 | 105 |
| A25154H | 1737 | 105 |
| A25155H | 1737 | 105 |
| A25156H | 1733 | 106 |
| A25157H | 1733 | 106 |
| A25158H | 1513 | 107 |
| A25159H | 1510 | 108 |
| A25219H | 1514 | 167 |
| A25249H | 1778 | 194 |
| A25250H | 1777 | 195 |
| A25251H | 1769 | 196 |
| A25252H | 1762 | 197 |
| A25253H | 1759 | 198 |
| A25254H | 1757 | 199 |
| A25255H | 1756 | 200 |
| A25256H | 1755 | 201 |
| A25257H | 1755 | 201 |
| A25258H | 1736 | 202 |
| A25259H | 1579 | 203 |
| A25260H | 1576 | 204 |
| A25261H | 1514 | 205 |
| Region 1810-2109 | | |
| A25027H | 1820 | 23 |
| A25068H | 1820 | 23 |
| A25105H | 1820 | 23 |
| A25126H | 2069 | 81 |
| A25127H | 1966 | 82 |
| A25147H | 1822 | 101 |
| A25148H | 1822 | 101 |
| A25218H | 2068 | 166 |
| A25242H | 2068 | 187 |
| A25243H | 2067 | 188 |
| A25244H | 1967 | 189 |
| A25245H | 1966 | 190 |
| A25246H | 1821 | 191 |
| A25247H | 1820 | 192 |
| A25248H | 1814 | 193 |
| Region 2410-2709 | | |
| A25025H | 2526 | 21 |
| A25026H | 2455 | 22 |
| A25125H | 2455 | 80 |
| A25146H | 2444 | 100 |
| A25217H | 2526 | 165 |
| A25237H | 2529 | 182 |
| A25238H | 2520 | 183 |
| A25239H | 2456 | 184 |
| A25240H | 2455 | 185 |
| A25241H | 2441 | 186 |
| Region 2710-3009 | | |
| A25023H | 2780 | 20 |
| A25144H | 2791 | 98 |
| A25145H | 2790 | 99 |
| A25216H | 2790 | 164 |
| A25235H | 2772 | 181 |
| Region 3310-3609 | | |
| A25060HI | 3558 | 51 |
| A25061HI | 3431 | 52 |
| A25062HI | 3361 | 53 |
| A25063HI | 3361 | 54 |
| A25166HI | 3599 | 115 |
| A25167HI | 3342 | 116 |
| A25197HI | 3606 | 146 |
| A25198HI | 3415 | 147 |
| A25199HI | 3343 | 148 |

-continued

| Region of SEQ ID NO. 2/ ASO name | First position on SEQ ID NO. 2 | SEQ ID NO. |
|---|---|---|
| A25300HI | 3605 | 238 |
| A25301HI | 3601 | 239 |
| A25302HI | 3599 | 115 |
| A25303HI | 3415 | 240 |
| A25304HI | 3347 | 241 |
| A25305HI | 3344 | 242 |
| A25306HI | 3342 | 116 |
| A25366HI | 3609 | 302 |
| A25367HI | 3607 | 303 |
| A25368HI | 3605 | 304 |
| A25369HI | 3602 | 305 |
| A25370HI | 3599 | 306 |
| A25371HI | 3374 | 307 |
| A25372HI | 3373 | 308 |
| A25373HI | 3347 | 309 |
| A25374HI | 3346 | 322 |
| A25375HI | 3342 | 310 |
| A25376HI | 3333 | 311 |
| Region 3610-3909 | | |
| A25057HI | 3617 | 50 |
| A25095HI | 3616 | 75 |
| Region 3910-4209 | | |
| A25013H | 4205 | 10 |
| A25014H | 4200 | 11 |
| A25015H | 4199 | 12 |
| A25016H | 4199 | 13 |
| A25017H | 4198 | 14 |
| A25018H | 4198 | 15 |
| A25019H | 4198 | 16 |
| A25020H | 4197 | 17 |
| A25021H | 4197 | 18 |
| A25022H | 4192 | 19 |
| A25122H | 4206 | 78 |
| A25123H | 4199 | 79 |
| A25139H | 4206 | 93 |
| A25140H | 4205 | 94 |
| A25141H | 4204 | 95 |
| A25142H | 4203 | 96 |
| A25143H | 4202 | 97 |
| A25208H | 4205 | 156 |
| A25209H | 4204 | 157 |
| A25210H | 4202 | 158 |
| A25211H | 4201 | 159 |
| A25212H | 4198 | 160 |
| A25213H | 4197 | 161 |
| A25214H | 4196 | 162 |
| A25215H | 4195 | 163 |
| A25231H | 4201 | 177 |
| A25232H | 4199 | 178 |
| A25233H | 4198 | 179 |
| A25234H | 4196 | 180 |
| A25299HI | 4022 | 237 |
| A25363HI | 4024 | 299 |
| A25364HI | 3977 | 300 |
| A25365HI | 3974 | 301 |
| Region 4210-4509 | | |
| A25065H | 4225 | 55 |
| A25138H | 4228 | 92 |
| A25207H | 4227 | 155 |
| A25229H | 4255 | 175 |
| A25230H | 4250 | 176 |
| A25298HI | 4470 | 236 |
| A25362HI | 4470 | 298 |
| Region 4510-4809 | | |
| A25196HI | 4677 | 145 |
| A25296HI | 4755 | 234 |
| A25297HI | 4677 | 235 |
| A25358HI | 4754 | 294 |
| A25359HI | 4683 | 295 |

-continued

| Region of SEQ ID NO. 2/ ASO name | First position on SEQ ID NO. 2 | SEQ ID NO. |
|---|---|---|
| A25360HI | 4674 | 296 |
| A25361HI | 4579 | 297 |
| Region 4810-5109 | | |
| A25012H | 5101 | 9 |
| A25204H | 5102 | 152 |
| A25205H | 5094 | 153 |
| A25206H | 5019 | 154 |
| A25227H | 5103 | 173 |
| A25228H | 5019 | 174 |
| A25295HI | 4943 | 233 |
| Region 5110-5409 | | |
| A25011H | 5119 | 8 |
| Region 5410-5709 | | |
| A25053HI | 5608 | 47 |
| A25054HI | 5605 | 48 |
| A25055HI | 5604 | 49 |
| A25090HI | 5606 | 71 |
| A25091HI | 5607 | 72 |
| A25092HI | 5605 | 73 |
| A25093HI | 5603 | 74 |
| A25115H | 5604 | 49 |
| A25117H | 5605 | 73 |
| A25164HI | 5590 | 113 |
| A25165HI | 5589 | 114 |
| A25191HI | 5592 | 140 |
| A25192HI | 5590 | 140 |
| A25193HI | 5589 | 142 |
| A25194HI | 5588 | 143 |
| A25195HI | 5564 | 144 |
| A25290HI | 5591 | 230 |
| A25291HI | 5590 | 113 |
| A25292HI | 5589 | 114 |
| A25293HI | 5569 | 231 |
| A25294HI | 5563 | 232 |
| A25355HI | 5568 | 291 |
| A25356HI | 5563 | 292 |
| A25357HI | 5562 | 293 |
| Region 5710-6009 | | |
| A25190HI | 5717 | 139 |
| A25288HI | 5798 | 228 |
| A25289HI | 5717 | 229 |
| A25352HI | 5799 | 288 |
| A25353HI | 5716 | 289 |
| A25354HI | 5714 | 290 |
| Region 6610-6909 | | |
| A25005H | 6847 | 4 |
| A25006H | 6845 | 5 |
| A25008H | 6843 | 6 |
| A25009H | 6842 | 7 |
| A25120H | 6843 | 77 |
| A25201H | 6847 | 150 |
| A25202H | 6842 | 151 |
| A25225H | 6842 | 172 |
| Region 7810-8109 | | |
| A25004H | 7838 | 3 |
| A25200H | 7838 | 149 |
| A25223H | 7841 | 170 |
| A25224H | 7840 | 171 |
| Region 8110-8409 | | |
| A25050HI | 8247 | 44 |
| A25051HI | 8244 | 45 |
| A25052HI | 8243 | 46 |
| A25089HI | 8241 | 70 |
| A25163HI | 8224 | 112 |
| A25188HI | 8236 | 137 |
| A25189HI | 8227 | 138 |
| A25285HI | 8228 | 226 |

-continued

| Region of SEQ ID NO. 2/ ASO name | First position on SEQ ID NO. 2 | SEQ ID NO. |
|---|---|---|
| A25286HI | 8224 | 112 |
| A25287HI | 8223 | 227 |
| A25347HI | 8231 | 283 |
| A25348HI | 8228 | 284 |
| A25349HI | 8225 | 285 |
| A25350HI | 8222 | 286 |
| A25351HI | 8220 | 287 |
| Region 8710-9009 | | |
| A25346HI | 8954 | 282 |
| Region 9010-9309 | | |
| A25345HI | 9270 | 281 |
| Region 9610-9909 | | |
| A25048HI | 9645 | 42 |
| A25049HI | 9639 | 43 |
| A25186HI | 9630 | 135 |
| A25187HI | 9625 | 136 |
| A25284HI | 9623 | 225 |
| A25340HI | 9629 | 276 |
| A25341HI | 9626 | 277 |
| A25342HI | 9624 | 278 |
| A25343HI | 9623 | 279 |
| A25344HI | 9620 | 280 |
| Region 9910-10209 | | |
| A25047HI | 9995 | 41 |
| A25339HI | 9950 | 275 |
| Region 10210-10509 | | |
| A25046HI | 10450 | 40 |
| A25088HI | 10448 | 69 |
| A25185HI | 10257 | 134 |
| A25282HI | 10434 | 223 |
| A25283HI | 10001 | 224 |
| A25337HI | 10434 | 273 |
| A25338HI | 10433 | 274 |
| Region 10810-11109 | | |
| A25044HI | 10832 | 38 |
| A25045HI | 10838 | 39 |
| A25086HI | 10835 | 67 |
| A25087HI | 10834 | 68 |
| A25162HI | 10818 | 111 |
| A25281HI | 10818 | 111 |
| A25335HI | 10817 | 271 |
| A25336HI | 10814 | 272 |
| Region 11410-11709 | | |
| A251841HI | 11469 | 133 |
| Region 11710-12009 | | |
| A25038HMI | 11933 | 34 |
| A25039HI | 11886 | 35 |
| A25040HI | 11849 | 36 |
| A25041HI | 11938 | 37 |
| A25084HI | 11938 | 65 |
| A25085HMI | 11936 | 66 |
| A25112H | 11933 | 34 |
| A25113H | 11933 | 34 |
| A25114H | 11933 | 34 |
| A25116H | 11936 | 66 |
| A25177HI | 11926 | 126 |
| A25178HI | 11925 | 127 |
| A25179HI | 11923 | 128 |
| A25180HI | 11922 | 129 |
| A25181HI | 11918 | 130 |
| A25182HI | 11917 | 131 |
| A25183HI | 11916 | 132 |
| A25277HI | 11923 | 219 |
| A25278HI | 11922 | 220 |
| A25279HI | 11918 | 221 |
| A25280HI | 11916 | 222 |

-continued

| Region of SEQ ID NO. 2/ ASO name | First position on SEQ ID NO. 2 | SEQ ID NO. |
|---|---|---|
| A25332HI | 11872 | 268 |
| A25333HI | 11870 | 269 |
| A25334HI | 11834 | 270 |
| Region 12010-12309 | | |
| A25176HI | 12245 | 125 |
| A25331HI | 12142 | 267 |
| Region 12310-12609 | | |
| A25175HI | 12509 | 124 |
| A25275HI | 12511 | 217 |
| A25276HI | 12408 | 218 |
| A25327HI | 12510 | 263 |
| A25328HI | 12508 | 264 |
| A25329HI | 12507 | 265 |
| A25330HI | 12506 | 266 |
| Region 12610-12909 | | |
| A25036HI | 12736 | 32 |
| A25037HI | 12734 | 33 |
| A25161HI | 12720 | 110 |
| A25174HI | 12632 | 123 |
| A25272HI | 12720 | 110 |
| A25273HI | 12719 | 215 |
| A25274HI | 12633 | 216 |
| A25324HI | 12720 | 260 |
| A25325HI | 12719 | 261 |
| A25326HI | 12624 | 262 |
| Region 12910-1309 | | |
| A25173HI | 13198 | 122 |
| A25321HI | 13199 | 257 |
| A25322HI | 13015 | 258 |
| A25323HI | 13001 | 259 |
| Region 13510-13809 | | |
| A25320HI | 13537 | 256 |
| Region 14410-14709 | | |
| A25035HI | 14551 | 31 |
| A25172HI | 14539 | 121 |
| A25271HI | 14540 | 214 |
| A25317HI | 14542 | 253 |
| A25318HI | 14540 | 254 |
| A25319HI | 14538 | 255 |
| Region 14710-15009 | | |
| A25083HI | 14882 | 64 |
| A25170HI | 14919 | 119 |
| A25171HI | 14852 | 120 |
| A25268HI | 14924 | 211 |
| A25269HI | 14866 | 212 |
| A25270HI | 14865 | 213 |
| A25314HI | 14923 | 250 |
| A25315HI | 14875 | 251 |
| A25316HI | 14865 | 252 |
| Region 15010-15309 | | |
| A25032HI | 15174 | 28 |
| A25033HI | 15058 | 29 |
| A25034HI | 15055 | 30 |
| A25079HI | 15176 | 60 |
| A25080HI | 15173 | 61 |
| A25081HI | 15056 | 62 |
| A25082HI | 15056 | 63 |
| A25160HI | 15040 | 109 |
| A25168HI | 15154 | 117 |
| A25169HI | 15040 | 118 |
| A25262HI | 15244 | 206 |
| A25263HI | 15160 | 207 |
| A25264HI | 15157 | 208 |
| A25265HI | 15041 | 209 |
| A25266HI | 15040 | 109 |
| A25267HI | 15039 | 210 |

-continued

| Region of SEQ ID NO. 2/ ASO name | First position on SEQ ID NO. 2 | SEQ ID NO. |
|---|---|---|
| A25309HI | 15247 | 245 |
| A25310HI | 15061 | 246 |
| A25311HI | 15059 | 247 |
| A25312HI | 15041 | 248 |
| A25313HI | 15033 | 249 |
| Region 15310-15609 | | |
| A25307HI | 15579 | 243 |
| A25308HI | 15478 | 244 |
| Region 15610-15909 | | |
| A25118H | 15817 | 76 |
| A25136H | 15817 | 91 |
| A25220H | 15815 | 168 |
| A25221H | 15731 | 169 |

Table 2 shows some hybridizing active regions and antisense oligonucleotides hybridizing in this region.

Table 3 specifies exon spanning oligonucleotides such as antisense oligonucleotides hybridizing for example with FoxP3 mRNA of SEQ ID NO. 1:

| Region of SEQ ID NO. 1/ ASO name | First position on SEQ ID NO.1 | SEQ ID NO. |
|---|---|---|
| Exon spanning ASO | | |
| A25010H | 1003 | 312 |
| A25024H | 1327 | 313 |
| A25119H | 496 | 314 |
| A25121H | 1003 | 315 |
| A25124H | 1326 | 316 |
| A25137H | 495 | 317 |
| A25203H | 1002 | 318 |
| A25222H | 494 | 319 |
| A25226H | 997 | 320 |
| A25236H | 1325 | 321 |

The following Table 4 presents examples of oligonucleotides such as antisense oligonucleotides comprising modified nucleotides for example LNA which are indicated by (+) and phosphorothioate (PTO) indicated by (*). The antisense oligonucleotides consisting of or comprising the sequences of Table 4 may comprise any other modified nucleotide and/or any other combination of modified and unmodified nucleotides. Oligonucleotides of Table 4 hybridize with the mRNA of mouse FoxP3 (SEQ ID NO. 324; NM_001199347.1) or with intronic regions of the pre-mRNA of mouse FoxP3 (SEQ ID NO. 325; GRCm38.p6 (GCF_000001635.26, Chr X (NC_000086.7): 7,578,119-7,596,800), indicated by "I" in the following Table 4:

TABLE 4

List of mouse FoxP3-specific antisense oligonucleotides and a control oligonucleotide. An "M" after the antisense oligonucleotide ID indicates a mouse FoxP3-specific sequence that binds to an exonic region of the pre-mRNA, a "MR" after the antisense oligonucleotide ID indicates a mouse/rat cross-reactive FoxP3 sequence that binds to an exonic region of the pre-mRNA and a "MI" after the antisense oligonucleotide ID indicates a mouse FoxP3-specific sequence that binds to an intronic region of the pre-mRNA.

| Seq ID | Name | Antisense Sequence 5'-3' | Antisense Sequence 5'-3' with PTO (*) and LNA (+) |
|---|---|---|---|
| 526 | A25001M | GTCTCGTCTGAAGGCAG | +G*+T*C*T*C*G*T*C*T*G*A*A*G*G*+C*+A*+G |
| 527 | A25002MR | GGATAACGGCAGAGGAG | +G*+G*+A*T*A*A*C*G*G*C*A*G*A*G*+G*+A*+G |
| 528 | A25003M | TACTGGTGGCTACGATG | +T*+A*+C*T*G*G*T*G*G*C*T*A*C*G*+A*+T*+G |
| 329 | A25004M | TACTGGTGGCTACGAT | +T*+A*C*T*G*G*T*G*G*C*T*A*C*+G*+A*+T |
| 330 | A25005M | AAACAGGCCGCCGTCT | +A*+A*+A*C*A*G*G*C*C*G*C*C*G*T*+C*+T |
| 331 | A25006M | TGCAAACAGGCCGCCGT | +T*+G*+C*A*A*A*C*A*G*G*C*C*G*C*+C*+G*+T |
| 332 | A25007M | CACTGCAAACAGGCCGC | +C*+A*+C*T*G*C*A*A*A*C*A*G*G*C*+C*+G*+C |
| 333 | A25008M | TCGCATATTGTGGTACT | +T*+C*+G*C*A*T*A*T*T*G*T*G*G*T*+A*+C*+T |
| 334 | A25009M | GGTCGCATATTGTGGTA | +G*+G*+T*C*G*C*A*T*A*T*T*G*T*G*+G*+T*+A |
| 335 | A25010MR | GATTTCATTGAGTGTC C | +G*+A*T*T*T*C*A*T*T*G*A*G*T*G*T*+C*+ C |
| 336 | A25011M | GAACATGCGAGTAAAC C | +G*+A*+A*C*A*T*G*C*G*A*G*T*A*A*+A*+C*+C |
| 337 | A25012M | AGGCGAACATGCGAGTA | +A*+G*+G*C*G*A*A*C*A*T*G*C*G*A*+G*+T*+A |
| 338 | A25013M | TAGGCGAACATGCGAGT | +T*+A*+G*C*G*A*A*C*A*T*G*C*G*+A*+G*+T |
| 339 | A25014M | GTAGGCGAACATGCGAG | +G*+T*+A*G*G*C*G*A*A*C*A*T*G*C*+G*+A*+G |
| 340 | A25015M | GTAGGCGAACATGCGA | +G*+T*+A*G*G*C*G*A*A*C*A*T*G*+C*+G*+A |
| 341 | A25016M | AGTAGGCGAACATGCGA | +A*+G*+T*A*G*G*C*G*A*A*C*A*T*G*+C*+G*+A |

TABLE 4-continued

List of mouse FoxP3-specific antisense oligonucleotides and a control
oligonucleotide. An "M" after the antisense oligonucleotide ID indicates
a mouse FoxP3-specific sequence that binds to an exonic region of the
pre-mRNA, a "MR" after the antisense oligonucleotide ID indicates a
mouse/rat cross-reactive FoxP3 sequence that binds to an exonic region
of the pre-mRNA and a "MI" after the antisense oligonucleotide ID
indicates a mouse FoxP3-specific sequence that binds to an intronic
region of the pre-mRNA.

| Seq ID | Name | Antisense Sequence 5'-3' | Antisense Sequence 5'-3' with PTO (*) and LNA (+) |
|---|---|---|---|
| 342 | A25017M | TCGCTCTCCACTCGCAC | +T*+C*+G*C*T*C*T*C*C*A*C*T*C*G*+C*+A*+C |
| 343 | A25018MR | TCATCTACGGTCCACAC | +T*+C*+A*+T*C*T*A*C*G*G*T*C*C*A*+C*+A*+C |
| 344 | A25019MR | ATTCATCTACGGTCCAC | +A*+T*+T*C*A*T*C*T*A*C*G*G*T*C*+C*+A*+C |
| 345 | A25020M | CGTAGGACTTGCCTCCT | +C*+G*T*A*G*G*A*C*T*T*G*C*C*T*C*+C*+T |
| 346 | A25021M | TACACGTAGGACTTGCC | +T*+A*+C*A*C*G*T*A*G*G*A*C*T*T*+G*+C*+C |
| 347 | A25022M | ATAGGTACACGTAGGAC | +A*+T*+A*G*G*T*A*C*A*C*G*T*A*G*+G*+A*+C |
| 348 | A25023M | TAGCAGGCACATCATCG | +T*+A*+G*C*A*G*G*C*A*C*A*T*C*A*+T*+C*+G |
| 349 | A25024M | TTCACGAATGTACCAAG | +T*+T*+C*A*C*G*A*A*T*G*T*A*C*C*+A*+A*+G |
| 350 | A25025MR | GATCAGTTATGCCTGTG | +G*+A*+T*C*A*G*T*T*A*T*G*C*C*T*+G*+T*+G |
| 351 | A25026M | CTTGAGGCTGCGTATGA | +C*+T*+T*G*A*G*G*C*T*G*C*G*T*A*+T*+G*+A |
| 352 | A25027M | TTGCTTGAGGCTGCGTA | +T*+T*+G*C*TT*G*A*G*G*C*T*G*C*+G*+T*+A |
| 353 | A25028M | ATTGCTTGAGGCTGCGT | +A*+T*+T*G*C*TT*G*A*G*G*C*T*G*C*+G*+T |
| 354 | A25029M | TTGGAGAGTCGGTGTGT | +T*+T*+G*G*A*G*A*G*T*C*G*G*T*G*+T*+G*+T |
| 355 | A25030M | TACATCTTGGAGAGTCG | +T*+A*+C*A*T*C*T*T*G*G*A*G*A*G*+T*+C*+G |
| 356 | A25031MR | ACGCTTAGGCATGGATT | +A*+C*+G*C*T*T*A*G*G*C*A*T*G*G*+A*+T*+T |
| 357 | A25032M | TTCATTTGGTATCCGCT | +T*+T*+C*A*T*T*T*G*G*T*A*T*C*C*+G*+C+T |
| 358 | A25033MR | GTGAGGACTACCGAGCC | +G*+T*+G*A*G*G*A*C*T*A*C*C*G*A*+G*+C*+C |
| 359 | A25034MR | ATCTGTGAGGACTACCG | +A*+T*+C*T*G*T*G*A*G*G*A*C*T*A*+C*+C*+G |
| 360 | A25035M | TGTTTTGCGCTGAGAGT | +T*+G*+T*T*T*T*G*C*G*C*T*G*A*G*+A*+G*+T |
| 361 | A25036M | TTCGGAAAGCCTACAAG | +T*+T*+C*G*G*A*A*A*G*C*C*T*A*C*+A*+A*+G |
| 362 | A25037MR | CTGTTCGGAAAGCCTAC | +C*+T*+G*T*T*C*G*G*A*A*A*G*C*C*+T*+A*+C |
| 363 | A25038MR | AAGGATGATGCTGTTCG | +A*+A*+G*G*A*T*G*A*T*G*C*T*G*T*+T*+C*+G |
| 364 | A25039M | CTCGACCGGACATTTGC | +C*+T*+C*G*A*C*C*G*G*A*C*A*T*T*+T*+G*+C |
| 365 | A25040M | CTCGACCGGACATTTG | +C*+T*+C*G*A*C*C*G*G*A*C*A*T*+T*+T*+G |
| 366 | A25041M | GCTCGACCGGACATTT | +G*+C*+T*C*G*A*C*C*G*G*A*C*A*+T*+T*+T |
| 367 | A25042M | AGCTCGACCGGACATTT | +A*+G*+C*T*C*G*A*C*C*G*G*A*C*A*+T*+T*+T |
| 368 | A25043M | GGAAGCTCGACCGGACA | +G*+G*+A*A*G*C*T*C*G*A*C*C*G*G*+A*+C*+A |
| 369 | A25044M | ATCTTGTCGGACACAAA | +A*+T*+C*T*T*G*T*C*G*G*A*C*A*C*+A*+A*+A |
| 370 | A25045M | AGATCTTGTCGGACACA | +A*+G*+A*T*C*T*T*G*T*C*G*G*A*C*+A*+C*+A |
| 371 | A25046MI | CCGTGATGCGATGAGC | +C*+C*+G*T*G*A*T*G*C*G*A*T*G*+A*+G*+C |
| 372 | A25047MI | GGAGCTATATAGCCGTA | +G*+G*+A*G*C*T*A*T*A*T*A*G*C*C*+G*+T*+A |
| 373 | A25048MI | TGGTCCGCTAGGACTTC | +T*+G*G*T*C*C*G*C*T*A*G*G*A*C*T*+T*+C |
| 374 | A25049MI | CATCGTTACTAGTGTTC | +C*+A*+T*C*G*T*T*A*C*T*A*G*T*G*+T*+T*+C |
| 375 | A25050MI | TCTTGCAAAGTTCGTAC | +T*+C*+T*T*G*C*A*A*A*G*T*T*C*G*+T*+A*+C |

TABLE 4-continued

List of mouse FoxP3-specific antisense oligonucleotides and a control
oligonucleotide. An "M" after the antisense oligonucleotide ID indicates
a mouse FoxP3-specific sequence that binds to an exonic region of the
pre-mRNA, a "MR" after the antisense oligonucleotide ID indicates a
mouse/rat cross-reactive FoxP3 sequence that binds to an exonic region
of the pre-mRNA and a "MI" after the antisense oligonucleotide ID
indicates a mouse FoxP3-specific sequence that binds to an intronic
region of the pre-mRNA.

| Seq ID | Name | Antisense Sequence 5'-3' | Antisense Sequence 5'-3' with PTO (*) and LNA (+) |
|---|---|---|---|
| 376 | A25051MI | CCAAGTTCTATCGATTC | +C*+C*+A*A*G*T*T*C*T*A*T*C*G*A*+T*+T*+C |
| 377 | A25052MI | AGTCTATCCTGTAGCCG | +A*+G*+T*C*T*A*T*C*C*T*G*T*A*G*+C*+C*+G |
| 378 | A25053MHI | CCACAGGTTTCGTTCCG | +C*+C*+*A*C*A*G*G*T*T*T*C*G*T*T*+C*+C*+G |
| 379 | 125054MRHI | GTCATGGCGGCCGGATG | +G*+T*C*A*T*G*G*C*G*G*C*C*G*G*+A*+T*+G |
| 380 | A25055MI | ACTATATTGGCTTAACC | +A*+C*+T*A*T*A*T*T*G*G*C*T*T*A*+A*+C*+C |
| 381 | A25056MI | CCGTGATGCGATGAGCT | +C*+C*+G*T*G*A*T*G*C*G*A*T*G*A*+G*+C*+T |
| 382 | A25057MI | AAGACTAGTGTGTCACG | +A*+A*+G*A*C*T*A*G*T*G*T*G*T*C*+A*+C*+G |
| 383 | A25058MI | CCGTTCTACTATATACT | +C*+C*+G*T*T*C*T*A*C*T*A*T*A*T*+A*+C*+T |
| 384 | A25059MI | ATAGTGAGGCGAGTGGT | +A*+T*+A*G*T*G*A*G*G*C*G*A*G*T*+G*+G*+T |
| 385 | A25060MI | TACCACTCTGTCGTGAA | +T*+A*+C*C*A*C*T*C*T*G*T*C*G*T*+G*+A*+A |
| 386 | A25061MI | CACACGGTAGCAACAAT | +C*+A*+C*A*C*G*G*T*A*G*C*A*A*C*+A*+A*+T |
| 387 | A25062MI | TGCTCCGATTCCATACC | +T*+G*+C*T*C*C*G*A*T*T*C*C*A*T*+A*+C*+C |
| 388 | A25063MI | GGTTGGAGTTTCCGTGA | +G*+G*+T*T*G*G*A*G*TT*T*C*C*G*+T*+G*+A |
| 389 | A25064MI | GACTGATAATAGCGATT | +G*+A*+C*T*G*A*T*A*A*T*A*G*C*G*+A*+T*+T |
| 390 | A25065MI | TACATGCGAGGTAAACT | +T*+A*+C*A*T*G*C*G*A*G*G*T*A*A*+A*+C*+T |
| 391 | A25066MI | TTAGATCCTTCTGCGTG | +T*+T*+A*G*A*T*C*C*T*T*C*T*G*C*+G*+T*+G |
| 392 | A25067MI | CTGGCCACGCAAACACG | +C*+T*+G*G*C*C*A*C*G*C*A*A*A*C*+A*+C*+G |
| 393 | A25068MI | ACGTTAGACAGGAGGTA | +A*+C*+G*TT*A*G*A*C*A*G*G*A*G*+G*+T*+A |
| 394 | A25069MI | GTAAGCAGAGTAGGCGT | +G*+T*+A*A*G*C*A*G*A*G*T*A*G*G*+C*+G*+T |
| 395 | A25070MI | GGTAATCGAGACACTTA | +G*+G*+T*A*A*T*C*G*A*G*A*C*A*C*+T*+T*+A |
| 396 | control oligo | | +C*+G*+T*T*T*A*G*G*C*T*A*T*G*T*A*+C*+T*+T |

The oligonucleotide such as an antisense oligonucleotide of the present invention inhibits for example 40% to 99%, 50% to 98%, 60% to 95%, 70% to 90% or at least about 40%, 50%, 55%, 60%, 65%, 70%, 75%, 80%, 85%, 90%, 92%, 94%, 95%, 96%, 97%, 98%, 99% or 100% of FoxP3 expression (mRNA and/or pre-mRNA) such as the, e.g., human, rat or mouse, FoxP3 expression, e.g., within 6 to 240 h, 12 to 216 h, 18 to 120 h or 24 to 72 h, or 12 h, 24 h, 36 h, 48 h, 60 h, 72 h, 84 h, 96 h, 108 h, 120 h, 132 h, 144 h, 156 h, 168 h, 180 h, 192 h, 204 h, 216 h, 228 h or 240 h, preferably 24 to 72 h, e.g., compared to an untreated control. The untreated control is for example FoxP3, FoxP3 mRNA, FoxP3 pre-mRNA expression or a combination thereof in a subject before an oligonucleotide of the present invention is administered or an untreated sample such as a cell, blood, urine, saliva etc.

The oligonucleotides of the present invention are for example active and inhibit expression for example in a cell, tissue, organ, or a subject. The oligonucleotide such as an antisense oligonucleotide of the present invention inhibits the expression of FoxP3 for example at a nanomolar or micromolar concentration for example in a concentration of 0.1, 1, 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900 or 950 nM, or 1, 10 or 100 μM.

The oligonucleotide of the present invention is for example used in a concentration of 1 to 100 nM, 5 to 90 nM, 10 to 80 nM, 15 to 70 nM, 20 to 60 nM, 25 to 50 nM, 30 to 45 nM or 3, 5, 9, 10, 15, 27, 30, 40, 50, 75, 82, 100, 250, 300, 500, or 740 nM, or 1 to 50 μM, 3 to 40 μM, 5 to 30 μM, 8 to 25 μM, 10 μM to 15 μM, or 6 μM, 1.5 μM, 375 nM, 94 nM, 24 nM, 6 nM, or 1.5 nM.

The oligonucleotide such as an antisense oligonucleotide of the present invention is administered to a cell, tissue, organ or subject one or more times a day, one or more times a week, one or more times a month or one or more times a year.

In some embodiments the present invention refers to a pharmaceutical composition comprising an oligonucleotide of the present invention and a pharmaceutically acceptable carrier, excipient and/or diluent. The pharmaceutical composition further comprises for example a chemotherapeutic, another disease specific active agent, another oligonucleotide, an antibody, a carbohydrate-modified antibody, a peptide-based therapeutic, a protein-based therapeutic, a therapeutic vaccine, a HERA fusion protein, a ligand trap, a Fab fragment, a nanobody, a BiTe®, a DARPin® and/or a small molecule which is for example effective in tumor treatment, or chronic inflammation, e.g., associated with chronic infections.

In some embodiments, the oligonucleotide such as an antisense oligonucleotide or the pharmaceutical composition of the present invention is for use in a method of preventing and/or treating a disorder. The use of the oligonucleotide or the pharmaceutical composition of the present invention for example in a method of preventing and/or treating a disorder is combined with radiotherapy. The radiotherapy may be further combined with a chemotherapy (e.g., platinum, gemcitabine). The disorder is for example characterized by a FoxP3 imbalance, i.e., the FoxP3 level for example is increased in comparison to the level in a normal, healthy cell, tissue, organ or subject. Alternatively or in addition, FoxP3 expression for example is involved in the induction and/or maintenance of the disease and/or mediates resistance to another therapy. The FoxP3 level is for example increased by an increased FoxP3 expression and functionality, respectively. The FoxP3 level can be measured by any standard method such as immunohistochemistry, flow cytometry, western blot, quantitative real time PCR, HPLC, UHPLC, FPLC or QuantiGene® assay known to a person skilled in the art.

An oligonucleotide such as an antisense oligonucleotide or a pharmaceutical composition of the present invention is for example administered locally or systemically for example orally, sublingually, nasally, inhaled, subcutaneously, intravenously, intraperitoneally, intramuscularly, intratumorally, intrathecally, transdermally, and/or rectally. Alternatively or in combination an immune cell ex vivo treated with an oligonucleotide such as an oligonucleotide of the present invention is administered. In another alternative an oligonucleotide of the present invention is used in a cell therapy method and for example administered in combination with CAR-T cells, transgenic TCR-T cells or ex vivo expanded TILs. The oligonucleotide such as an antisense oligonucleotide of the present invention is administered alone or in combination with another oligonucleotide of the present invention and optionally in combination with another compound such as a chemotherapeutic (e.g., platinum, gemcitabine), another disease specific agent, another oligonucleotide (e.g., an oligonucleotide not being part of the present invention), an antibody, a carbohydrate-modified antibody, a peptide-based therapeutic, a protein-based therapeutic, a therapeutic vaccine, a HERA fusion protein, a ligand trap, a Fab fragment, a nanobody, a BiTe®, a DARPin® and/or a small molecule. The other compound such as a chemotherapeutic, another disease specific agent, another oligonucleotide (i.e., not being part of the present invention), the antibody, a carbohydrate-modified antibody, a peptide-based therapeutic, a protein-based therapeutic, a therapeutic vaccine a HERA fusion protein, a ligand trap, a Fab fragment, a nanobody, a BiTe®, a DARPin® and/or the small molecule are for example effective in preventing and/or treating a malignant and/or benign tumor, a chronic infection, a chronic inflammatory disease or a combination thereof.

An oligonucleotide such as an antisense oligonucleotide or a pharmaceutical composition of the present invention is for example for use in a method of preventing and/or treating a chronic inflammatory disease, a chronic infection, a malignant and/or benign tumor or a combination thereof. Examples of tumors preventable and/or treatable by use of the oligonucleotide or pharmaceutical composition of the present invention are breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteosarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomata tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythemia vera, adenocarcinoma, anaplastic astrocytoma, glioblastoma multiforme, leukemia, epidermoid carcinoma and a combination thereof.

An oligonucleotide such as an antisense oligonucleotide or a pharmaceutical composition of the present invention is for example for use in a method of preventing and/or treating a chronic infectious disease, wherein the chronic infectious disease is for example selected from the group consisting of hepatitis B and C virus, human immune deficiency virus, cytomegalovirus, Herpes Simplex virus, Measles virus, respiratory syncytial virus, *Helicobacter pylori* infection or a combination thereof.

An oligonucleotide such as an antisense oligonucleotide or a pharmaceutical composition of the present invention is for example for use in a method of preventing and/or treating a chronic inflammatory disease caused by infection, wherein the chronic inflammatory disease caused by infection is for example selected from the group consisting of chronic inflammatory diseases of the liver such as liver fibrosis, liver cirrhosis or a combination thereof.

In some embodiments two or more oligonucleotides of the present invention are administered together, at the same time point for example in a pharmaceutical composition or separately, or on staggered intervals for example as a pharmaceutical composition. Alternatively or in addition, one or more oligonucleotides of the present invention are administered together with another compound such as a chemotherapeutic, a disease specific agent, another oligonucleotide (i.e., not being part of the present invention), an antibody, a carbohydrate-modified antibody, a peptide-based therapeutic, a protein-based therapeutic, a therapeutic vaccine, a HERA fusion protein, a ligand trap, a Fab fragment, a nanobody, a BiTe®, a DARPin® and/or a small molecule, at the same time point for example in a pharmaceutical composition or separately, or on staggered intervals.

The oligonucleotide such as an antisense oligonucleotide of the present invention inhibits for example the expression and functionality, respectively, of FoxP3 and an antitumor active agent such as a chemotherapeutic, a disease specific agent, another oligonucleotide (i.e., not being part of the present invention), an antibody, a carbohydrate-modified antibody, a peptide-based therapeutic, a protein-based therapeutic, a therapeutic vaccine, a HERA fusion protein, a ligand trap, a Fab fragment, a nanobody, a BiTe®, a DAR-Pin® and/or small molecule inhibits (antagonist) an immune suppressive factor and/or stimulates (agonist) an immune stimulatory factor or inhibits another target that is involved in cancer progression and/or metastasis directly and/or indirectly. The immune suppressive factor is for example selected from the group consisting of IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, MTDH, Xbp1, Chop and a combination thereof. The immune stimulatory factor is for example selected from the group consisting of 4-1BB, Ox40, KIR, GITR, CD27, 2B4 and a combination thereof. The factor involved in cancer progression and/or metastasis is for example selected from the group consisting of SND1, MTDH, HER-2, BRAF, KRAS, VEGF, EGFR1, EGFR2, BCR/ABL, ABL, MET, ALK, JAK2, BTK, miR-223, CCL18, CCL20, Lcn2, CCL5/CCR9, DDR2, PHD2, IL6, SDF-1/CXCL12 and a combination thereof. An antisense oligonucleotide or a pharmaceutical composition of the present invention is for example combined with or comprises a therapeutic vaccine. In such combination the antisense oligonucleotide and the therapeutic vaccine are administered together or separately for example at the same time or at different times.

The immune suppressive factor is a factor whose expression and/or activity is for example decreased or increased in a cell, tissue, organ or subject. The immune stimulatory factor is a factor whose expression and/or activity is for example increased or decreased in a cell, tissue, organ or subject depending on the cell, tissue, organ or subject and its individual conditions. The factor involved in cancer progression and/or metastasis is a factor whose expression and/or activity is for example increased or decreased in a cell, tissue, organ or subject depending on the cell, tissue, organ or subject and its individual conditions in comparison to a healthy subject or is for example involved in the induction and/or maintenance of the disease and/or mediates resistance to another therapy.

The antisense oligonucleotide or pharmaceutical composition inhibiting the expression and/or functionality of FoxP3 results for example in an increase of the expression of a pro-inflammatory gene such as IL2 and/or IFNγ and/or Granzyme B and/or wherein the inhibition of FoxP3 results in a decrease of the expression of an immunosuppressive gene such as CD25, CD39, CD73, NRP1, TGF-beta, GARP, CCR4, Ctla4, and/or Tnfrsf18.

An antibody in combination with the oligonucleotide or the pharmaceutical composition of the present invention is for example an anti-PD-1 antibody, an anti-PD-L1 antibody, or a bispecific antibody. A small molecule in combination with the oligonucleotide such as an antisense oligonucleotide or the pharmaceutical composition of the present invention are for example Sunitinib, Alectinib, Afatinib, Ibrutinib, Imatinib, Lenvatinib, Sorafenib, or Epacadostat. A chemotherapy in combination with the oligonucleotide or the pharmaceutical composition of the present invention is for example platinum or gemcitabine.

Moreover, one or more oligonucleotides such as antisense oligonucleotides of the present invention are used in determining the status of a cancer disease.

A subject of the present invention is for example a mammalian such as a human, dog, cat, horse, cow, pig etc., a bird or a fish.

46

EXAMPLES

The following examples illustrate different embodiments of the present invention, but the invention is not limited to these examples. The following experiments are performed on cells endogenously expressing FoxP3, i.e., the cells do not represent an artificial system comprising transfected reporter constructs. Such artificial systems generally show a higher degree of inhibition and lower $IC_{50}$ values than endogenous systems which are closer to therapeutically relevant in vivo systems. Further, in the following experiments no transfecting agent is used, i.e., gymnotic delivery is performed. Transfecting agents are known to increase the activity of an oligonucleotide which influences the $IC_{50}$ value (see for example Zhang et al., Gene Therapy, 2011, 18, 326-333; Stanton et al., Nucleic Acid Therapeutics, Vol. 22, No. 5, 2012). As artificial systems using a transfecting agent are hardly or impossible to translate into therapeutic approaches and no transfection formulation has been approved so far for oligonucleotides, the following experiments are performed without any transfecting agent.

Example 1: Design of Human FoxP3-Specific Antisense Oligonucleotides (ASOs)

For the design of ASOs with specificity for exonic regions within the human FoxP3 gene the FoxP3 mRNA sequence with the RefSeq ID NM_014009.3 was used. For ASOs with specificity for intronic regions within the human FoxP3 gene the FoxP3 pre-mRNA sequence (GRCh38.p13 (GCF_000001405.39, Chr X (NC_000023.11): 49,249, 986K-49,226,382-pre-mRNA positions as annotated in FASTA format (visible range) downloaded from ncbi.nlm-.nih.gov/genome/gdv/browser/?context=genome&acc-GCF_000001405.39) was used. An "H" after the ASO ID indicates a human FoxP3-specific sequence that binds to an exonic region of the pre-mRNA, a "HM" after the ASO ID indicates a human/mouse cross-reactive FoxP3 sequence that binds to an exonic region of the pre-mRNA and a "HI" after the ASO ID indicates a human FoxP3-specific sequence that binds to an intronic region of the pre-mRNA. 15, 16, 17, 18 and 19 mers for example were designed according to in house criteria, neg1 (described in WO2014154843 A1) was used as control oligonucleotide in all experiments. Examples of oligonucleotides such as antisense oligonucleotides are shown in Table 1.

Figure 1A:
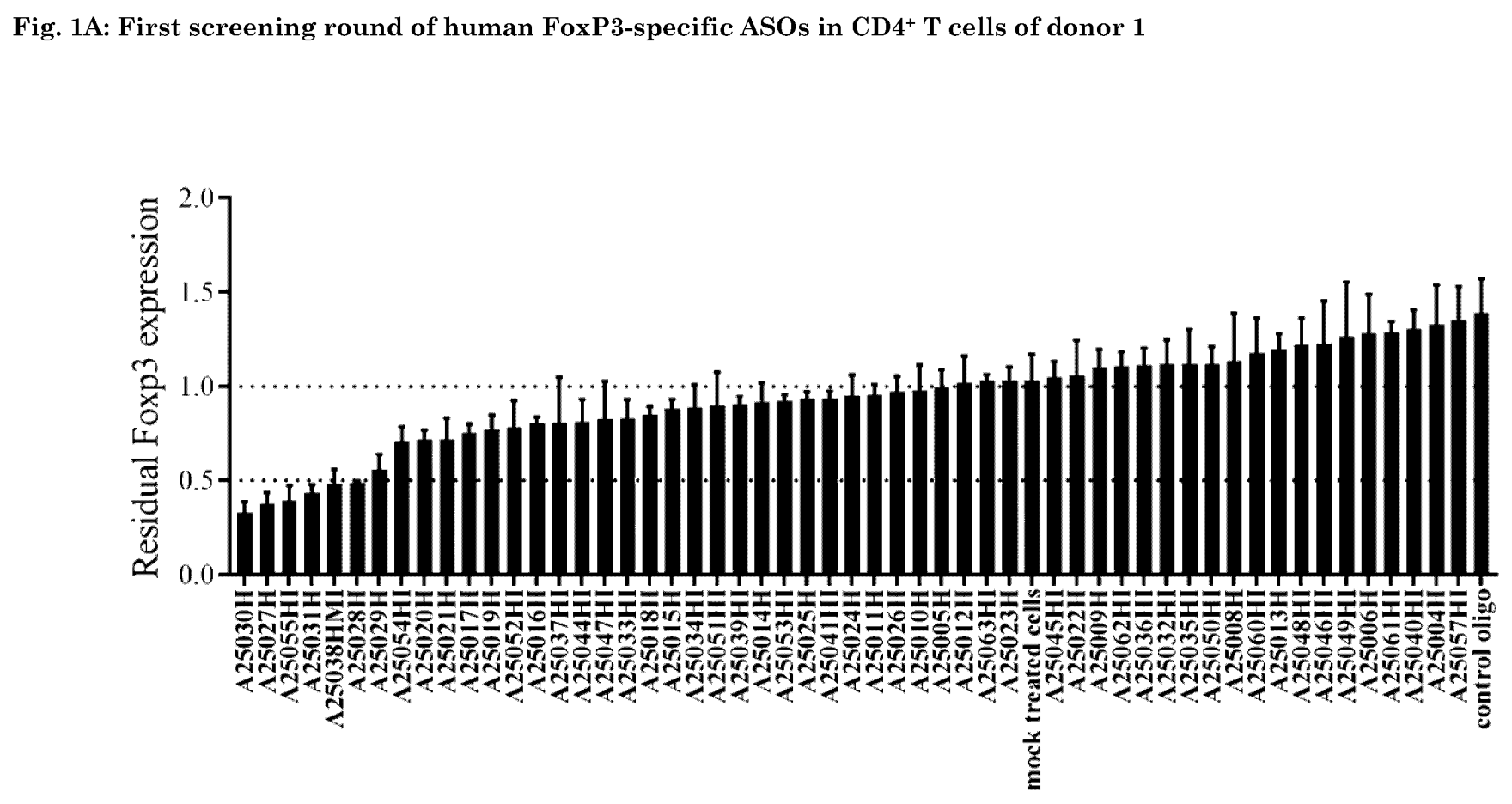

Example 2: Target Knockdown Efficacy Screens of Human FoxP3-Specific ASOs in T Cells in a 1$^{st}$ Screening Round In order to investigate the knockdown efficacy of the in silico designed FoxP3 ASOs, two efficacy screening rounds were performed in human CD4$^+$ T cells. Therefore, cells were treated with the respective ASO at a concentration of 5 μM for three days without the addition of a transfection reagent. In addition cells were treated with TGF-beta, ATRA, IL-2 and stimulated with CD3/CD28 beads (ThermoFisher) in order to increase expression levels of FoxP3. Cells were lyzed after the three days treatment period, FoxP3 and HPRT1 mRNA expression was analyzed using the QuantiGene® Singleplex assay (ThermoFisher) and the FoxP3 expression values were normalized to HPRT1 values. The results for the first screening round of ASOs are shown in FIGS. 1A and 1B as well as Tables 5 and 6. As depicted in FIG. 1A and Table 5, treatment of CD4$^+$ T cells with the ASOs A25030H (SEQ ID NO. 26), A25027H (SEQ ID NO.

23), A25055HI (SEQ ID NO. 49), A25031H (SEQ ID NO. 27), A25038HMI (SEQ ID NO. 34), and A25028H (SEQ ID NO. 24), resulted in a target inhibition of >50% (represented by a residual FoxP3 mRNA expression of <0.5 as compared to mock treated cells). Knockdown efficacy of FoxP3-specific ASOs was furthermore tested in CD4+ T cells from another donor. As shown in FIG. 1B and Table 6, treatment with the ASOs A25030H (SEQ ID NO. 26), A25055HI (SEQ ID NO. 49), A25031H (SEQ ID NO. 27), A25027H (SEQ ID NO. 23), A25038HMI (SEQ ID NO. 34), A25028H (SEQ ID NO. 24) and A25054HI (SEQ ID NO. 48) resulted in a target inhibition of >50% (represented by a residual FoxP3 mRNA expression of <0.5 as compared to mock treated cells). The control oligo did not result in an inhibition of FoxP3 expression in CD4+ T cells from both donors.

TABLE 5

List of the mean FoxP3 mRNA expression values in ASO-treated CD4+ T cells from donor 1 compared to mock treated cells in first screening round. Expression values are normalized to HPRT1.

| ASO | Residual FoxP3 expression (compared to mock treated cells) | ASO | Residual FoxP3 expression (compared to mock treated cells) |
|---|---|---|---|
| A25030H | 0.33 | A25011H | 0.96 |
| A25027H | 0.38 | A25026H | 0.97 |
| A25055HI | 0.39 | A25010H | 0.98 |
| A25031H | 0.44 | A25005H | 1 |
| A25038HMI | 0.48 | A25012H | 1.02 |
| A25028H | 0.49 | A25063HI | 1.03 |
| A25029H | 0.56 | A25023H | 1.03 |
| A25054HI | 0.71 | A25045HI | 1.05 |
| A25020H | 0.72 | A25022H | 1.06 |
| A25021H | 0.72 | A25009H | 1.1 |
| A25017H | 0.75 | A25062HI | 1.11 |
| A25019H | 0.77 | A25036HI | 1.11 |
| A25052HI | 0.78 | A25032HI | 1.12 |
| A25016H | 0.8 | A25035HI | 1.12 |
| A25037HI | 0.81 | A25050HI | 1.12 |
| A25044HI | 0.81 | A25008H | 1.13 |
| A25047HI | 0.83 | A25060HI | 1.18 |
| A25033HI | 0.83 | A25013H | 1.2 |
| A25018H | 0.85 | A25048HI | 1.22 |
| A25015H | 0.88 | A25046HI | 1.23 |
| A25034HI | 0.89 | A25049HI | 1.26 |
| A25051HI | 0.9 | A25006H | 1.29 |
| A25039HI | 0.91 | A25061HI | 1.29 |
| A25014H | 0.92 | A25040HI | 1.3 |
| A25053HI | 0.92 | A25004H | 1.33 |
| A25025H | 0.93 | A25057HI | 1.35 |
| A25041HI | 0.93 | mock treated cells | 1.03 |
| A25024H | 0.95 | control oligo | 1.42 |

TABLE 6

List of the mean FoxP3 mRNA expression values in ASO-treated CD4+ T cells from donor 2 compared to mock treated cells in first screening round. Expression values are normalized to HPRT1.

| ASO | Residual FoxP3 expression (compared to mock treated cells) | ASO | Residual FoxP3 expression (compared to mock treated cells) |
|---|---|---|---|
| A25030H | 0.26 | A25034HI | 0.85 |
| A25055HI | 0.29 | A25045HI | 0.87 |
| A25031H | 0.32 | A25008H | 0.88 |
| A25027H | 0.34 | A25062HI | 0.92 |
| A25038HMI | 0.35 | A25023H | 0.92 |
| A25028H | 0.39 | A25018H | 0.93 |

TABLE 6-continued

List of the mean FoxP3 mRNA expression values in ASO-treated CD4+ T cells from donor 2 compared to mock treated cells in first screening round. Expression values are normalized to HPRT1.

| ASO | Residual FoxP3 expression (compared to mock treated cells) | ASO | Residual FoxP3 expression (compared to mock treated cells) |
|---|---|---|---|
| A25054HI | 0.49 | A25044HI | 0.94 |
| A25052HI | 0.54 | A25011H | 0.94 |
| A25020H | 0.54 | A25010H | 0.98 |
| A25029H | 0.55 | A25012H | 0.99 |
| A25051HI | 0.65 | A25013H | 1 |
| A25053HI | 0.67 | A25060HI | 1 |
| A25021H | 0.68 | A25050HI | 1.01 |
| A25037HI | 0.69 | A25022H | 1.02 |
| A25019H | 0.69 | A25009H | 1.02 |
| A25015H | 0.7 | A25032HI | 1.02 |
| A25024H | 0.76 | A25026H | 1.03 |
| A25039HI | 0.76 | A25046HI | 1.05 |
| A25016H | 0.77 | A25061HI | 1.06 |
| A25014H | 0.78 | A25006H | 1.08 |
| A25047HI | 0.78 | A25041HI | 1.09 |
| A25005H | 0.8 | A25040HI | 1.14 |
| A25036HI | 0.8 | A25004H | 1.18 |
| A25033HI | 0.81 | A25057HI | 1.21 |
| A25025H | 0.82 | A25049HI | 1.23 |
| A25017H | 0.83 | A25048HI | 1.25 |
| A25035HI | 0.83 | mock treated cells | 1.01 |
| A25063HI | 0.85 | control oligo | 1.27 |

Example 3: Target Knockdown Efficacy Screens of Human FoxP3-Specific ASOs in T Cells in a 2$^{nd}$ Screening Round The efficacy of 32 additional FoxP3-specific ASOs was tested in a second screening round. The ASOs were tested with regard to their knockdown efficacy together with 3 ASOs from the first screening round (A25027H (SEQ ID NO. 23), A25030H (SEQ ID NO. 26) and A25055HI (SEQ ID NO. 49)) in CD4+ T cells of donor 1 and donor 2. As shown in FIG. 2A and Table 7, treatment with all tested ASOs from the first screening round and A25073H (SEQ ID NO. 58), A25069H (SEQ ID NO. 56) and A25076H (SEQ ID NO. 26) from the second screening round resulted in a target inhibition of >50% (represented by a residual FoxP3 mRNA expression of <0.5 as compared to mock treated cells) in CD4+ T cells of donor 1. Furthermore, all tested ASOs from the first screening round and A25085HMI (SEQ ID NO. 66), A25092HI (SEQ ID NO. 73) and A25076H (SEQ ID NO. 26) from the second screening round resulted in a target inhibition of >40% (represented by a residual FoxP3 mRNA expression of <0.6 as compared to mock treated cells) in CD4+ T cells of donor 2 (FIG. 2B and Table 8). In contrast the control oligo did not result in an inhibition of FoxP3 expression.

TABLE 7

List of the mean FoxP3 mRNA expression values in ASO-treated CD4+ T cells from donor 1 compared to mock treated cells in second screening round. Expression values are normalized to HPRT1.

| ASO | Residual FoxP3 expression (compared to mock treated cells) | ASO | Residual FoxP3 expression (compared to mock treated cells) |
|---|---|---|---|
| A25073H | 0.37 | A25090HI | 0.89 |
| A25055HI | 0.38 | A25084HI | 0.92 |

TABLE 7-continued

List of the mean FoxP3 mRNA expression values in ASO-treated
CD4⁺ T cells from donor 1 compared to mock treated cells in second
screening round. Expression values are normalized to HPRT1.

| ASO | Residual FoxP3 expression (compared to mock treated cells) | ASO | Residual FoxP3 expression (compared to mock treated cells) |
|---|---|---|---|
| A25030HI | 0.43 | A25065H | 0.94 |
| A25027HI | 0.44 | A25081HI | 0.99 |
| A25069HI | 0.45 | A25087HI | 1.03 |
| A25076H | 0.47 | A25091HI | 1.08 |
| A25085HMI | 0.51 | A25089HI | 1.1 |
| A25075H | 0.56 | A25088HI | 1.12 |
| A25092HI | 0.58 | A25071H | 1.16 |
| A25074H | 0.63 | A25083HI | 1.27 |
| A25068H | 0.63 | A25079HI | 1.28 |
| A25078H | 0.63 | A25086HI | 1.31 |
| A25093HI | 0.67 | A25080HI | 1.55 |
| A25070H | 0.73 | A25095HI | 1.77 |
| A25077H | 0.75 | mock treated cells | 1 |
| A25072H | 0.82 | control oligo | 1.5 |
| A25082HI | 0.85 | | |

TABLE 8

List of the mean FoxP3 mRNA expression values in ASO-treated
CD4⁺ T cells from donor 2 compared to mock treated cells in second
screening round. Expression values are normalized to HPRT1.

| ASO | Residual FoxP3 expression (compared to mock treated cells) | ASO | Residual FoxP3 expression (compared to mock treated cells) |
|---|---|---|---|
| A25055HI | 0.49 | A25070H | 0.91 |
| A25030HI | 0.54 | A25081HI | 0.93 |
| A25085HMI | 0.54 | A25088HI | 0.94 |
| A25092HI | 0.54 | A25087HI | 0.95 |
| A25027HI | 0.54 | A25091HI | 0.97 |
| A25076HI | 0.59 | A25084HI | 0.97 |
| A25069HI | 0.63 | A25072H | 1.1 |

TABLE 8-continued

List of the mean FoxP3 mRNA expression values in ASO-treated
CD4⁺ T cells from donor 2 compared to mock treated cells in second
screening round. Expression values are normalized to HPRT1.

| ASO | Residual FoxP3 expression (compared to mock treated cells) | ASO | Residual FoxP3 expression (compared to mock treated cells) |
|---|---|---|---|
| A25073H | 0.64 | A25083HI | 1.1 |
| A25093HI | 0.67 | A25086HI | 1.13 |
| A25077H | 0.69 | A25065H | 1.22 |
| A25078H | 0.71 | A25079HI | 1.3 |
| A25075H | 0.72 | A25095HI | 1.37 |
| A25074H | 0.78 | A25080HI | 1.38 |
| A25089HI | 0.82 | A25071H | 1.43 |
| A25082HI | 0.82 | mock treated cells | 1 |
| A25068H | 0.84 | control oligo | 1.82 |
| A25092HI | 0.88 | | |

Example 4: Investigation of the Dose-Dependent
Target Knockdown by Selected Human
FoxP3-Specific ASOs in Regulatory T Cells The dose-dependent knockdown of FoxP3 mRNA expression by FoxP3 ASOs in human regulatory T cells was investigated on mRNA and protein level and the respective $IC_{50}$ values were calculated. Therefore, $T_{regs}$ were treated for three, seven or nine days with the respective ASO at the following concentrations: 6 µM, 1.5 µM, 375 nM, 94 nM, 24 nM, 6 nM, and 1.5 nM. After the treatment period, cells were lyzed, FoxP3 and HPRT1 mRNA expression was analyzed using the QuantiGene® Singleplex assay (ThermoFisher) and the FoxP3 expression values were normalized to HPRT1 values (FIG. 3 and Table 9). Alternatively, Foxp3 protein expression was analyzed by flow cytometry and $IC_{50}$ values on protein level were calculated (Table 10). A dose-dependent knockdown of FoxP3 mRNA and protein was observed after treatment with all tested FoxP3 ASOs (FIG. 3) with $IC_{50}$ values between 45.3 nM (A25069H (SEQ ID NO. 56) Day 9) and 404.3 nM (A25073H (SEQ ID NO. 58) Day 3) (Tables 9 and 10).

TABLE 9

Dose-dependent inhibition of FoxP3 mRNA expression in $T_{regs}$ by selected
FoxP3 ASOs and respective $IC_{50}$ values after 3, 7 and 9 days.

| mRNA | ASO | IC50 (nM) | Inhibition (%) | | | | | |
|---|---|---|---|---|---|---|---|---|
| | | | 6 µM | 1.5 µM | 375 nM | 94 nM | 24 nM | 6 nM | 1.5 nM |
| Day 3 | A25028H | 324.7 | 61.07 | 53.96 | 41.66 | 16.65 | 14.32 | 17.58 | 19.14 |
| | A25069H | 137.6 | 71.48 | 70.94 | 53.51 | 28.20 | 18.38 | −3.48 | 3.61 |
| | A25073H | 404.3 | 71.08 | 66.35 | 35.12 | 15.82 | 16.16 | −5.03 | 1.08 |
| Day 7 | A25028H | 141.2 | 78.50 | 80.38 | 64.20 | 43.13 | 19.94 | 15.12 | 22.64 |
| | A25069H | 122.6 | 73.12 | 78.60 | 61.30 | 23.25 | 11.25 | −9.29 | −8.68 |
| | A25073H | 87.2 | 78.80 | 77.52 | 54.16 | 30.39 | 31.99 | −12.91 | −3.36 |
| Day 9 | A25028H | 65.4 | 75.99 | 75.36 | 71.31 | 46.93 | 4.24 | −2.16 | −10.67 |
| | A25069H | 45.3 | 84.24 | 85.17 | 74.32 | 55.32 | 20.28 | −2.71 | −9.88 |
| | A25073H | 57.6 | 83.60 | 84.08 | 72.65 | 55.99 | 22.44 | 12.42 | 1.40 |

TABLE 10

| | Dose-dependent inhibition of FoxP3 protein expression in $T_{regs}$: $IC_{50}$ values after 3, 7 and 9 days. | |
|---|---|---|
| Protein | ASO | $IC_{50}$ (nM) |
| Day 3 | A25028H | 284.7 |
| | A25069H | 192.6 |
| | A25073H | 309.8 |
| Day 7 | A25028H | 60.8 |
| | A25069H | 124.6 |
| | A25073H | 100.0 |
| Day 9 | A25028H | 85.0 |
| | A25069H | 62.0 |
| | A25073H | 47.6 |

Example 5: $T_{reg}$ Suppression Assay

Five human FoxP3-specific ASOs (A25028H (SEQ ID NO. 24), A25031H (SEQ ID NO. 27), A25038HMI (SEQ ID NO. 34), A25069H (SEQ ID NO. 56) and A25073H (SEQ ID NO. 58)) were selected to investigate whether the knockdown of FoxP3 in $T_{regs}$ would diminish their suppressive capacity on responder T cells ($T_{resp}$). Therefore, a $T_{reg}$ suppression assay was performed. Thus, a co-culture of ASO-treated $T_{regs}$ with $T_{resp}$ (stained with a cell proliferation dye) was started four days after start of ASO treatment. Proliferation of $T_{resp}$ was analyzed by flow cytometry three days after start of co-culture. Treatment with all of the five analyzed FoxP3-specific ASOs potently reduced the suppressive capacity of the $T_{regs}$, as $T_{resp}$ could proliferate better than in co-cultures with mock- or control oligo-treated $T_{regs}$ (FIG. 4A and Table 11). Moreover, the concentration of the pro-inflammatory cytokines IFN-γ and IL-2 were analyzed in supernatants of the co-culture. The concentration of both cytokines was enhanced in all FoxP3 ASO treated cells compared to mock treated cells or when cells were treated with the control oligo neg1 (FIG. 4B, 4C and Table 11).

(GCF_000001635.26, Chr X (NC_000086.7): 7,578,119-7,596,800) was used. An "M" after the ASO ID indicates a mouse FoxP3-specific sequence that binds to an exonic region of the pre-mRNA, a "MR" after the ASO ID indicates a mouse/rat cross-reactive FoxP3 sequence that binds to an exonic region of the pre-mRNA and a "MI" after the ASO ID indicates a mouse FoxP3-specific sequence that binds to an intronic region of the pre-mRNA. 16 and 17mers were designed according to in house criteria, neg1 (described in WO2014154843 A1) was used as control oligonucleotide in all experiments (Table 4).

Example 7: Target Knockdown Efficacy Screen of Mouse FoxP3-Specific ASOs in T Cells In order to investigate the knockdown efficacy of the in silico designed mouse FoxP3 ASOs, an efficacy screening was performed in mouse CD4+ T cells. In addition cells were treated with TGF-beta, ATRA, IL-2 and stimulated with CD3/CD28 beads (ThermoFisher) in order to increase expression levels of FoxP3. Therefore, cells were treated with the respective ASO at a concentration of 5 μM for three days without the addition of a transfection reagent. Cells were lyzed after the three days treatment period, FoxP3 and HPRT1 mRNA expression was analyzed using the QuantiGene® Singleplex assay (ThermoFisher) and the FoxP3 expression values were normalized to HPRT1 values. The results are shown in FIG. 5 and Tables 12 and 13. As depicted in FIG. 5A and Table 12, three days after start of treatment a knockdown of >70% (represented by a residual FoxP3 mRNA expression of <0.3 as compared to mock treated cells) could be observed for 30 of the 70 tested ASOs (43%) in CD4+ T cells of donor mouse 1. In a second screen using CD4+ T cells from donor mouse 2, treatment with 25 of the 70 tested ASOs (36%) led to a target expression inhibition of >70% (represented by a residual FoxP3 mRNA

TABLE 11

| | List of the mean of % suppression of $T_{resp}$ vs mock treated cells, IFN-γ and IL-2 concentration in supernatant of a $T_{reg}$ suppression assay. | | | | | |
|---|---|---|---|---|---|---|
| ASO | absolute number Tresp | % proliferation (vs mock treated cells) | % suppression of Tresp | % reduced suppressive function | IFN-γ (pg/ml) | IL-2 (pg/ml) |
| A25028H | 56175.33 | 51.23 | 5.12 | 95.00 | 5200.20 | 1815.95 |
| A25031H | 55946.33 | 50.63 | 13.10 | 87.00 | 6695.27 | 1359.24 |
| A25038HMI | 73447.33 | 97.80 | 0.00 | 100.00 | 5198.62 | 1680.29 |
| A25069H | 70586.33 | 90.07 | 0.00 | 100.00 | 7907.81 | 1127.24 |
| A25073H | 51707.67 | 39.27 | 18.46 | 81.67 | 3644.65 | 703.26 |
| Mock treated cells | 37136.33 | 0.00 | 100.00 | 0.33 | 1737.02 | 91.44 |
| neg 1 | 38161.00 | 2.73 | 94.00 | 6.00 | 1743.51 | 110.82 |

Example 6: Design of Mouse FoxP3-Specific Antisense Oligonucleotides (ASOs)

For the design of ASOs with specificity for the mouse FoxP3 gene the FoxP3 mRNA sequence with the RefSeq ID NM_001199347.1 was used. For the design of ASOs with specificity for intronic regions within the mouse FoxP3 gene the FoxP3 pre-mRNA sequence (GRCm38.p6 expression of <0.3 as compared to mock treated cells) (FIG. 5B and Table 13). Of note, treatment with the control oligo had no effect on FoxP3 expression in cells isolated from donor mouse 1. In contrast, treatment with the control oligo affected the expression of FoxP3 in cells isolated from donor mouse 2, albeit to a minor degree compared with most specific ASOs. However, this has not been observed in further experiments.

TABLE 12

List of the mean FoxP3 mRNA expression values in ASO-treated
CD4⁺ T cells from donor mouse 1 compared to mock treated cells.
Expression values are normalized to HPRT1.

| ASO | Residual FoxP3 expression (compared to mock treated cells) | ASO | Residual FoxP3 expression (compared to mock treated cells) |
|---|---|---|---|
| A25063MI | 0.05 | A25008M | 0.41 |
| A25028M | 0.08 | A25044M | 0.43 |
| A25064MI | 0.10 | A25011M | 0.44 |
| A25032M | 0.10 | A25058MI | 0.44 |
| A25027M | 0.11 | A25057MI | 0.45 |
| A25026M | 0.13 | A25034MR | 0.45 |
| A25049MI | 0.14 | A25040M | 0.46 |
| A25013M | 0.15 | A25060MI | 0.46 |
| A25021M | 0.16 | A25003M | 0.48 |
| A25014M | 0.17 | A25036M | 0.48 |
| A25012M | 0.17 | A25004M | 0.48 |
| A25015M | 0.17 | A25041M | 0.48 |
| A25022M | 0.18 | A25018MR | 0.49 |
| A25016M | 0.20 | A25042M | 0.49 |
| A25024M | 0.20 | A25055MI | 0.49 |
| A25051MI | 0.20 | A25001M | 0.50 |
| A25038MR | 0.21 | A25056MI | 0.51 |
| A25053MHI | 0.22 | A25067MI | 0.52 |
| A25047MI | 0.22 | A25037MR | 0.53 |
| A25043M | 0.23 | A25010MR | 0.53 |
| A25009M | 0.23 | A25033MR | 0.54 |
| A25035M | 0.27 | A25048MI | 0.55 |
| A25025MR | 0.27 | A25052MI | 0.56 |
| A25039M | 0.27 | A25065MI | 0.56 |
| A25017M | 0.27 | A25054MRHI | 0.57 |
| A25019MR | 0.28 | A25061M | 0.58 |
| A25050MI | 0.28 | A25005M | 0.58 |
| A25069MI | 0.28 | A25045M | 0.63 |
| A25023M | 0.28 | A25006M | 0.65 |
| A25030M | 0.29 | A25007M | 0.67 |
| A25031MR | 0.32 | A25070MI | 0.68 |
| A25002MR | 0.32 | A25059MI | 0.70 |
| A25066MI | 0.33 | A25068MI | 0.78 |
| A25020M | 0.37 | A25062MI | 0.79 |
| A25029M | 0.40 | mock treated cells | 0.96 |
| A25046MI | 0.41 | control oligo | 1.00 |

TABLE 13

List of the mean FoxP3 mRNA expression values in ASO-treated
CD4⁺ T cells from donor mouse 2 compared to mock treated cells.
Expression values are normalized to HPRT1.

| ASO | Residual FoxP3 expression (compared to mock treated cells) | ASO | Residual FoxP3 expression (compared to mock treated cells) |
|---|---|---|---|
| A25028M | 0.04 | A25004M | 0.46 |
| A25063M | 0.10 | A25018MR | 0.46 |
| A25032M | 0.11 | A25066MI | 0.49 |
| A25026M | 0.11 | A25058MI | 0.49 |

TABLE 13-continued

List of the mean FoxP3 mRNA expression values in ASO-treated
CD4⁺ T cells from donor mouse 2 compared to mock treated cells.
Expression values are normalized to HPRT1.

| ASO | Residual FoxP3 expression (compared to mock treated cells) | ASO | Residual FoxP3 expression (compared to mock treated cells) |
|---|---|---|---|
| A25015M | 0.11 | A25003M | 0.49 |
| A25027M | 0.12 | A25055MI | 0.49 |
| A25022M | 0.14 | A25046MI | 0.50 |
| A25024M | 0.14 | A25010MR | 0.51 |
| A25016M | 0.15 | A25001M | 0.53 |
| A25021M | 0.15 | A25034MR | 0.57 |
| A25014M | 0.16 | A25045M | 0.58 |
| A25064MI | 0.16 | A25005M | 0.58 |
| A25025MR | 0.16 | A25057MI | 0.59 |
| A25012M | 0.17 | A25033MR | 0.62 |
| A25017M | 0.19 | A25040M | 0.63 |
| A25013M | 0.19 | A25056MI | 0.63 |
| A25009M | 0.20 | A25070MI | 0.63 |
| A25049MI | 0.20 | A25052MI | 0.65 |
| A25069MI | 0.23 | A25006M | 0.65 |
| A25038MR | 0.25 | A25065MI | 0.66 |
| A25030M | 0.25 | A25068MI | 0.66 |
| A25051MI | 0.26 | A25044M | 0.67 |
| A25053MHI | 0.27 | A25037MR | 0.71 |
| A25023M | 0.29 | A25054MRHI | 0.72 |
| A25043M | 0.30 | A25041M | 0.73 |
| A25029M | 0.34 | A25042M | 0.74 |
| A25019MR | 0.34 | A25007M | 0.78 |
| A25035M | 0.35 | A25048MI | 0.79 |
| A25011M | 0.35 | A25061MI | 0.82 |
| A25020M | 0.37 | A25060MI | 0.82 |
| A25047MI | 0.37 | A25036M | 0.82 |
| A25002MR | 0.38 | A25067MI | 0.90 |
| A25039M | 0.38 | A25059MI | 0.95 |
| A25031MR | 0.39 | A25062MI | 0.99 |
| A25050MI | 0.40 | mock treated cells | 1.01 |
| A25008M | 0.43 | control oligo | 0.68 |

Example 8: Investigation of the Dose-Dependent Target Knockdown by Selected Mouse FoxP3-Specific ASOs in T Cells The dose-dependent knockdown of FoxP3 mRNA expression by FoxP3 ASOs in mouse CD4⁺ T cells was investigated and the respective $IC_{50}$ values were calculated. Therefore, CD4⁺ T cells were treated for three days with the respective ASO at the following concentrations: 6 µM, 2 µM, 600 nM, 200 nM, 60 nM, 20 nM, 6 nM, 2 nM. After the treatment period, cells were lyzed, FoxP3 and HPRT1 mRNA expression was analyzed using the QuantiGene® Singleplex assay (ThermoFisher) and the FoxP3 expression values were normalized to HPRT1 values. A dose-dependent knockdown of FoxP3 mRNA after treatment with all tested FoxP3 ASOs (FIG. 6) was observed with $IC_{50}$ values between 146.9 nM (A25064MI (SEQ ID NO. 389)) and 2304.4 nM (A25021M (SEQ ID NO. 346)) (Table 14).

TABLE 14

Dose-dependent inhibition of FoxP3 mRNA expression in
CD4⁺ T cells by selected FoxP3 ASOs and respective $IC_{50}$ values.

| ASO | IC50 (nM) | Inhibition (%) | | | | | | | |
|---|---|---|---|---|---|---|---|---|---|
| | | 6 µM | 2 µM | 600 nM | 200 nM | 60 nM | 20 nM | 6 nM | 2 nM |
| A25014M | 754.6 | 81.89 | 62.62 | 53.37 | 41.40 | 35.31 | 19.23 | 12.13 | −4.15 |
| A25015M | 2179.7 | 82.96 | 5.63 | 52.29 | 32.48 | 34.56 | 26.82 | 1.71 | 11.44 |
| A25021M | 2304.4 | 73.89 | 59.07 | 59.75 | 37.36 | 29.00 | 27.85 | 15.91 | 1.98 |

TABLE 14-continued

Dose-dependent inhibition of FoxP3 mRNA expression in
CD4⁺ T cells by selected FoxP3 ASOs and respective $IC_{50}$ values.

| ASO | IC50 (nM) | 6 µM | 2 µM | 600 nM | 200 nM | 60 nM | 20 nM | 6 nM | 2 nM |
|---|---|---|---|---|---|---|---|---|---|
| A25022M | 599.1 | 76.84 | 52.39 | 46.92 | 32.56 | 25.58 | −5.76 | −18.14 | −33.56 |
| A25027M | 456.1 | 84.74 | 72.98 | 62.25 | 49.16 | 27.84 | 23.37 | 29.57 | 0.19 |
| A25028M | 215.2 | 93.22 | 86.17 | 76.55 | 58.16 | 65.65 | 21.20 | 27.18 | 18.60 |
| A25032M | 218.2 | 88.97 | 79.36 | 69.99 | 57.70 | 42.36 | 42.51 | 15.61 | 29.36 |
| A25049MI | 720.7 | 79.18 | 64.49 | 51.99 | 44.68 | 23.87 | 23.96 | 11.35 | 15.24 |
| A25063MI | 307.5 | 92.18 | 86.11 | 74.15 | 57.21 | 55.78 | 45.88 | 34.94 | 27.59 |
| A25064MI | 146.9 | 82.87 | 67.47 | 65.48 | 44.62 | 38.84 | 26.45 | 8.67 | 11.34 |

Example 9: $T_{reg}$ Suppression Assay

Seven mouse FoxP3-specific ASOs (A25014M (SEQ ID NO. 339), A25015M (SEQ ID NO. 340), A25021M (SEQ ID NO. 346), A25027M (SEQ ID NO. 352), A25032M (SEQ ID NO. 357), A25049MI (SEQ ID NO. 374) and A25064MI (SEQ ID NO. 389)) were selected to determine the knockdown efficacy of FoxP3-specific ASOs in natural $T_{regs}$ on protein level. The percentage of FoxP3⁺ cells (pre-gated on CD4⁺ CD25⁺ cells) was reduced by more than 90% after treatment with all ASOs investigated, resulting in less than 2% CD4⁺CD25⁺FoxP3⁺ cells (FIG. 7A and Table 15). To further investigate, whether the knockdown of FoxP3 in $T_{regs}$ would diminish the suppressive capacity of $T_{regs}$ on responder T cells ($T_{resp}$), a $T_{reg}$ suppression assay was performed. Thus, a co-culture of ASO-treated $T_{regs}$ with $T_{resp}$ (stained with a cell proliferation dye) was started four days after start of ASO treatment. Proliferation of $T_{resp}$ and their absolute cell numbers were analyzed by flow cytometry three days after start of co-culture. Treatment with four of the seven analyzed FoxP3-specific ASOs potently reduced the suppressive capacity of the $T_{regs}$, as $T_{resp}$ could proliferate better than in co-cultures with mock- or control oligo-treated $T_{regs}$ (FIG. 7B and Table 15).

a transfection reagent. Cells were lyzed after the three days treatment period, FoxP3 and HPRT1 mRNA expression was analyzed using the QuantiGene® Singleplex assay (ThermoFisher) and the FoxP3 expression values were normalized to HPRT1 values. The results are shown in FIGS. 8A and 8B as well as Tables 16 and 17. As depicted in FIG. 8A and Table 16, treatment of CD4⁺ T cells with the ASOs A25096H (SEQ ID NO. 56), A25101H (SEQ ID NO. 58), A25105H (SEQ ID NO. 23), A25110H (SEQ ID NO. 26), A25107H (SEQ ID NO. 26), A25069H (SEQ ID NO. 56), and A25126H (SEQ ID NO. 81), resulted in a target inhibition of >70% (represented by a residual FoxP3 mRNA expression of <0.3 as compared to mock treated cells). Knockdown efficacy of FoxP3-specific ASOs was furthermore tested in CD4⁺ T cells from another donor. As shown in FIG. 8B and Table 17, treatment with the ASOs A25127H (SEQ ID NO. 82), A25126H (SEQ ID NO. 81), A25069H (SEQ ID NO. 56), A25028H (SEQ ID NO. 24), A25096H (SEQ ID NO. 56), A25101H (SEQ ID NO. 58), and A25073H (SEQ ID NO. 58), resulted in a target inhibition of >70% (represented by a residual FoxP3 mRNA expression of <0.3 as compared to mock treated cells). The control oligo did not result in an inhibition of FoxP3 expression in CD4⁺ T cells from both donors.

TABLE 15

List of the mean of FoxP3⁺ cells of ASO-treated regulatory
T cells compared to mock treated cells and absolute number
of responder T cells in a $T_{reg}$ suppression assay.

| ASO | % FoxP3⁺ cells (of CD4+ CD25+) | absolute number $T_{resp}$ |
|---|---|---|
| A25014M | 1.05 | 2936.33 |
| A25015M | 1.17 | 4146.33 |
| A25021M | 1.47 | 2551.67 |
| A25027M | 0.95 | 1778.67 |
| A25032M | 0.62 | 1752.67 |
| A25049MI | 0.93 | 1831.00 |
| A25064MI | 0.86 | 2683.33 |
| Mock treated cells | 25.43 | 1411.33 |
| neg 1 | 56.03 | 1583.00 |

Example 10: Target Knockdown Efficacy Screens of Human FoxP3-Specific ASOs in T Cells in a Third Screening Round In order to investigate the knockdown efficacy of the in silico designed FoxP3 ASOs, a third efficacy screening round was performed in human CD4⁺ T cells. Therefore, cells were activated, treated with the respective ASO at a concentration of 5 µM for three days without the addition of

TABLE 16

List of the mean FoxP3 mRNA expression values in ASO-treated
CD4⁺ T cells from donor 1 compared to mock treated cells in a third
screening round. Expression values are normalized to HPRT1.

| ASO | Residual FoxP3 expression (compared to mock treated cells) | ASO | Residual FoxP3 expression (compared to mock treated cells) |
|---|---|---|---|
| A25096H | 0.20 | A25177HI | 0.72 |
| A25101H | 0.24 | A25174HI | 0.73 |
| A25105H | 0.25 | A25153H | 0.75 |
| A25110H | 0.25 | A25196HI | 0.75 |
| A25107H | 0.27 | A25156H | 0.76 |
| A25069H | 0.29 | A25128H | 0.76 |
| A25126H | 0.29 | A25123H | 0.79 |
| A25127H | 0.30 | A25195HI | 0.81 |
| A25132H | 0.30 | A25103H | 0.84 |
| A25073H | 0.34 | A25121H | 0.84 |
| A25151H | 0.34 | A25193HI | 0.84 |
| A25108H | 0.35 | A25186HI | 0.87 |
| A25028H | 0.37 | A25133H | 0.91 |
| A25099H | 0.38 | A25157H | 0.91 |
| A25113H | 0.40 | A25185HI | 0.91 |
| A25150H | 0.40 | A25163HI | 0.93 |
| A25112H | 0.42 | A25169HI | 0.94 |
| A25098H | 0.43 | A25129H | 0.97 |
| A25104H | 0.43 | A25119H | 0.98 |

TABLE 16-continued

List of the mean FoxP3 mRNA expression values in ASO-treated CD4+ T cells from donor 1 compared to mock treated cells in a third screening round. Expression values are normalized to HPRT1.

| ASO | Residual FoxP3 expression (compared to mock treated cells) | ASO | Residual FoxP3 expression (compared to mock treated cells) |
|---|---|---|---|
| A25114H | 0.43 | A25175HI | 1.00 |
| A25109H | 0.44 | A25194HI | 1.03 |
| A25158H | 0.45 | A25187HI | 1.04 |
| A25176HI | 0.45 | A25118H | 1.04 |
| A25179HI | 0.45 | A25161HI | 1.06 |
| A25180HI | 0.45 | A25134H | 1.07 |
| A25190HI | 0.46 | A25160HI | 1.08 |
| A25116H | 0.47 | A25140H | 1.09 |
| A25189HI | 0.49 | A25167HI | 1.10 |
| A25115H | 0.51 | A25145H | 1.11 |
| A25147H | 0.52 | A25152H | 1.14 |
| A25149H | 0.52 | A25139H | 1.15 |
| A25182HI | 0.53 | A25188HI | 1.15 |
| A25097H | 0.53 | A25141H | 1.15 |
| A25102H | 0.53 | A25154H | 1.16 |
| A25192HI | 0.54 | A25125H | 1.16 |
| A25100H | 0.55 | A25184HI | 1.18 |
| A25135H | 0.55 | A25142H | 1.21 |
| A25191HI | 0.56 | A25143H | 1.22 |
| A25178HI | 0.56 | A25155H | 1.22 |
| A25117H | 0.57 | A25144H | 1.22 |
| A25159H | 0.58 | A25130H | 1.23 |
| A25138H | 0.58 | A25137H | 1.24 |
| A25148H | 0.60 | neg1 | 1.25 |
| A25164HI | 0.61 | A25146H | 1.26 |
| A25106H | 0.61 | A25122H | 1.30 |
| A25183HI | 0.62 | A25173HI | 1.31 |
| A25181HI | 0.63 | A25162HI | 1.35 |
| A25131H | 0.65 | A25170HI | 1.43 |
| A25165HI | 0.66 | A25136H | 1.45 |
| A25120H | 0.67 | A25199HI | 1.49 |
| A25111H | 0.67 | A25197HI | 1.79 |
| A25171HI | 0.69 | A25166HI | 1.83 |
| A25172HI | 0.71 | A25168HI | 1.86 |
| A25124H | 0.71 | A25198HI | 2.13 |

TABLE 17

List of the mean FoxP3 mRNA expression values in ASO-treated CD4+ T cells from donor 2 compared to mock treated cells in a third screening round. Expression values are normalized to HPRT1.

| ASO | Residual FoxP3 expression (compared to mock treated cells) | ASO | Residual FoxP3 expression (compared to mock treated cells) |
|---|---|---|---|
| A25127H | 0.20 | A25149H | 0.76 |
| A25126H | 0.23 | A25193HI | 0.77 |
| A25069H | 0.24 | A25133H | 0.78 |
| A25028H | 0.26 | A25174HI | 0.79 |
| A25096H | 0.29 | A25120H | 0.80 |
| A25101H | 0.29 | A25156H | 0.81 |
| A25073H | 0.29 | A25153H | 0.82 |
| A25107H | 0.32 | A25185HI | 0.82 |
| A25105H | 0.34 | A25163HI | 0.82 |
| A25132H | 0.35 | A25161HI | 0.89 |
| A25108H | 0.35 | A25111H | 0.90 |
| A25147H | 0.38 | A25194HI | 0.91 |
| A25182HI | 0.38 | A25195HI | 0.92 |
| A25135H | 0.38 | A25134H | 0.93 |
| A25110H | 0.39 | A25196HI | 0.93 |
| A25191HI | 0.40 | A25160HI | 0.94 |
| A25099H | 0.41 | A25157H | 0.95 |
| A25150H | 0.42 | A25103H | 0.97 |
| A25151H | 0.44 | A25129H | 1.00 |

TABLE 17-continued

List of the mean FoxP3 mRNA expression values in ASO-treated CD4+ T cells from donor 2 compared to mock treated cells in a third screening round. Expression values are normalized to HPRT1.

| ASO | Residual FoxP3 expression (compared to mock treated cells) | ASO | Residual FoxP3 expression (compared to mock treated cells) |
|---|---|---|---|
| A25190HI | 0.45 | A25186HI | 1.02 |
| A25176HI | 0.46 | A25169HI | 1.04 |
| A25181HI | 0.46 | A25184HI | 1.06 |
| A25189HI | 0.48 | A25121H | 1.07 |
| A25183HI | 0.48 | A25125H | 1.08 |
| A25172HI | 0.48 | A25167HI | 1.09 |
| A25104H | 0.48 | A25155H | 1.13 |
| A25171HI | 0.49 | A25173HI | 1.13 |
| A25158H | 0.50 | A25162HI | 1.14 |
| A25192HI | 0.50 | A25140H | 1.21 |
| A25164HI | 0.54 | A25145H | 1.22 |
| A25179HI | 0.58 | A25152H | 1.25 |
| A25109H | 0.58 | A25144H | 1.25 |
| A25100H | 0.59 | A25143H | 1.25 |
| A25138H | 0.59 | A25187HI | 1.29 |
| A25159H | 0.60 | A25119H | 1.29 |
| A25112H | 0.62 | A25122H | 1.32 |
| A25178HI | 0.63 | A25170HI | 1.33 |
| A25128H | 0.63 | A25137H | 1.35 |
| A25116H | 0.63 | A25154H | 1.39 |
| A25177HI | 0.63 | A25118H | 1.40 |
| A25124H | 0.63 | A25175HI | 1.41 |
| A25097H | 0.64 | neg1 | 1.43 |
| A25113H | 0.64 | A25188HI | 1.43 |
| A25114H | 0.65 | A25141H | 1.44 |
| A25115H | 0.65 | A25199HI | 1.53 |
| A25098H | 0.65 | A25139H | 1.59 |
| A25102H | 0.66 | A25146H | 1.68 |
| A25106H | 0.67 | A25136H | 1.71 |
| A25180HI | 0.68 | A25130H | 1.71 |
| A25148H | 0.69 | A25166HI | 1.96 |
| A25131H | 0.69 | A25142H | 2.03 |
| A25117H | 0.71 | A25197HI | 2.21 |
| A25165HI | 0.71 | A25168HI | 2.21 |
| A25123H | 0.75 | A25198HI | 2.83 |

Example 11: Investigation of the Dose-Dependent Target Knockdown by Selected Human FoxP3-Specific ASOs in Regulatory T Cells The dose-dependent knockdown of FoxP3 mRNA expression by FoxP3 ASOs in human regulatory T cells was investigated on mRNA level and the respective $IC_{50}$ values were calculated. Therefore, $T_{regs}$ were treated for three days with the respective ASO at the following concentrations: 6 µM, 1.5 µM, 375 nM, 94 nM, 24 nM, 6 nM, and 1.5 nM. After the treatment period, cells were lyzed, FoxP3 and HPRT1 mRNA expression was analyzed using the Quanti-Gene® Singleplex assay (ThermoFisher) and the FoxP3 expression values were normalized to HPRT1 values (FIG. 9 and Table 18). A dose-dependent knockdown of FoxP3 mRNA was observed after treatment with all tested FoxP3 ASOs (FIG. 9) with $IC_{50}$ values between 109 nM (A25101H; SEQ ID NO. 58) and 1758 nM (A25151H; SEQ ID NO. 104) (Table 18):

TABLE 18

Dose-dependent inhibition of FoxP3 mRNA expression in regulatory T cells by
selected FoxP3 ASOs and respective $IC_{50}$ values after 3 days ASO treatment.

| ASO | IC50 (nM) | 6 µM | 1.5 µM | 375 nM | 94 nM | 24 nM | 6 nM | 1.5 nM |
|---|---|---|---|---|---|---|---|---|
| A25096H | 177 | 95.69 | 86.34 | 75.96 | 50.04 | 23.25 | 19.92 | |
| A25099H | 775 | 85.73 | 75.34 | 53.58 | 42.37 | 29.56 | 54.35 | 50.59 |
| A25101H | 109 | 89.05 | 78.83 | 58.88 | 38.84 | 7.00 | 37.41 | 3.26 |
| A25104H | 933 | 81.02 | 64.23 | 41.70 | 16.03 | 46.69 | 28.93 | 24.79 |
| A25108H | 932 | 80.17 | 29.73 | 14.45 | −1.41 | −21.37 | 9.59 | −10.29 |
| A25112H | 762 | 81.06 | 74.60 | 22.72 | 7.25 | −12.75 | 45.90 | 26.31 |
| A25113H | 1030 | 66.87 | 64.93 | 46.13 | 7.52 | 36.62 | 31.35 | 36.68 |
| A25126H | 911 | 82.52 | 65.41 | 32.10 | −39.85 | −2.44 | 27.56 | 39.19 |
| A25127H | 728 | 89.68 | 70.19 | 46.17 | 18.30 | 7.89 | 38.62 | 25.40 |
| A25150H | 173 | 80.92 | 56.63 | 26.38 | 6.89 | −28.14 | −54.91 | −48.92 |
| A25151H | 1758 | 68.59 | 48.81 | 15.75 | 24.95 | −18.90 | −6.28 | 19.16 |
| A25179HI | 417 | 79.76 | 54.80 | 9.80 | 5.68 | 24.55 | −0.35 | −4.60 |
| A25182HI | 341 | 77.97 | 60.60 | 40.01 | 16.19 | −30.50 | 9.87 | 7.42 |
| A25190HI | 1077 | 63.82 | 24.29 | 8.54 | −34.72 | −61.19 | −32.11 | 9.27 |
| A25191HI | 395 | 81.72 | 58.45 | 51.33 | 2.89 | −31.46 | −6.32 | |

Example 12: Investigation of the Dose-Dependent Target Knockdown by Selected Human FoxP3-Specific ASOs in Regulatory T Cells The dose-dependent knockdown of FoxP3 mRNA expression by FoxP3 ASOs in human regulatory T cells was further investigated on mRNA and protein level and the respective $IC_{50}$ values were calculated. Therefore, $T_{regs}$ were treated for three, six or ten days with the respective ASO at the following concentrations: 6 µM, 1.5 µM, 375 nM, 94 nM, 24 nM, 6 nM, and 1.5 nM. After the treatment period, cells were lyzed, FoxP3 and HPRT1 mRNA expression was analyzed using the QuantiGene® Singleplex assay (ThermoFisher) and the FoxP3 expression values were normalized to HPRT1 values (FIG. 10 and Table 19). Alternatively, Foxp3 protein expression was analyzed by flow cytometry and $IC_{50}$ values on protein level were calculated (Table 20). A dose-dependent knockdown of FoxP3 mRNA and protein was observed after treatment with all tested FoxP3 ASOs (FIG. 10) with $IC_{50}$ values between 12.5 nM (A25150H (SEQ ID NO. 103) Day 10) and 603.1 nM (A25150H Day 3) (Tables 19 and 20):

TABLE 19

Dose-dependent inhibition of FoxP3 mRNA expression in $T_{regs}$ by selected
FoxP3 ASOs and respective $IC_{50}$ values after 3, 6 and 10 days.

| mRNA | ASO | IC50 (nM) | 6 µM | 1.5 µM | 375 nM | 94 nM | 24 nM | 6 nM | 1.5 nM |
|---|---|---|---|---|---|---|---|---|---|
| Day 3 | A25073H | 181.9 | 84.95 | 77.74 | 52.78 | 30.00 | 6.10 | −12.51 | 0.52 |
| | A25126H | 129.5 | 87.33 | 77.45 | 57.84 | 35.10 | 6.38 | 5.54 | −16.32 |
| | A25150H | 603.1 | 78.42 | 62.81 | 40.71 | 31.52 | 14.73 | −0.94 | 3.10 |
| Day 6 | A25073H | 25.2 | 67.64 | 84.39 | 75.00 | 63.89 | 29.58 | 14.21 | −6.33 |
| | A25126H | 63.7 | 64.94 | 72.25 | 65.59 | 50.24 | 16.00 | 9.58 | 9.64 |
| | A25150H | 61.4 | 59.72 | 63.17 | 59.36 | 41.42 | 11.60 | 5.92 | −1.49 |
| Day 10 | A25073H | 24.5 | 100.00 | 89.50 | 91.08 | 78.14 | 56.82 | 40.45 | 27.46 |
| | A25126H | 46.3 | 90.61 | 99.51 | 94.89 | 83.11 | 55.23 | 48.08 | 39.93 |
| | A25150H | 12.5 | 96.51 | 97.62 | 93.23 | 75.34 | 53.99 | 35.02 | 10.54 |

TABLE 20

Dose-dependent inhibition of FoxP3 protein expression
in $T_{regs}$: $IC_{50}$ values after 3, 6 and 10 days.

| Protein | ASO | $IC_{50}$ (nM) |
|---|---|---|
| Day 3 | A25073H | 87.5 |
| | A25126H | 161.5 |
| | A25150H | 358.2 |
| Day 6 | A25073H | 41.5 |
| | A25126H | 61.0 |
| | A25150H | 74.9 |
| Day 10 | A25073H | 43.4 |
| | A25126H | 30.0 |
| | A25150H | 53.7 |

60

The invention claimed is:

1. An oligonucleotide comprising the nucleotide sequence of SEQ ID NO:81, wherein at least one of the nucleotides comprises a modification selected from the group consisting of LNA (locked nucleic acid), ENA (2'-O,4'-C-ethylene-bridged nucleic acid), a 2'-fluoro modified nucleotide, a 2-O-methyl modified nucleotide, a 2-O-methoxy modified nucleotide, a FANA (2'-deoxy-2-fluoro-D-arabinonucleic acid), and a combination thereof, and hybridizing with a nucleic acid sequence of Foxp3 of SEQ ID NO. 1 and/or of SEQ ID NO. 2 resulting in a reduction of FoxP3, FoxP3 mRNA, FoxP3 pre-mRNA or a combination thereof of 40% to 99% within 6 to 240 h or within 12 to 120 h from first administration of the oligonucleotide compared to an untreated control.

2. The oligonucleotide according to claim 1, wherein the oligonucleotide results in a reduction of FoxP3, FoxP3 mRNA, FoxP3 pre-mRNA, or a combination thereof, of 40% to 99%, within 24 to 72 h from first administration of the oligonucleotide to a subject.

3. The oligonucleotide according to claim 1, wherein the oligonucleotide hybridize with Foxp3 of SEQ ID NO. 1 and/or SEQ ID NO. 2, wherein the oligonucleotide hybridizes within a region of position 1510 to 2109 of SEQ ID NO. 2.

4. The oligonucleotide according to claim 1, wherein the oligonucleotide is

```
                            (A25126H; SEQ ID NO. 81)
    +G*+A*+A*G*T*A*A*T*C*T*G*T*G*C*G*+A*+G*+C,
``` wherein + indicates an LNA modified nucleotide and * indicates a phosphorothioate (PTO) linkage between the nucleotides.

5. The oligonucleotide according to claim 1, wherein the oligonucleotide inhibits the expression of FoxP3, FoxP3 mRNA, FoxP3 pre-mRNA or a combination thereof at a nanomolar or micromolar concentration.

6. A pharmaceutical composition comprising an oligonucleotide according to claim 1 and a pharmaceutically acceptable carrier, excipient, diluent or a combination thereof.

7. The pharmaceutical composition of claim 6, further comprising an antibody.

8. The pharmaceutical composition of claim 7, wherein the antibody inhibits expression or activity of PD-1.

9. The pharmaceutical composition of claim 7, wherein the antitumor active agent is an antibody that inhibits expression or activity of a factor involved in cancer progression and/or metastasis selected from the group consisting of SND1, MTDH, HER-2, BRAF, KRAS, VEGF, EGFR1, EGFR2, BCR/ABL, ABL, MET, ALK, JAK2, BTK, miR-223, CCL18, CCL20, Lcn2, CCL5/CCR9, DDR2, PHD2, IL6, SDF-1/CXCL12 and a combination thereof.

10. The oligonucleotide according to claim 1 that reduces expression of FoxP3, FoxP3 mRNA, FoxP3 pre-mRNA or a combination thereof when administered to a subject having a disorder characterized by overexpression of FoxP3, FoxP3 mRNA, FoxP3 pre-mRNA.

11. The oligonucleotide according to claim 10, wherein the disorder is a malignant and/or benign tumor, a chronic infectious disease, a chronic inflammatory disease caused by infection or a combination thereof.

12. The oligonucleotide according to claim 11, wherein the malignant tumor is selected from the group consisting of breast cancer, lung cancer, malignant melanoma, lymphoma, skin cancer, bone cancer, prostate cancer, liver cancer, brain cancer, cancer of the larynx, gall bladder cancer, pancreatic cancer, testicular cancer, rectal cancer, parathyroid cancer, thyroid cancer, adrenal cancer, neural tissue cancer, head and neck cancer, colon cancer, stomach cancer, bronchial cancer, kidney cancer, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythemia vera, adenocarcinoma, anaplastic astrocytoma, glioblastoma multiforma, leukemia, epidermoid carcinoma and a combination thereof.

13. The oligonucleotide according to claim 11, wherein the chronic infectious disease is selected from the group consisting of hepatitis B and/or C virus, human immune deficiency virus, cytomegalovirus, Herpes Simplex virus, measles virus, respiratory syncytial virus, *Helicobacter pylori* infection and a combination thereof, or wherein the chronic inflammatory disease caused by infection is selected from the group consisting of chronic inflammatory diseases of the liver, liver fibrosis, liver cirrhosis and a combination thereof.

14. The pharmaceutical composition according to claim 11, wherein the composition is suitable to be administered locally or systemically.

\* \* \* \* \*

SEQUENCE LISTING

<160> NUMBER OF SEQ ID NOS: 396

<210> SEQ ID NO 1
<211> LENGTH: 2397
<212> TYPE: DNA
<213> ORGANISM: Homo sapiens

<400> SEQUENCE: 1

```
gcacacactc atcgaaaaaa atttggatta ttagaagaga gaggtctgcg gcttccacac        60
cgtacagcgt ggttttctt ctcggtataa aagcaaagtt gtttttgata cgtgacagtt        120
tcccacaagc caggctgatc cttttctgtc agtccacttc accaagcctg cccttggaca        180
aggacccgat gcccaacccc aggcctggca agccctcggc cccttccttg gcccttggcc        240
catccccagg agcctcgccc agctggaggg ctgcacccaa agcctcagac ctgctggggg        300 cccgggccc aggggggaacc ttccagggcc gagatcttcg aggcggggcc catgcctcct       360
cttcttcctt gaaccccatg ccaccatcgc agctgcagct gcccacactg cccctagtca       420
tggtggcacc ctccggggca cggctgggcc ccttgcccca cttacaggca ctcctccagg       480
acaggccaca tttcatgcac cagctctcaa cggtggatgc ccacgcccgg accctgtgc        540 tgcaggtgca cccctggag agcccagcca tgatcagcct cacaccacc accaccgcca        600 ctggggtctt ctccctcaag gcccggcctg gcctcccacc tgggatcaac gtggccagcc       660
tggaatgggt gtccagggag ccggcactgc tctgcacctt cccaaatccc agtgcaccca       720
ggaaggacag cacctttcg gctgtgcccc agagctccta cccactgctg gcaaatggtg        780
tctgcaagtg gcccggatgt gagaaggtct tcgaagagcc agaggacttc ctcaagcact       840
gccaggcgga ccatcttctg gatgagaagg gcagggcaca atgtctcctc cagagagaga       900
tggtacagtc tctggagcag cagctggtgc tggagaagga gaagctgagt gccatgcagg       960
cccacctggc tgggaaaatg gcactgacca aggcttcatc tgtggcatca tccgacaagg       1020
gctcctgctg catcgtagct gctggcagcc aaggccctgt cgtcccagcc tggtctggcc       1080
cccgggaggc ccctgacagc ctgtttgctg tccggaggca cctgtggggt agccatggaa       1140
acagcacatt cccagagttc ctccacaaca tggactactt caagttccac aacatgcgac       1200
cccctttcac ctacgccacg ctcatccgct gggccatcct ggaggctcca gagaagcagc       1260
ggacactcaa tgagatctac cactggttca cacgcatgtt tgccttcttc agaaaccatc       1320
ctgccacctg gaagaacgcc atccgccaca acctgagtct gcacaagtgc tttgtgcggg       1380
tggagagcga gaaggggggct gtgtggaccg tggatgagct ggagttccgc aagaaacgga       1440
gccagaggcc cagcaggtgt tccaaccta cacctggccc ctgacctcaa gatcaaggaa        1500
aggaggatgg acgaacaggg gccaaactgg tgggaggcag aggtggtggg ggcagggatg       1560
ataggccctg gatgtgccca cagggaccaa gaagtgaggt ttccactgtc ttgcctgcca       1620
gggcccctgt tccccgctg gcagccaccc cctcccccat catatccttt gccccaaggc        1680
tgctcagagg ggccccggtc ctggcccag ccccaccte cgcccagac acaccccca          1740 gtcgagccct gcagccaaac agagccttca caaccagcca cacagagcct gcctcagctg       1800
ctcgcacaga ttacttcagg gctggaaaag tcacacagac acacaaaatg tcacaatcct       1860
gtccctcact caacacaaac cccaaaacac agagagcctg cctcagtaca ctcaaacaac       1920
ctcaaagctg catcatcaca caatcacaca caagcacagc cctgacaacc cacacacccc       1980
aaggcacgca cccacagcca gcctcagggc ccacaggggc actgtcaaca caggggtgtg       2040
cccagaggcc tacacagaag cagcgtcagt accctcagga tctgaggtcc caacacgtgc       2100
```

-continued

```
tcgctcacac acacggcctg ttagaattca cctgtgtatc tcacgcatat gcacacgcac      2160 agcccccccag tgggtctctt gagtcccgtg cagacacaca cagccacaca cactgccttg      2220
ccaaaaatac cccgtgtctc ccctgccact cacctcactc ccattccctg agccctgatc      2280
catgcctcag cttagactgc agaggaacta ctcatttatt tgggatccaa ggcccccaac      2340
ccacagtacc gtccccaata aactgcagcc gagctcccca caaaaaaaaa aaaaaaa        2397

<210> SEQ ID NO 2
<211> LENGTH: 17451
<212> TYPE: DNA
<213> ORGANISM: Homo sapiens

<400> SEQUENCE: 2
gggtcatgtg ggctgtcagg catagtgtgg ccgcacaggg acctcacacc ctcaggcaga        60
gctgtccagt cacactctaa cacagaatag tcacacacaa tccatcccag tcacccctga       120
cacagtgaca cagtccctgt ctggtacaca tgaggaccct ccactgctag ccagcctgcc       180
ccaggcaggg gctcatggct gccatggtgt ctgccagatc ttgtctgata cgaaggagct       240
tcagaaggaa atcaactccc tatctgggaa gctggaccgg acgtttgcgg tgactgatga       300
gcttgtgttc aaggtgtggg gcaggttggg cgggggtgag tggggtgagg ctgggctgct       360
gccttgtgca tctgctaatt ggctggctgg ggtccagacc caggccctgt gcgaggctgg       420
aggtgcactg atacccaggg ctggctttgt ttcatggagg atgaagctag tggggtggtg       480
ggagagggtg gccttcttag ggcatggaga tggtcaaggg cagcccactg ataccttttga       540 ggtccctgtg tctggtcagg atgccaagaa ggacgatgct gttcggaagg cctataagta       600
tctagctgct ctgcacgagg tgaggggaga catgtgcctg gggtggggct gctgggggtg       660
ggtgggactg ggtgcaagcc ttctgctcct gttgtcccca gaactgcagc cagctcatcc       720
agaccatcga ggacacaggc accatcatgc gggaggttcg agacctcgag gagcaggtga       780
ggcctggggg caggatgggg agccaaggcg ggccgggggg acagttcctc aggttatgct       840
gacagaggct gtggagccac acacagccga tggctggaca cccagccctg ccccttagtg       900
cctgtgacct gggacaggca agtggcctac tgtgagcccc agcttccacc ccaagggccc       960
tcctgtctgc ctcccagggc catgggcaga ggcttcagct taaagatgta gggggaatcc      1020
tgccacatgg cgaaggatgc tttgggtaga gggaacacca cacgaggcct ggccatggga      1080
cagagcaggc tgttggagtt ggtgggaggg gcccagagtg gctgtgatgg gggctggtga      1140
gcaggagctg ggaaagggggc tgtgtgtgct gaggggggcat gtgttcacat tgcctcagat      1200
cgagacagag ctgggcaaga agaccctcag caacctggag aagatccggg aggactaccg      1260
agccctccgc caggagaacg ctggcctcct aggccgggtc cggaggcct gaggagccgc      1320 cggcagaggt ctctccccag cctcaggcag ggatttgggg tgctggaggc agtggccaag      1380
cacatgccct agctacttcc tccgctgtcc agttcctcct gctgcggcct tggacccaga      1440
cccctgccca ctgaccgcaa cccttatatg gggtgatagt ccagcatgtg gggagctcgg      1500 ctgcagtttta ttggggacgg tactgtgggt tgggggcctt ggatcccaaa taaatgagta      1560
gttcctctgc agtctaagct gaggcatgga tcagggctca gggaatggga gtgaggtgag      1620
tggcagggga gacacggggt atttttggca aggcagtgtg tgtggctgtg tgtgtctgca      1680
cgggactcaa gagacccact gggggggctgt gcgtgtgcat atgcgtgaga tacacaggtg      1740
aattctaaca ggccgtgtgt gtgagcgagc acgtgttggg acctcagatc ctgagggtac      1800
```

-continued

```
tgacgctgct tctgtgtagg cctctgggca cacccctgtg ttgacagtgc ccctgtgggc   1860
cctgaggctg gctgtgggtg cgtgccttgg ggtgtgtggg ttgtcagggc tgtgcttgtg   1920
tgtgattgtg tgatgatgca gctttgaggt tgtttgagtg tactgaggca ggctctctgt   1980 gttttgtgggt ttgtgttgag tgagggacag gattgtgaca ttttgtgtgt ctgtgtgact   2040
tttccagccc tgaagtaatc tgtgcgagca gctgaggcag gctctgtgtg gctggttgtg   2100
aaggctctgt ttggctgcag ggctcgactg ggggtgtgt ctgggcgga ggtgggggct   2160 ggggccagga ccgggccccc tctgagcagc cttggggcaa aggatatgat gggggagggg   2220
gtggctgcca gcgggggaac aggggccctg gcaggcaaga cagtggaaac ctcacttctt   2280
ggtccctgtg ggcacatcca gggcctatca tccctgcccc caccacctct gcctcccacc   2340
agtttggccc ctgttcgtcc atcctccttt ccttgatctt gaggtcaggg gccaggtgta   2400
gggttggaac acctgctggg cctctggctc cgtttcttgc ggaactccag ctcatccacg   2460
gtccacacag cccccttctc gctctccacc cgcacaaagc acttgtgcag actcaggttg   2520
tggcggatgg cgttctgtgg aaggccgggg acagggagc ggtgggcgtc aacctctgag   2580
gccagcagcc accaccaaca acccacatcc cgttcctccc caatgtgcct atgagcccag   2640
acccaggcct gcccactttg agctgcgatg gcacttgagg ccatcccagt caccgccacc   2700
tcagaggagc tcaccttcca ggtggcagga tggtttctga agaaggcaaa catgcgtgtg   2760
aaccagtggt agatctcatt gagtgtccgc tgcttctctg gagcctccag gatggcctgg   2820
aagttggggg gtggggtaag gggcacattc cccaaacttg gggtttagag gggctatgac   2880
ctaccccgag ccatctgaca tgggggcgga attgtagggg caggtaatca gggacaggac   2940
tagatgtggg gtgaagcatg gggtcaaaga tggggttaga aaaggggtga agtgtcgggt   3000
tgggcagggt tagatgggtg tgggtatggt tgttctggga ttaggtaagg gatcaggact   3060
gaggttggga gtggggtctt gttcagggct agggctgaag tgaggtgaaa ggtctgggat   3120
ggagttggag ttggggttct ctgtggaggt gacatttcag ggttggggaa ggtgaaggt   3180 cagaagtggg gtcaaggatt tggaagggt aaagggccag gccaacttaa gggtcaggga   3240
aggggtgggt taagagtcag gctggggtgg actcaggtgg ggggtctagg ggtgagggat   3300
gggatgactt ggctttaggt cagaagccag agatggtttg aattatcgag tatcttacgt   3360
gtcagggaca tggttaggtg gttaggctca gggcaaggat gaggttagtt gtggggttcg   3420
gtgtggagtg aggctgaggg tcagggaatt tgatcagttt ggattcagga atgggattac   3480
agagtcagcg atgatgattg cagtgaggct atcagtcagg atggggctag gtcagggttt   3540
cagttcagag acagtcgggg aatatctggt atcatgtagg ggtgaggttc aggtttgggg   3600
ttaggtgtgg cgctaggatg aaggttctga gaaggcattg gggaggctga gatgaaggag   3660
ttgggatggg gtgatgaagt taaggatcaa atgggtgtta caaggaaagg ttgggaatgg   3720
tgcccagttg ggggtgtatt gacatactgg ggtacgttgg ggccagggaa ggagatgggg   3780
ttgggttggc ataaaggctg gggaaggagt tagagtaaga gctggggtac gtttagggca   3840
aggtgcagag atggggttag ctttaggcta ttttatgggt ccaggagagg gttaggtatg   3900
gggctgaggg ggacatctgg aaaggggtag gtttagggtc agaatttggc atgctctggc   3960
ctggatggtg gtttaggttt ggatttgcgg acaggtttgg ggtgaagcca gcatgagggg   4020
tcacatttga ggcacggctt ggggatcctt ggggctgggg cttgggaatg gaggaaccca   4080
ctctgagggc actcagaggg agacaggagt ttggaggca ggtcccccac cccatctttg   4140
tcttcctcct ccttggggcc gagctgccct gcttacccag cggatgagcg tggcgtaggt   4200
```

-continued

```
gaaaggggggt cgcatgttgt ggaacttgaa gtagtccatg ttgtggagga actctgtcag   4260
agggtgggga tgaatcaagc cccatgcagg acctcctagc tagctccctg tcccctcccc   4320
ctacaaggtg agtctacagg cctgagatct caccgtcaac accgtgtcc acgggcacag    4380 gtactgtttg ctgagcacct gacataagtt gtatcattta ttctttgcac cacttctgcc   4440
aaaatagttc tccccgaggt tgaaagaag cggagtaact tgcacaccaa aggatgcaag    4500
aggttaaatg gcagagccag gatgacagtc aaggtctctg atccctgcta agcccacagg   4560
ccaggcctgg tggagagcag tggataggtg agctcgggcg aatccacccc gattttcctt    4620
ggtcagggga ggaaaggagg tgctcctgga attacttagc agggtccctc ccttctgatg   4680
gccgaatata gtagctggag tccagagtgg gtgaggcatg gccccaatcc ccaagggagt    4740
cagggctagg ggcccgacac tcgagaccat atggggggct ttcaggccac ggacatcccg   4800
aaaggaagct tttgtgagcg gatgcatttt cccaaaggct gagtggcggc agctgcagtg   4860
gtggtggtgg tgggaagggg cagcatggag ctcctttgca ccctccaccc agagcctgtc    4920
aggattagga gcttgggggc accgtgtagt gcaaggacca ttcttacctg ggaatgtgct    4980
gtttccatgg ctaccccaca ggtgcctccg gacagcaaac aggctgtcag gggcctcccg    5040
ggggccagac caggctggga cgacagggcc ttggctgcca gcagctacga tgcagcagga   5100
gcccttgtcg gatgatgcct gggtgagggg gagaggctgg tgaccagag gcttaaactt     5160 cccactttt actttctatt ttatgttttt tattttttt gatactgagt cttgctctgt      5220
cgcccaggct ggagtgcagt ggtgcaatct cggctcactg caaccccac ctcccagatt      5280 caagcaagtc ttctgcctca gcctcccgag tagctgggac tacaggtgcc cgtcactacg    5340
cccagctaat ttttgtattt ttggtagaga tggggtttca ccatgttagc caggctggtc    5400
tcgaactcct gacctcatgt gatccacccg cttcagcctc ccaaagtgct gggattacag    5460
gcatgagcca ctgcgcctgg ctccacttta tttttaaatc agtgtttttc aaagcaagga    5520
cgccctcttc taaattccag tctgaggtgg aatcccacaa aacagcatga gccgtattta    5580
ttagagcaca ggtgcggatg tcgtatgtgg ccactgatgc tgggaccatg aactgggggtt   5640 gaatagggct ctttaccacc caactgtgac cttgggaaag tcacctaaac cccctggcc     5700 tcaatattcc tcatctgtac attcgcatca tgagaaataa attaccacca gcaaagcgct    5760
cagaaacagt gcctggcctc cagggctggc ttcatgggcg tgtgacctat gtggttatgt    5820
ggcaccctgt gctttgttta atgctctgtg gtcgccatct tgaaatctga acaaggggcc    5880
ctgcaggtta catagctggt cctgctggca cacagcctgc atctggcaag tctggctatt    5940
tgcatttgct ttaacaactc aggatcacag tgtttgggga tcttagagtc agagggtttt    6000 ttttttttt ttttcttgag acggagtctt gatctgtcgc ctaggctgga gtgcagtggt    6060
atgatctcag ctcactgcaa actccgcctc ccaggttcaa gcaattctct gcctcagcct    6120
cccaagtagt tgggactaca gacacctgcc accacgcctg gctaattttt tgtacttttta   6180 gtagacacag ggtttcacca tcttggcgag gctggtcttg aactcctgac ctcgtgatcc     6240
acccgcctcg gcctcccaaa gtgctgggat tacaggcgtg agccaccacg cccagccggg    6300
gtcagagggt ttgtaagtag aaggggacag atttccaggt ctgggcatgt ttggagctgg    6360
ggacaggggc ccctagctct caggacctga atgtgaggtt aggttccctg caccgtgcag    6420
acctcctccc tgcccccag cagtctgagt ctgccaccac cagtcctggg gtcgctcacc     6480
acagatgaag ccttggtcag tgccattttc ccagccaggt gggcctgcat ggcactcagc    6540
```

-continued

```
ttctccttct  ccagcaccag  ctgtgaaatg  gcacaaacat  gaggcctcag  cctggccctt      6600
ctctgccaca  tctttgccca  ggctacggtc  ttccctggga  gtgcccgctc  ctcttccttc      6660
ctttatacca  gccctcgtcc  caggtgaact  tggtttctgg  cacatggtgg  acagaaggtt      6720
ttgcgcacta  tccctatccc  ttaccctcca  ccgccctggc  attacctgct  gctccagaga      6780
ctgtaccatc  tctctctgga  ggagacattg  tgccctgccc  ttctcatcca  gaagatggtc      6840
cgcctggcag  tgcctaagta  gggagaagat  tccatgcagg  tgaccacgac  aggcctggtc      6900
tggctcaatg  ctctgaatgg  ggagggccca  gaccctctgg  gagttctctc  ctctgagccc      6960
cagctcccct  cccctctcta  cctcagtctc  cctctcacac  ccctcgttcc  cttaacacat      7020
gcccctcagc  acctactgca  tgtcaggcct  gaactcacca  cttgagcctg  gccagagtgc      7080
tggagataat  gttggaagtg  tggtgagttg  agaatgggcc  agggaggtga  gagtgggcaa      7140
agcattctgg  gtggagggac  ggcctgtgca  aaggcctggc  tgcaaggagg  acaggacatg      7200
tggggttgct  gctaagggtt  gtgtgtagtg  tggtgtgtat  ttgtgtgtgt  gtgtgtgtga      7260
gagagagaga  aagagagaga  gagagagaga  gagagagaga  gagagagaga  gagagagaga      7320
gagagacata  tgggggggact  gaggggaggc  agcagcagcc  atctagagga  gctagaactt      7380
tgggaacagt  ggaataaggc  tggcatgttg  gcatgaggag  tagcagggca  aagcaggagt      7440
gcagattcta  gagcctggct  acatgggttc  aaatcccagc  tctgtcactc  aggaactggg      7500
agattttgat  caagacactt  aacctctttg  gcctcagtct  ccttgtctgt  aaaatggggg      7560
taaataacag  cacaaacgtt  tcttattata  catacgagaa  aactgaggtc  gagagaagct      7620
aagtaatttg  tccaaggtca  cacagccagt  cagggatgga  gctgggattt  gaacccacag      7680
tctcagagtt  tagctcttgc  atcttactac  ttattgggat  gaagcctgag  ctgagatctg      7740
caccctagac  ctctccccac  aagccagggc  cggtagactg  gcacaggcct  gggccactca      7800
cttgaggaag  tcctctggct  cttcgaagac  cttctcacat  ccgggccact  tgcagacacc      7860
atttgccagc  agtgggtagg  agctctgggg  cacagccgaa  agggtgctgg  ggggacagag      7920
ggtgtcaggg  gaggggatag  gagggcgagg  atccttccca  gccctgtcca  ctgacctgtc      7980
cttcctgggt  gcactgggat  ttgggaaggt  gcagagcagt  gccggctccc  tggacaccca      8040
ttccaggctg  gccacgttga  tccctgtggg  tggggacagg  gcacctatgg  aggctgtggg      8100
ctgggctctg  gagcttggcc  cacaaggcct  ctcattttga  gcttccacc   ctcctgagcc      8160 tcgaaaccc   tgactcccag  ggggctctgc  tgtccccaaa  gtcccaggct  tctggcagag      8220
aagcttaaag  acggccattc  gcaggtgctg  acattttgac  tagctttgta  aagctctgtg      8280
gttttgtgat  tttgacattc  tgcatcttta  aggttctgca  cctgacgttt  tttggagggt      8340
ggagtttcca  agcctctgag  acctgacacc  tttgaccccc  agagtactgc  aattcagaat      8400
agcctacact  gctcacagcc  aaggatctgg  ggacttgggg  gttctgtgaa  gccatggggt      8460
acgggctgag  gtgttaccag  gtgggaggcc  aggccgggcc  ttgagggaga  agaccccagt      8520
ggcggtggtg  ggtggtgtga  ggctgatcat  ggctgggctc  tccaggggggt  gcacctgcag     8580 cacagggggtc  cgggcgtggg  catccaccgt  tgagagctgg  ggggcacatg  tgggctgtgg     8640
ttcagcctga  ctcggggccc  ctccccacag  ttctcccacc  tgctccctcc  tcctgcccca     8700
ttcaccgtcc  atacctggtg  catgaaatgt  ggcctgtcct  ggaggagtgc  ctgtaagtgg     8760
ggcaaggggc  ccagccgtgc  cccggagggt  gccaccatga  ctaggggcag  tgtgggcagc     8820
tgggcagaaa  ggcaggtggg  tgagaggcca  tcctgatcct  cactgttctg  tgtctaattc     8880
aaatactctg  cactgcaagc  ccacatggta  gatgctatga  tcatccccct  tttacacgta     8940
```

```
tggaaactga ggctcatgga gatcgagtaa cttttttaaag atcaaacagc taataagttg      9000
cagagctggc ctcagccctg tcacctcacc tacttggccc cagtcctctt ctcttgtcac      9060
atggggatgg ggacacatag ctatgctcat gggactacaa tacggcctcc tcctctcctg      9120
agacagggat tgggaggtcg gggagagcct ccaatctctg aggcctggca ggtgggatt      9180 ttcttggccc tgcaacatct gcataagtca cagacttgcc tgggacccag aaaccacttc      9240
ctgtgcccca gccagccccc ctcccgccca gtgccacagt aaaggtcggc acctgtaggt      9300
ccaggtaccc caccctgcct gccccatcct gggcccaggg cctcacctgc agctgcgatg      9360
gtggcatggg gttcaaggaa gaagaggagg catgggcccc gcctcgaaga tctcggccct      9420
ggaaggttcc ccctgggccc cgggccccca gcaggtctga ggctttgggt gcagccctcc      9480
agctgggcga ggctcctggg gatgggccaa gggccaagga aggggccgag ggcttgccag      9540
gcctggggtt gggcatcggg tccttgtcca agggcaggct gcgtagacaa taggggaaag      9600
gagtcacacg tgtgctaggg cggtatgaga tactcgacca cctgagccac gtggacactc      9660
ctctggtcaa agcaggcatt ggctgggaca tgtcccgagg ggccccatag ttgcacccca      9720
gctctagaca cacacacaca cacacacaca cacacacacc aagaacacag gtacatgtac      9780
atacccacac atgccccacg tgcagaggtc cagcacctgg cttgcctgcc cacgctagca      9840
cagccctggt gtggatgtgt cctctatgag ggcaatggtt gtttcccct ccacttgaga      9900 gctgtttcaa gcctcaggcc tctagccctc cctgcaccct gcacaggctg tgtttgctca      9960
tcttgccgga gctggtctcg gactttctcc tcggagtcct attttgcccc agtgactagg    10020
catggactca aaagattcat ctggctgctg tgagtggggc tagtgaggag gctattgtaa    10080
cagtcctggc aagtgatgat gctggcacag aatgggctgg tggcagtgga gaaggcgaga    10140
agtgggtaga ttctgagact taatctgaag ctggatcagg agcagtgcta gcagcttgga    10200
tgtagtgggc aagagggaga gtcaaagtga catgggtttt agcttgagca gctggaagga    10260
ccgagctgac attacctgag atgggggaca tggcgggggag ttggattggg tgcaaaagtg    10320
caggtgtaga tagacatgaa gagtctggca ttaaatatgt gagtggagga gctgaggggg    10380
cagctgaata cggggtctg gatctcaggg caaggaggcg agtccaggag tgtgatcatg    10440
cacggatcca gcatggcaag tgacagagag gaggagagat ggggtctctt gagctggggc    10500
ctgtagaagc ttctctaccc agcccccatc agagttcacc ccaatttctg gccctcaagc    10560
ctggctcatg ctacacccccc tgcctcaaat gcccactcct tctcctcttt ccctgtccaa    10620
gccacgcaag acctgctctt ctattgtcct caccttgaaa gccctccaca atggctccgg    10680 gcccctgct gagccccaga accttccact ccctgaggga agcactggct tttcaggatc    10740
ctataatcct ggtctgagag gaagccgag ctggaaggga ctgcccagcc aaccccatta    10800
tacagaaggg gatgctcaga tgccgagttc cgtagtccca tagtgacttg agaactccac    10860
ttctttcttt aggaagtgtt tccgtgtgca cattttataa actctctggt gtgtgtgtgt    10920
gtgtgtctcc atctccccgt tccacctcac agcactgagt tgggcacaca gctgctgaga    10980
gcagcccggg ggagtataga agggttctgg gggagcagtt gctccttcct ttctttgctg    11040
tcacctcctg ggggtggttg tcagagctgt ggtgctgagg gagatgagtg tgagaatcca    11100
ggtattaagt tcttagtctc ctgggggctt agaacattac tgcgtgagaa acaggagtgt    11160
gggtctgtgg aggctccgaa caagggcctg ggagagcact ggtgagatga gaaggtgagt    11220
gaatgaatga agccagagat ggggtgatgc tccttcaagc caagaaataa caaagattgc    11280
```

-continued

```
cagcaaccac cagaagctgg gggagaggcc tggagcagct tctcccttat ggcccccaga   11340
aggaaccaac cctggcaaca ccttgatctt ggactctggc ctccagaact gtgagatgat   11400
caatttctgt tgctgaagcc actcagttgt ggtactttgt tatagcagcc agaacaaact   11460
aataccgatt tcggtgcaaa tggatgtttt ccaccactct ggcctggccc atgtggctgg   11520
cctgtggtca cttctgaagc tgcctggaca cttggccaga gctaagaatt ctccccaaac   11580
acatgtggga tggcctgact cagcaaagca tagatacatt ctcagacagg gacatggaga   11640
tgatctgtct gggggtagag gacctagagg gccgggctgg gcagccggct tcctgcactg   11700
tctgttggga cgtccctttc tgactgggtt tctcagaagc tgaatggggg atgtttctgg   11760
gacacagatt atgtttttcat atcggggtct gcatctgggc cctgttgtca cagcccccga   11820
cttgcccaga tttttccgcc attgacgtca tggcggccgg atgcgccggg cttcatcgac   11880
accacggagg aagagaagag ggcagatacc ccaccccaca ggtttcgttc cgagaactgg   11940
ctgccctgtc ctgcagcagg cttggcccag gtggggtgac atgggtgctg gtggatgtgg   12000
taggtgatgt ccatctggcc actatgacaa gcccctagct ctgaagacct ggcccttctt   12060
gggttgtgga gaggacccag gtttgaagct ctgagagtgc caggcaggct ccacagatac   12120
tgggacccct ggggtcttca aatagtataa caccaggacc tcagaatcat agaacagcat   12180
ttcttagatt taaaggatcc tagaatctca aaaccacaga ctgtggggtc tacggtccca   12240
aagtctcagt atgtgtaggc cagtgtccct ggtgtccaaa ctccttggaa ccatctgaaa   12300
gtcaggcagc ttgctgcttc atagggcctc ttgcctacca ggcctggaaa cagagccagc   12360
ctccctaggg cctcagtctc cctgtccact ctggaacaac gttcccaaat acatggccac   12420
tccgccagag atggcaacag ggggaggagg aggttgaggc tggtgtgcct ttggtctggg   12480
cctcatgggg ggagctggaa aagcctcagc cttcgccaat acagagccca tcatcagact   12540
ctctagaggg gccccacaat caaggttttc ggggaccagc accagctctg gggacacaca   12600
gcctgactga ctgacatgcc tccatcatca ccacgctctg gccaactagg cctcctgacc   12660
tatggagtcc ggggcctcac ctagcccagc tcttgtgagg ctgggcccca cactgtgatc   12720
gtggatcgtc caacctgtgg gaagttgggg tccaacgtgt gagaaggcag aagggggaat   12780
ggtagcccag gttccccttc cccttctgg gtgctgaggg gtaaactgag gcctgcagtt   12840
ggggagagag ccagaaccag ggtcccacct agagtcctga gatctaggct tggatttcaa   12900
ctctgccgct gcatttcggt gaggccctga gatctctggt cttcaatttg cccttctaca   12960
ctgagcacgg agaggcgtgg agtagacaag ggccagggcc cttctacgct gtctggttaa   13020
gtcattaggt gtctgcaggg cttcaagttg acaattgccc ctctatccag gggactggct   13080
gagagatagg gatacataga gacaaagaga cacacacaaa gagcgagcaa gagagaacaa   13140
gagatagtga gagacattga gagaaatgga cacatgcatg gagagccaga gtgcatgtgt   13200
gcgagaggag gattgcctca aataagaaca tttgctggtc tctggctggt tcaactgatg   13260
ctgcctgaaa taatcaagaa taaagaaggg caaggtgcca gggacaccca tggctgggta   13320
ttgaattgta ttgcaaagca acaatcagca aaacagtgtg gccctggtat aagaacagat   13380 actgggaag agaacagaat agaaagcttg gacatggacc cacatatgga gagaactgaa   13440
tttgtgatga atgtggcatt tcaaactgga ggaccatgga gtatggttta acaaatgtgt   13500
ctgagataat tagggagaag ataaagttat tgagtgaata gtcagtccat tatcccaaca   13560 accctccct gcccagtttg aaatgtcacc atcatcatat accctaaaat gcccagatcc   13620
attcaagata taagttttaa cacctaatgc tgatcttggg tttattgtgt gtcaggcctt   13680
```

-continued

```
gtgctaagta tttactgtgg ttaaaaattt taatctaaac aaagactcct gaggaaggta   13740
ctattataac cattgcagta catatgagga aatggaggta tggagaggtt aagtgcctgg   13800
ctaaaaatca cacatagggc ttggggtgac gctgggtttg tcccagacag tctggctcca   13860
gtacccacac tcttaacctc tatagtaaat ggaaaaaatg aagccataaa agagactaga   13920
agccaacata ggtgaacatt tatctcattt tcaagtagga aaggactttc taagcacaaa   13980
accagagaca gaagccacag aaaaaaagac taacctattt gactgtataa aaccatcata   14040
agcatcacaa aaaacaccat aaacaaatag aaaaaaagca aatgatgaat tggggaaaat   14100
atttgctata tatgtaatgg ctgatgaaag gttaataacc attccaaata aagagctgtg   14160
gcaaatcaat aagggaaaaa taagatgaac accctattag gagtaaggac atgaccagac   14220
aaccaaaaaa aaaaaaaaaa aagcatgaat ggccaatgaa tagtaaaagt aatcacaaga   14280
tgcaaatttc aacaatgtga taatgtgttt ttcttacctg tcatgttggg aaataattaa   14340
aacataataa tactcaccta gggttagctt aagtagaggg agcataaaat aggacaacct   14400
tttggaagga gaattagcag agagggtcat aaactttaaa aatgcacgcc ccctttgccc   14460
cagcaactcc cttttcagga atccaaggaa gcagtcaggg atgtttatag aaaaaaacga   14520
gaaacaaccg gaatgtccaa caatcggcac ttggtcaaat caatcaaagt tcatgctgat   14580
gtgaggacag tcttgtccat catgaaagat catgtgttca aacaattttt agtaagcttc   14640
aaaaacacta ctgttaattg aataaagcag gaacaaaacc aatatatagc atgattctaa   14700
tttggttaca gaaatactaa tagctaacac ttcgtgagca cttactttgt gccaaacgct   14760
gtgctaagcc tgcagaatcg agctcacccc agccctgaac aacctgtttg cttcctgaat   14820
atggactctg gtcacacaca tgcagtcctg gggtaggtcc acacagctaa actacggttg   14880
acaatggtgt gaagtgctcc ctgcccccc gccccaaggg tctcctctaa agcgatacaa   14940
gcaaagttca gttaagtgct cagcttgccc cggcaccttg caatcctcct gctactaggg   15000
tgaacagaac tgatgctcac tctcataaaa tgtaaaggtc ctcggcgaca ttactattat   15060
taaacgccag ctgtgtacaa agctctaggc tggatgctgg ctgggaaggc aggtgggga   15120 aggcaagaaa agagagcggg agagatggag gaaaggagat cgatggagtg tggtcaagat   15180
ggaggagaca gagatagggg agatggtcag aggccaggag agatgcgggg aaagagagtc   15240
tgagtgtagc gacagacaga tggcgggaga aagagaggca gagaaacatg taaaagagca   15300
agacagggtg agcagagaga cagagaagga tgagaggcat caagagctaa gagacaaaga   15360
gatgagagag atgcagttga aattttcagt tgcacctgga cagcatttca agttgttcaa   15420
agctctgaaa tccataaaga ctggcagctg acatatttta aaaatcctat ccatctacgt   15480
atcaattgat gaattcattt attttttgccc ctgcccatgc attaagtact tcacctttaa   15540
gtcttctgcc atttattcta ttattttttt aaagacctta cctggctgga atcacggtag   15600
ctgggtacat cccactgtac cagagggccc ctgaccccc cgccgtgcct acctccctgc   15660
catctcctcc aatggggccc acatctggta ggggagagca gggacactca ccttggtgaa   15720
gtggactgac agaaaaggat cagcctggct tgtgggaaac tgtcacgtat caaaaacaac   15780 tttgcttta taccgagaag aaaaaccacg ctgtacggtg tggaagccgc agacctctct   15840
cttctaataa tccaaatttt tttcgatgag tgtgtgcgct gataatcacg gggtggggag   15900
gggttctcat agttttttttt ttctctctct ctgtgtttct cctttctctg attatgagac   15960
ttaaacggaa attttgaaat tttgggtttt tttctttgcc ctttacgagt catctgaaaa   16020
```

-continued

```
tatgatttct tcccctcacc acagaggtga gaggtatcaa tgagataata gggctcatga   16080
gaaaccacag tttttaaaac aaaagtgtat agagtttgaa aaaaaaaaaa caagggaaaa   16140
gaactaaaat aaatcacagg gccaacccga ggcaggcaga gacaccattc tgtgagtgag   16200
aggatatttg agggtctctg gggaaagaaa gagaatctga agctctatgt gtggatggga   16260
aatgccaggg aaagagacag aatagggctg ggttcccaga ggcctcgccc tactccaggc   16320
ctcagtttcc ctatagatgg aattgatatg gtccccattg cttgaactac ccggcgaggg   16380
gagttctgca ccccctgcaa cacccctccc acagagggtg aggggcatgt aagttacttc   16440
atggaggaga aagcggagag cccactgtca tcccctaaaa ttcatggact tgaagagtcg   16500
gagaatccct ggctcccaga atctactgac agttactgaa tgaggaaaga gagaaaagtc   16560
tcgcctcatc acgttttagg gcttgagtgc cctgacccag ccactgtccc actgggaagg   16620
tccctagcag gtccccaata ttaatgcatc catcctcacg atgaacccca gaggcccatt   16680
gggaccctga ccctcttgtt tcaggaacat catggcctga tgcttctgag gccctcagcc   16740
tttggggtct tttacttcaa aaagccccag tttccaagga tttaggattc caaatatccg   16800
ccatcatctc agtagctgat gtttatcttg aattttccat gggtcagata cagtgctgaa   16860
catgtctcac aagtgatcat gttcaatcct caccatggcc ccttgagctc catctcatca   16920
ttattgtatt cctgttatac agatgaggga aacggaggta taagtagtca agcaacttgc   16980
ccaagatcac agagctggcg agtgtgggtc ccgctttctt tggtgctggg ctttgaaatc   17040
cccaagcttt cctgaacttg atgttctcag gttttaaatt ctaggatgtg atggcaggga   17100
gatcctggga tttggagagt ccttggagac ttgaagcttg tgaggctttt aggttgtcca   17160
ggaattggcg gctgcatctc ttgacctcag caggcactct attcaaccac tggtcagcat   17220
ggtagaccag cccccagggg cttctcctga caggccatgg tgaagacttc cagctcccag   17280
caccctgcaa agcccagggt tctagtcgtc caacaaccac tccagccctc tacaagactg   17340
gcttcagacc tggggaagag aaattggaaa gggcttttta tttacatggt acaaatctgg   17400
tggccaagat ccacccctc accccttgc cccctttcct cccccaacct t             17451
```

```
<210> SEQ ID NO 3
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 3
ttcgaagacc ttctcac                                                    17

<210> SEQ ID NO 4
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 4
gaagatggtc cgcctgg                                                    17

<210> SEQ ID NO 5
<211> LENGTH: 17
<212> TYPE: DNA
<213> ORGANISM: Artificial Sequence
<220> FEATURE:
<223> OTHER INFORMATION: Antisense oligonucleotide
```

-continued

<400> SEQUENCE: 5
cagaagatgg tccgcct                                                                                   17

<210> SEQ ID NO 6
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 6
tccagaagat ggtccgc                                                                                   17

<210> SEQ ID NO 7
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 7
atccagaaga tggtccg                                                                                   17

<210> SEQ ID NO 8
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 8
cttgtcggat gatgcc                                                                                    16

<210> SEQ ID NO 9
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 9
ctacgatgca gcaggag                                                                                   17

<210> SEQ ID NO 10
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 10
cgtggcgtag gtgaaag                                                                                   17

<210> SEQ ID NO 11
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 11
atgagcgtgg cgtaggt                                                                                   17

<210> SEQ ID NO 12

-continued

```
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 12
atgagcgtgg cgtagg                                                    16

<210> SEQ ID NO 13
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 13
gatgagcgtg gcgtagg                                                   17

<210> SEQ ID NO 14
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 14
atgagcgtgg cgtag                                                     15

<210> SEQ ID NO 15
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 15
gatgagcgtg gcgtag                                                    16

<210> SEQ ID NO 16
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 16
ggatgagcgt ggcgtag                                                   17

<210> SEQ ID NO 17
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 17
ggatgagcgt ggcgta                                                    16

<210> SEQ ID NO 18
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 18
```

-continued

```
cggatgagcg tggcgta                                                   17

<210> SEQ ID NO 19
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 19
ccagcggatg agcgtg                                                    16

<210> SEQ ID NO 20
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 20
cagtggtaga tctcatt                                                   17

<210> SEQ ID NO 21
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 21
gactcaggtt gtggcgg                                                   17

<210> SEQ ID NO 22
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 22
gcggaactcc agctcat                                                   17

<210> SEQ ID NO 23
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 23
cgctgcttct gtgtagg                                                   17

<210> SEQ ID NO 24
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 24
tgagcgagca cgtgttg                                                   17

<210> SEQ ID NO 25
<211> LENGTH: 17
<212> TYPE: DNA
```

-continued

<213> ORGANISM: Artificial Sequence
<220> FEATURE:
<223> OTHER INFORMATION: Antisense oligonucleotide

<400> SEQUENCE: 25
gccgtgtgtg tgagcga                                                                           17

<210> SEQ ID NO 26
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 26
gcgtgagata cacaggt                                                                           17

<210> SEQ ID NO 27
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 27
agctcggctg cagttta                                                                           17

<210> SEQ ID NO 28
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 28
gatcgatgga gtgtggt                                                                           17

<210> SEQ ID NO 29
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 29
tcggcgacat tactatt                                                                           17

<210> SEQ ID NO 30
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 30
cctcggcgac attact                                                                            16

<210> SEQ ID NO 31
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 31
gtccaacaat cggcact                                                                           17

-continued

```
<210> SEQ ID NO 32
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 32
cgtggatcgt ccaacct                                                        17

<210> SEQ ID NO 33
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 33
tcgtggatcg tccaac                                                         16

<210> SEQ ID NO 34
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 34
cacaggtttc gttccga                                                        17

<210> SEQ ID NO 35
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 35
gcttcatcga caccacg                                                        17

<210> SEQ ID NO 36
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 36
tttccgccat tgacgtc                                                        17

<210> SEQ ID NO 37
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 37
tttcgttccg agaact                                                         16

<210> SEQ ID NO 38
<211> LENGTH: 17
<212> TYPE: DNA
<213> ORGANISM: Artificial Sequence
<220> FEATURE:
```

-continued

<223> OTHER INFORMATION: Antisense oligonucleotide

<400> SEQUENCE: 38
tcagatgccg agttccg                                                          17

<210> SEQ ID NO 39
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 39
ccgagttccg tagtcc                                                           16

<210> SEQ ID NO 40
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 40
gatcatgcac ggatcca                                                          17

<210> SEQ ID NO 41
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 41
cggactttct cctcgga                                                          17

<210> SEQ ID NO 42
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 42
gatactcgac cacctga                                                          17

<210> SEQ ID NO 43
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 43
gtatgagata ctcgacc                                                          17

<210> SEQ ID NO 44
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 44
acggccattc gcaggtg                                                          17

<210> SEQ ID NO 45
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 45
aagacggcca ttcgcag                                                17

<210> SEQ ID NO 46
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 46
aagacggcca ttcgca                                                 16

<210> SEQ ID NO 47
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 47
gtgcggatgt cgtatgt                                                17

<210> SEQ ID NO 48
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 48
caggtgcgga tgtcgta                                                17

<210> SEQ ID NO 49
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 49
caggtgcgga tgtcgt                                                 16

<210> SEQ ID NO 50
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 50
ttaggtgtgg cgctagg                                                17

<210> SEQ ID NO 51
<211> LENGTH: 16
<212> TYPE: DNA
<213> ORGANISM: Artificial Sequence
<220> FEATURE:
<223> OTHER INFORMATION: Antisense oligonucleotide -continued

```
<400> SEQUENCE: 51
gttcagagac agtcgg                                                16

<210> SEQ ID NO 52
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 52
gttcggtgtg gagtga                                                16

<210> SEQ ID NO 53
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 53
tcgagtatct tacgtg                                                16

<210> SEQ ID NO 54
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 54
cgagtatctt acgtg                                                 15

<210> SEQ ID NO 55
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 55
gtcgcatgtt gtggaac                                               17

<210> SEQ ID NO 56
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 56
gagcgagcac gtgttgg                                               17

<210> SEQ ID NO 57
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 57
gtgagcgagc acgtgtt                                               17

<210> SEQ ID NO 58
<211> LENGTH: 17
```

```
<212> TYPE: DNA
<213> ORGANISM: Artificial Sequence
<220> FEATURE:
<223> OTHER INFORMATION: Antisense oligonucleotide

<400> SEQUENCE: 58
cgtgagatac acaggtg                                                      17

<210> SEQ ID NO 59
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 59
atgcgtgaga tacacag                                                      17

<210> SEQ ID NO 60
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 60
tcgatggagt gtggtca                                                      17

<210> SEQ ID NO 61
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 61
agatcgatgg agtgtgg                                                      17

<210> SEQ ID NO 62
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 62
cctcggcgac attacta                                                      17

<210> SEQ ID NO 63
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 63
ctcggcgaca ttacta                                                       16

<210> SEQ ID NO 64
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 64
```

-continued

```
gctaaactac ggttgac                                                17

<210> SEQ ID NO 65
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 65
gtttcgttcc gagaact                                                17

<210> SEQ ID NO 66
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 66
aggtttcgtt ccgagaa                                                17

<210> SEQ ID NO 67
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 67
gatgccgagt tccgtag                                                17

<210> SEQ ID NO 68
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 68
agatgccgag ttccgta                                                17

<210> SEQ ID NO 69
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 69
gtgatcatgc acggatc                                                17

<210> SEQ ID NO 70
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 70
ttaaagacgg ccattcg                                                17

<210> SEQ ID NO 71
<211> LENGTH: 17
<212> TYPE: DNA
<213> ORGANISM: Artificial Sequence
```

-continued

```
<220> FEATURE:
<223> OTHER INFORMATION: Antisense oligonucleotide

<400> SEQUENCE: 71
aggtgcggat gtcgtat                                                          17

<210> SEQ ID NO 72
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 72
gtgcggatgt cgtatg                                                           16

<210> SEQ ID NO 73
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 73
aggtgcggat gtcgta                                                           16

<210> SEQ ID NO 74
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 74
acaggtgcgg atgtcg                                                           16

<210> SEQ ID NO 75
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 75
gttaggtgtg gcgctag                                                          17

<210> SEQ ID NO 76
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 76
gaaaaaccac gctgtacg                                                         18

<210> SEQ ID NO 77
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 77
atccagaaga tggtccgc                                                         18
```

-continued

```
<210> SEQ ID NO 78
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 78
cgtggcgtag gtgaaagg                                                    18

<210> SEQ ID NO 79
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 79
ggatgagcgt ggcgtagg                                                    18

<210> SEQ ID NO 80
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 80
tgcggaactc cagctcat                                                    18

<210> SEQ ID NO 81
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 81
gaagtaatct gtgcgagc                                                    18

<210> SEQ ID NO 82
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 82
gttgtttgag tgtactga                                                    18

<210> SEQ ID NO 83
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 83
gtgagcgagc acgtgttg                                                    18

<210> SEQ ID NO 84
<211> LENGTH: 18
<212> TYPE: DNA
<213> ORGANISM: Artificial Sequence
<220> FEATURE:
<223> OTHER INFORMATION: Antisense oligonucleotide
```

<400> SEQUENCE: 84
tgtgagcgag cacgtgtt                                                           18

<210> SEQ ID NO 85
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 85
ggccgtgtgt gtgagcga                                                           18

<210> SEQ ID NO 86
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 86
aattctaaca ggccgtgt                                                           18

<210> SEQ ID NO 87
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 87
gtgaattcta acaggccg                                                           18

<210> SEQ ID NO 88
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 88
tatgcgtgag atacacag                                                           18

<210> SEQ ID NO 89
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 89
catatgcgtg agatacac                                                           18

<210> SEQ ID NO 90
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 90
ctcggctgca gtttattg                                                           18

<210> SEQ ID NO 91

-continued

```
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 91
agaaaaacca cgctgtacg                                              19

<210> SEQ ID NO 92
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 92
tcgcatgttg tggaacttg                                              19

<210> SEQ ID NO 93
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 93
gcgtggcgta ggtgaaagg                                              19

<210> SEQ ID NO 94
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 94
agcgtggcgt aggtgaaag                                              19

<210> SEQ ID NO 95
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 95
gagcgtggcg taggtgaaa                                              19

<210> SEQ ID NO 96
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 96
tgagcgtggc gtaggtgaa                                              19

<210> SEQ ID NO 97
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 97
```

-continued atgagcgtgg cgtaggtga                                                                                                        19

<210> SEQ ID NO 98
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 98
atctcattga gtgtccgct                                                                                                          19

<210> SEQ ID NO 99
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 99
gatctcattg agtgtccgc                                                                                                          19

<210> SEQ ID NO 100
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 100
ggctccgttt cttgcggaa                                                                                                          19

<210> SEQ ID NO 101
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 101
cgctgcttct gtgtaggcc                                                                                                          19

<210> SEQ ID NO 102
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 102
gaattctaac aggccgtgt                                                                                                          19

<210> SEQ ID NO 103
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 103
atgcgtgaga tacacaggt                                                                                                          19

<210> SEQ ID NO 104
<211> LENGTH: 19
<212> TYPE: DNA

-continued

<213> ORGANISM: Artificial Sequence
<220> FEATURE:
<223> OTHER INFORMATION: Antisense oligonucleotide

<400> SEQUENCE: 104
tatgcgtgag atacacagg                                                            19

<210> SEQ ID NO 105
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 105
atatgcgtga gatacacag                                                            19

<210> SEQ ID NO 106
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 106
gtgcatatgc gtgagatac                                                            19

<210> SEQ ID NO 107
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 107
gctcggctgc agtttattg                                                            19

<210> SEQ ID NO 108
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 108
ggagctcggc tgcagttta                                                            19

<210> SEQ ID NO 109
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 109
cctcggcgac attactat                                                             18

<210> SEQ ID NO 110
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 110
cgtggatcgt ccaacctg                                                             18

-continued

```
<210> SEQ ID NO 111
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 111
agatgccgag ttccgtag                                                18

<210> SEQ ID NO 112
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 112
cttaaagacg gccattcg                                                18

<210> SEQ ID NO 113
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 113
aggtgcggat gtcgtatg                                                18

<210> SEQ ID NO 114
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 114
caggtgcgga tgtcgtat                                                18

<210> SEQ ID NO 115
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 115
ggttaggtgt ggcgctag                                                18

<210> SEQ ID NO 116
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 116
attatcgagt atcttacg                                                18

<210> SEQ ID NO 117
<211> LENGTH: 19
<212> TYPE: DNA
<213> ORGANISM: Artificial Sequence
<220> FEATURE:
```

-continued

<223> OTHER INFORMATION: Antisense oligonucleotide

<400> SEQUENCE: 117
aggagatcga tggagtgtg                                                                          19

<210> SEQ ID NO 118
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 118
cctcggcgac attactatt                                                                          19

<210> SEQ ID NO 119
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 119
ggtctcctct aaagcgata                                                                          19

<210> SEQ ID NO 120
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 120
ggtaggtcca cacagctaa                                                                          19

<210> SEQ ID NO 121
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 121
aacaatcggc acttggtca                                                                          19

<210> SEQ ID NO 122
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 122
tgtgcgagag gaggattgc                                                                          19

<210> SEQ ID NO 123
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 123
cacgctctgg ccaactagg                                                                          19

<210> SEQ ID NO 124
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 124
gccttcgcca atacagagc                                                                   19

<210> SEQ ID NO 125
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 125
ctcagtatgt gtaggccag                                                                   19

<210> SEQ ID NO 126
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 126
cgttccgaga actggctgc                                                                   19

<210> SEQ ID NO 127
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 127
tcgttccgag aactggctg                                                                   19

<210> SEQ ID NO 128
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 128
tttcgttccg agaactggc                                                                   19

<210> SEQ ID NO 129
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 129
gtttcgttcc gagaactgg                                                                   19

<210> SEQ ID NO 130
<211> LENGTH: 19
<212> TYPE: DNA
<213> ORGANISM: Artificial Sequence
<220> FEATURE:
<223> OTHER INFORMATION: Antisense oligonucleotide -continued

```
<400> SEQUENCE: 130
acaggtttcg ttccgagaa                                              19

<210> SEQ ID NO 131
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 131
cacaggtttc gttccgaga                                              19

<210> SEQ ID NO 132
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 132
ccacaggttt cgttccgag                                              19

<210> SEQ ID NO 133
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 133
tttcggtgca aatggatgt                                              19

<210> SEQ ID NO 134
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 134
aggaccgagc tgacattac                                              19

<210> SEQ ID NO 135
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 135
atactcgacc acctgagcc                                              19

<210> SEQ ID NO 136
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 136
atgagatact cgaccacct                                              19

<210> SEQ ID NO 137
<211> LENGTH: 19
```

```
<212> TYPE: DNA
<213> ORGANISM: Artificial Sequence
<220> FEATURE:
<223> OTHER INFORMATION: Antisense oligonucleotide

<400> SEQUENCE: 137
cattcgcagg tgctgacat                                                      19

<210> SEQ ID NO 138
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 138
aaagacggcc attcgcagg                                                      19

<210> SEQ ID NO 139
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 139
gtacattcgc atcatgaga                                                      19

<210> SEQ ID NO 140
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 140
gtgcggatgt cgtatgtgg                                                      19

<210> SEQ ID NO 141
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 141
aggtgcggat gtcgtatgt                                                      19

<210> SEQ ID NO 142
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 142
caggtgcgga tgtcgtatg                                                      19

<210> SEQ ID NO 143
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 143
```

-continued

```
acaggtgcgg atgtcgtat                                                19

<210> SEQ ID NO 144
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 144
agcatgagcc gtatttatt                                                19

<210> SEQ ID NO 145
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 145
gatggccgaa tatagtagc                                                19

<210> SEQ ID NO 146
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 146
tgtggcgcta ggatgaagg                                                19

<210> SEQ ID NO 147
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 147
ggttcggtgt ggagtgagg                                                19

<210> SEQ ID NO 148
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 148
ttatcgagta tcttacgtg                                                19

<210> SEQ ID NO 149
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 149
cttcgaagac cttctcac                                                 18

<210> SEQ ID NO 150
<211> LENGTH: 18
<212> TYPE: DNA
<213> ORGANISM: Artificial Sequence
```

-continued

<220> FEATURE:
<223> OTHER INFORMATION: Antisense oligonucleotide

<400> SEQUENCE: 150
agaagatggt ccgcctgg                                                      18

<210> SEQ ID NO 151
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 151
catccagaag atggtccg                                                      18

<210> SEQ ID NO 152
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 152
ctacgatgca gcaggagc                                                      18

<210> SEQ ID NO 153
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 153
gccagcagct acgatgca                                                      18

<210> SEQ ID NO 154
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 154
gtgcctccgg acagcaaa                                                      18

<210> SEQ ID NO 155
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 155
tcgcatgttg tggaactt                                                      18

<210> SEQ ID NO 156
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 156
gcgtggcgta ggtgaaag                                                      18

-continued

```
<210> SEQ ID NO 157
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 157
agcgtggcgt aggtgaaa                                                  18

<210> SEQ ID NO 158
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 158
tgagcgtggc gtaggtga                                                  18

<210> SEQ ID NO 159
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 159
atgagcgtgg cgtaggtg                                                  18

<210> SEQ ID NO 160
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 160
cggatgagcg tggcgtag                                                  18

<210> SEQ ID NO 161
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 161
gcggatgagc gtggcgta                                                  18

<210> SEQ ID NO 162
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 162
agcggatgag cgtggcgt                                                  18

<210> SEQ ID NO 163
<211> LENGTH: 18
<212> TYPE: DNA
<213> ORGANISM: Artificial Sequence
<220> FEATURE:
<223> OTHER INFORMATION: Antisense oligonucleotide
```

-continued

<400> SEQUENCE: 163
cagcggatga gcgtggcg                                              18

<210> SEQ ID NO 164
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 164
atctcattga gtgtccgc                                             18

<210> SEQ ID NO 165
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 165
agactcaggt tgtggcgg                                             18

<210> SEQ ID NO 166
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 166
tgaagtaatc tgtgcgag                                             18

<210> SEQ ID NO 167
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 167
tcggctgcag tttattgg                                             18

<210> SEQ ID NO 168
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 168
gaagaaaaac cacgctgta                                            19

<210> SEQ ID NO 169
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 169
ttggtgaagt ggactgaca                                            19

<210> SEQ ID NO 170

-continued

```
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 170
tcgaagacct tctcacatc                                           19

<210> SEQ ID NO 171
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 171
ttcgaagacc ttctcacat                                           19

<210> SEQ ID NO 172
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 172
tcatccagaa gatggtccg                                           19

<210> SEQ ID NO 173
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 173
ctacgatgca gcaggagcc                                           19

<210> SEQ ID NO 174
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 174
ggtgcctccg gacagcaaa                                           19

<210> SEQ ID NO 175
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 175
catgttgtgg aggaactct                                           19

<210> SEQ ID NO 176
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 176
```

-continued

```
tagtccatgt tgtggagga                                                    19

<210> SEQ ID NO 177
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 177
gatgagcgtg gcgtaggtg                                                    19

<210> SEQ ID NO 178
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 178
cggatgagcg tggcgtagg                                                    19

<210> SEQ ID NO 179
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 179
gcggatgagc gtggcgtag                                                    19

<210> SEQ ID NO 180
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 180
cagcggatga gcgtggcgt                                                    19

<210> SEQ ID NO 181
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 181
gcgtgtgaac cagtggtag                                                    19

<210> SEQ ID NO 182
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 182
actcaggttg tggcggatg                                                    19

<210> SEQ ID NO 183
<211> LENGTH: 19
<212> TYPE: DNA
```

-continued

<213> ORGANISM: Artificial Sequence
<220> FEATURE:
<223> OTHER INFORMATION: Antisense oligonucleotide

<400> SEQUENCE: 183
cttgtgcaga ctcaggttg                                                        19

<210> SEQ ID NO 184
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 184
tgcggaactc cagctcatc                                                        19

<210> SEQ ID NO 185
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 185
ttgcggaact ccagctcat                                                        19

<210> SEQ ID NO 186
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 186
tctggctccg tttcttgcg                                                        19

<210> SEQ ID NO 187
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 187
ctgaagtaat ctgtgcgag                                                        19

<210> SEQ ID NO 188
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 188
cctgaagtaa tctgtgcga                                                        19

<210> SEQ ID NO 189
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 189
gttgtttgag tgtactgag                                                        19

-continued

```
<210> SEQ ID NO 190
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 190
ggttgtttga gtgtactga                                            19

<210> SEQ ID NO 191
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 191
acgctgcttc tgtgtaggc                                            19

<210> SEQ ID NO 192
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 192
gacgctgctt ctgtgtagg                                            19

<210> SEQ ID NO 193
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 193
ggtactgacg ctgcttctg                                            19

<210> SEQ ID NO 194
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 194
tgtgagcgag cacgtgttg                                            19

<210> SEQ ID NO 195
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 195
gtgtgagcga gcacgtgtt                                            19

<210> SEQ ID NO 196
<211> LENGTH: 19
<212> TYPE: DNA
<213> ORGANISM: Artificial Sequence
<220> FEATURE:
```

<223> OTHER INFORMATION: Antisense oligonucleotide

<400> SEQUENCE: 196
ggccgtgtgt gtgagcgag                                                          19

<210> SEQ ID NO 197
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 197
tctaacaggc cgtgtgtgt                                                          19

<210> SEQ ID NO 198
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 198
aattctaaca ggccgtgtg                                                          19

<210> SEQ ID NO 199
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 199
tgaattctaa caggccgtg                                                          19

<210> SEQ ID NO 200
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 200
gtgaattcta acaggccgt                                                          19

<210> SEQ ID NO 201
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 201
ggtgaattct aacaggccg                                                          19

<210> SEQ ID NO 202
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 202
catatgcgtg agatacaca                                                          19

```
<210> SEQ ID NO 203
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 203
gttcctctgc agtctaagc                                                           19

<210> SEQ ID NO 204
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 204
gtagttcctc tgcagtcta                                                           19

<210> SEQ ID NO 205
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 205
ctcggctgca gtttattgg                                                           19

<210> SEQ ID NO 206
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 206
gtgtagcgac agacagat                                                            18

<210> SEQ ID NO 207
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 207
tcgatggagt gtggtcaa                                                            18

<210> SEQ ID NO 208
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 208
agatcgatgg agtgtggt                                                            18

<210> SEQ ID NO 209
<211> LENGTH: 18
<212> TYPE: DNA
<213> ORGANISM: Artificial Sequence
<220> FEATURE:
<223> OTHER INFORMATION: Antisense oligonucleotide
```

-continued

```
<400> SEQUENCE: 209
ctcggcgaca ttactatt                                              18

<210> SEQ ID NO 210
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 210
tcctcggcga cattacta                                              18

<210> SEQ ID NO 211
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 211
cctctaaagc gatacaag                                              18

<210> SEQ ID NO 212
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 212
gctaaactac ggttgaca                                              18

<210> SEQ ID NO 213
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 213
agctaaacta cggttgac                                              18

<210> SEQ ID NO 214
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 214
acaatcggca cttggtca                                              18

<210> SEQ ID NO 215
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 215
tcgtggatcg tccaacct                                              18

<210> SEQ ID NO 216
<211> LENGTH: 18
```

US 12,680,098 B2

-continued

```
<212> TYPE: DNA
<213> ORGANISM: Artificial Sequence
<220> FEATURE:
<223> OTHER INFORMATION: Antisense oligonucleotide

<400> SEQUENCE: 216
acgctctggc caactagg                                                   18

<210> SEQ ID NO 217
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 217
cttcgccaat acagagcc                                                   18

<210> SEQ ID NO 218
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 218
aatacatggc cactccgc                                                   18

<210> SEQ ID NO 219
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 219
tttcgttccg agaactgg                                                   18

<210> SEQ ID NO 220
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 220
gtttcgttcc gagaactg                                                   18

<210> SEQ ID NO 221
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 221
acaggtttcg ttccgaga                                                   18

<210> SEQ ID NO 222
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 222
```

-continued

```
ccacaggttt cgttccga                                                   18

<210> SEQ ID NO 223
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 223
gatcatgcac ggatccag                                                   18

<210> SEQ ID NO 224
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 224
ccgagctgac attacctg                                                   18

<210> SEQ ID NO 225
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 225
gtatgagata ctcgacca                                                   18

<210> SEQ ID NO 226
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 226
aagacggcca ttcgcagg                                                   18

<210> SEQ ID NO 227
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 227
gcttaaagac ggccattc                                                   18

<210> SEQ ID NO 228
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 228
gcgtgtgacc tatgtggt                                                   18

<210> SEQ ID NO 229
<211> LENGTH: 18
<212> TYPE: DNA
<213> ORGANISM: Artificial Sequence
```

-continued

```
<220> FEATURE:
<223> OTHER INFORMATION: Antisense oligonucleotide

<400> SEQUENCE: 229
```

```
gtacattcgc atcatgag                                              18
```

```
<210> SEQ ID NO 230
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 230
```

```
ggtgcggatg tcgtatgt                                              18
```

```
<210> SEQ ID NO 231
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 231
```

```
gagccgtatt tattagag                                              18
```

```
<210> SEQ ID NO 232
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 232
```

```
cagcatgagc cgtattta                                              18
```

```
<210> SEQ ID NO 233
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 233
```

```
cgtgtagtgc aaggacca                                              18
```

```
<210> SEQ ID NO 234
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 234
```

```
cgacactcga gaccatat                                              18
```

```
<210> SEQ ID NO 235
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 235
```

```
gatggccgaa tatagtag                                              18
```

```
<210> SEQ ID NO 236
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 236
gcggagtaac ttgcacac                                                              18

<210> SEQ ID NO 237
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 237
cacatttgag gcacggct                                                              18

<210> SEQ ID NO 238
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 238
gtgtggcgct aggatgaa                                                              18

<210> SEQ ID NO 239
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 239
ttaggtgtgg cgctagga                                                              18

<210> SEQ ID NO 240
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 240
ggttcggtgt ggagtgag                                                              18

<210> SEQ ID NO 241
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 241
cgagtatctt acgtgtca                                                              18

<210> SEQ ID NO 242
<211> LENGTH: 18
<212> TYPE: DNA
<213> ORGANISM: Artificial Sequence
<220> FEATURE:
<223> OTHER INFORMATION: Antisense oligonucleotide
```

-continued

<400> SEQUENCE: 242
tatcgagtat cttacgtg                                                       18

<210> SEQ ID NO 243
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 243
tacctggctg gaatcacgg                                                      19

<210> SEQ ID NO 244
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 244
cgtatcaatt gatgaattc                                                      19

<210> SEQ ID NO 245
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 245
tagcgacaga cagatggcg                                                      19

<210> SEQ ID NO 246
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 246
taaacgccag ctgtgtaca                                                      19

<210> SEQ ID NO 247
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 247
attaaacgcc agctgtgta                                                      19

<210> SEQ ID NO 248
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 248
ctcggcgaca ttactatta                                                      19

<210> SEQ ID NO 249

-continued

```
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 249
taaaggtcct cggcgacat                                              19

<210> SEQ ID NO 250
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 250
tcctctaaag cgatacaag                                              19

<210> SEQ ID NO 251
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 251
cggttgacaa tggtgtgaa                                              19

<210> SEQ ID NO 252
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 252
agctaaacta cggttgaca                                              19

<210> SEQ ID NO 253
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 253
aatcggcact tggtcaaat                                              19

<210> SEQ ID NO 254
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 254
acaatcggca cttggtcaa                                              19

<210> SEQ ID NO 255
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 255
```

-continued caacaatcgg cacttggtc                                                      19

<210> SEQ ID NO 256
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 256
aatagtcagt ccattatcc                                                      19

<210> SEQ ID NO 257
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 257
gtgcgagagg aggattgcc                                                      19

<210> SEQ ID NO 258
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 258
ggttaagtca ttaggtgtc                                                      19

<210> SEQ ID NO 259
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 259
cttctacgct gtctggtta                                                      19

<210> SEQ ID NO 260
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 260
cgtggatcgt ccaacctgt                                                      19

<210> SEQ ID NO 261
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 261
tcgtggatcg tccaacctg                                                      19

<210> SEQ ID NO 262
<211> LENGTH: 19
<212> TYPE: DNA

-continued

```
<213> ORGANISM: Artificial Sequence
<220> FEATURE:
<223> OTHER INFORMATION: Antisense oligonucleotide

<400> SEQUENCE: 262
atcatcacca cgctctggc                                                      19

<210> SEQ ID NO 263
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 263
ccttcgccaa tacagagcc                                                      19

<210> SEQ ID NO 264
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 264
agccttcgcc aatacagag                                                      19

<210> SEQ ID NO 265
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 265
cagccttcgc caatacaga                                                      19

<210> SEQ ID NO 266
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 266
tcagccttcg ccaatacag                                                      19

<210> SEQ ID NO 267
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 267
atagtataac accaggacc                                                      19

<210> SEQ ID NO 268
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 268
ttcatcgaca ccacggagg                                                      19
```

<210> SEQ ID NO 269
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 269
gcttcatcga caccacgga                                                        19

<210> SEQ ID NO 270
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 270
ttccgccatt gacgtcatg                                                        19

<210> SEQ ID NO 271
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 271
cagatgccga gttccgtag                                                        19

<210> SEQ ID NO 272
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 272
gctcagatgc cgagttccg                                                        19

<210> SEQ ID NO 273
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 273
gatcatgcac ggatccagc                                                        19

<210> SEQ ID NO 274
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 274
tgatcatgca cggatccag                                                        19

<210> SEQ ID NO 275
<211> LENGTH: 19
<212> TYPE: DNA
<213> ORGANISM: Artificial Sequence
<220> FEATURE:

<223> OTHER INFORMATION: Antisense oligonucleotide

<400> SEQUENCE: 275
gtgtttgctc atcttgccg                                                    19

<210> SEQ ID NO 276
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 276
gatactcgac cacctgagc                                                    19

<210> SEQ ID NO 277
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 277
tgagatactc gaccacctg                                                    19

<210> SEQ ID NO 278
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 278
tatgagatac tcgaccacc                                                    19

<210> SEQ ID NO 279
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 279
gtatgagata ctcgaccac                                                    19

<210> SEQ ID NO 280
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 280
gcggtatgag atactcgac                                                    19

<210> SEQ ID NO 281
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 281
agtgccacag taaaggtcg                                                    19

```
<210> SEQ ID NO 282
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 282
tcatggagat cgagtaact                                                 19

<210> SEQ ID NO 283
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 283
acggccattc gcaggtgct                                                 19

<210> SEQ ID NO 284
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 284
aagacggcca ttcgcaggt                                                 19

<210> SEQ ID NO 285
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 285
ttaaagacgg ccattcgca                                                 19

<210> SEQ ID NO 286
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 286
agcttaaaga cggccattc                                                 19

<210> SEQ ID NO 287
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 287
gaagcttaaa gacggccat                                                 19

<210> SEQ ID NO 288
<211> LENGTH: 19
<212> TYPE: DNA
<213> ORGANISM: Artificial Sequence
<220> FEATURE:
<223> OTHER INFORMATION: Antisense oligonucleotide
```

-continued

<400> SEQUENCE: 288
cgtgtgacct atgtggtta                                                      19

<210> SEQ ID NO 289
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 289
tgtacattcg catcatgag                                                      19

<210> SEQ ID NO 290
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 290
tctgtacatt cgcatcatg                                                      19

<210> SEQ ID NO 291
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 291
tgagccgtat ttattagag                                                      19

<210> SEQ ID NO 292
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 292
cagcatgagc cgtatttat                                                      19

<210> SEQ ID NO 293
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 293
acagcatgag ccgtattta                                                      19

<210> SEQ ID NO 294
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 294
ccgacactcg agaccatat                                                      19

<210> SEQ ID NO 295
<211> LENGTH: 19

-continued

```
<212> TYPE: DNA
<213> ORGANISM: Artificial Sequence
<220> FEATURE:
<223> OTHER INFORMATION: Antisense oligonucleotide

<400> SEQUENCE: 295
cgaatatagt agctggagt                                                              19

<210> SEQ ID NO 296
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 296
tctgatggcc gaatatagt                                                              19

<210> SEQ ID NO 297
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 297
agtggatagg tgagctcgg                                                              19

<210> SEQ ID NO 298
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 298
gcggagtaac ttgcacacc                                                              19

<210> SEQ ID NO 299
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 299
catttgaggc acggcttgg                                                              19

<210> SEQ ID NO 300
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 300
gtttggattt gcggacagg                                                              19

<210> SEQ ID NO 301
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 301
```

-continued taggtttgga tttgcggac                                                   19

<210> SEQ ID NO 302
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 302
ggcgctagga tgaaggttc                                                   19

<210> SEQ ID NO 303
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 303
gtggcgctag gatgaaggt                                                   19

<210> SEQ ID NO 304
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 304
gtgtggcgct aggatgaag                                                   19

<210> SEQ ID NO 305
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 305
taggtgtggc gctaggatg                                                   19

<210> SEQ ID NO 306
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 306
ggttaggtgt ggcgctagg                                                   19

<210> SEQ ID NO 307
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 307
ttaggtggtt aggctcagg                                                   19

<210> SEQ ID NO 308
<211> LENGTH: 19
<212> TYPE: DNA
<213> ORGANISM: Artificial Sequence -continued
<220> FEATURE:
<223> OTHER INFORMATION: Antisense oligonucleotide

<400> SEQUENCE: 308
gttaggtggt taggctcag                                                                                      19

<210> SEQ ID NO 309
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 309
cgagtatctt acgtgtcag                                                                                      19

<210> SEQ ID NO 310
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 310
attatcgagt atcttacgt                                                                                      19

<210> SEQ ID NO 311
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 311
atggtttgaa ttatcgagt                                                                                      19

<210> SEQ ID NO 312
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 312
cttgtcggat gatgcca                                                                                        17

<210> SEQ ID NO 313
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 313
gatggcgttc ttccagg                                                                                        17

<210> SEQ ID NO 314
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 314
ccgttgagag ctggtgca                                                                                       18

<210> SEQ ID NO 315
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 315
ccttgtcgga tgatgcca                                                       18

<210> SEQ ID NO 316
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 316
gatggcgttc ttccaggt                                                       18

<210> SEQ ID NO 317
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 317
ccgttgagag ctggtgcat                                                      19

<210> SEQ ID NO 318
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 318
cttgtcggat gatgccac                                                       18

<210> SEQ ID NO 319
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 319
cgttgagagc tggtgcatg                                                      19

<210> SEQ ID NO 320
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 320
tcggatgatg ccacagatg                                                      19

<210> SEQ ID NO 321
<211> LENGTH: 19
<212> TYPE: DNA
<213> ORGANISM: Artificial Sequence
<220> FEATURE:
<223> OTHER INFORMATION: Antisense oligonucleotide -continued

<400> SEQUENCE: 321
gatggcgttc ttccaggtg                                          19

<210> SEQ ID NO 322
<211> LENGTH: 19
<212> TYPE: DNA
<213> ORGANISM: Artificial Sequence
<220> FEATURE:
<223> OTHER INFORMATION: antisense oligonucleotide

<400> SEQUENCE: 322
tcgagtatct tacgtgtca                                          19

<210> SEQ ID NO 323
<211> LENGTH: 18
<212> TYPE: DNA
<213> ORGANISM: Artificial Sequence
<220> FEATURE:
<223> OTHER INFORMATION: control oligonucleotide

<400> SEQUENCE: 323
cgtttaggct atgtactt                                           18

<210> SEQ ID NO 324
<211> LENGTH: 3832
<212> TYPE: DNA
<213> ORGANISM: Mus musculus

<400> SEQUENCE: 324
agtttcccac aagccaggct gatcccctc tagcagtcca cttcaccaag gtgagcgagt     60
gtccctgctc tccccacca gacacagctc tgctggcgaa agtggcagag aggtattgag    120
ggtgggtgtc aggagcccac cagtacagct ggaaacaccc agccactcca gacagaagaa    180
agcttagaga agacagaccc atgctgtggc cctgagctct gcagtactga attcagctct    240
cccggcaact tctcctgact ctgccttcag acgagacttg gaagacagtc acatctcagc    300
agctcctctg ccgttatcca gcctgcctct gacaagaacc caatgcccaa ccctaggcca    360
gccaagccta tggctccttc cttggccctt ggcccatccc caggagtctt gccaagctgg    420
aagactgcac ccaagggctc agaacttcta gggaccaggg gctctggggg acccttccaa    480
ggtcgggacc tgcgaagtgg ggcccacacc tcttcttcct tgaaccccct gccaccatcc    540
cagctgcagc tgcctacagt gcccctagtc atggtggcac cgtctggggc ccgactaggt    600
ccctcacccc acctacaggc ccttctccag gacagaccac acttcatgca tcagctctcc    660
actgtggatg cccatgccca gaccctgtg ctccaagtgc gtccactgga caacccagcc    720
atgatcagcc tcccaccacc ttctgctgcc actggggtct tctccctcaa ggcccggcct    780
ggcctgccac ctgggatcaa tgtggccagt ctggaatggg tgtccaggga gccagctcta    840
ctctgcacct tccacgcctc gggtacaccc aggaaagaca gcaaccttt ggctgcaccc    900 caaggatcct acccactgct ggcaaatgga gtctgcaagt ggcctggttg tgagaaggtc    960
ttcgaggagc cagaagagtt tctcaagcac tgccaagcag atcatctcct ggatgagaaa   1020
ggcaaggccc agtgcctcct ccagagagaa gtggtgcagt ctctggagca gcagctggag   1080
ctggaaaagg agaagctggg agctatgcag gcccacctgg ctgggaagat ggcgctggcc   1140
aaggctccat ctgtggcctc aatggacaag agctcttgct gcatcgtagc caccagtact   1200
cagggcagtg tgctcccggc ctggtctgct cctcgggagg ctccagacgg cggcctgttt   1260

-continued

```
gcagtgcgga ggcacctctg gggaagccat ggcaatagtt ccttcccaga gttcttccac    1320
aacatggact acttcaagta ccacaatatg cgaccccctt tcacctatgc caccccttatc   1380 cgatgggcca tcctggaagc cccggagagg cagaggacac tcaatgaaat ctaccattgg    1440
tttactcgca tgttcgccta cttcagaaac caccccgcca cctggaagaa tgccatccgc    1500
cacaacctga gcctgcacaa gtgctttgtg cgagtggaga gcgagaaggg agcagtgtgg    1560
accgtagatg aatttgagtt tcgcaagaag aggagccaac gccccaacaa gtgctccaat    1620 ccctgcccctt gacctcaaaa ccaagaaaag gtgggcgggg gaggggggcca aaaccatgag   1680 actgaggctg tgggggcaag gaggcaagtc ctacgtgtac ctatggaaac cgggcgatga    1740
tgtgcctgct atcagggcct ctgctcccta tctagctgcc ctcctagatc atatcatctg     1800
ccttacagct gagaggggtg ccaatcccag cctagcccct agttccaacc tagccccaag    1860
atgaactttc cagtcaaaga gccctcacaa ccagctatac atatctgcct tggccactgc     1920
caagcagaaa gatgacagac accatcctaa tatttactca acccaaaccc taaaacatga     1980
agagcctgcc ttggtacatt cgtgaacttt caaagttagt catgcagtca cacatgactg      2040
cagtcctact gactcacacc ccaaagcact cacccacaac atctggaacc acgggcacta      2100
tcacacatag gtgtatatac agacccttac acagcaacag cactggaacc ttcacaatta      2160
catcccccca aaccacacag gcataactga tcatacgcag cctcaagcaa tgcccaaaat      2220
acaagtcaga cacagcttgt cagaacacgc tcgtgtgcac gtacacacat gcagccctc       2280 cactctatct cctgagttcc atgaatacac accgactctc caagatgtac cccacgtctc      2340
acttgccact gaccccagtt ccctacccac aagccccaat ccatgcctaa gcgtggccca      2400
cagaagaact tctcttttat ttgggatcca aggcccctgg ccccagtgc ccatccaata       2460 aactgtggtc agctggacaa tcaccctgat cagatatggg aacatataag cagacagctg      2520
ggtttaagat cccagcagga gaaagcggat accaaatgaa agagagtgct agaacaggtg      2580
cctcagcact gtctccagca cccccaaattc ctgcctgtgg ttaggagaca tccatcaggg     2640
ctctaggcct ctcggacccg gcccaagagg ccagcattct cctggcgaag ggctcggtag       2700
tcctcacaga tcttctccag gttgctcaaa gtcttcttgc ccatctctgt ctcaatctaa        2760
gaaaacagga tgcacacttc ttcagcccct gcaggctgcc cctctactga actcctccct          2820
gctcctccta ttcccgtaac agcagcctgt tccttcccat cactgggctt ctgggtatgt          2880
ccttccctcc actccaccta aagcagcaac ttctgccatg ggctctggga ggcattagga         2940
gccgcaagct aaaagccagg gctcagagta ggctactggc tagcttcagg tcccaggcac          3000
agtgggcacg aaggcaaagc ctctagctgt tagttgtctg gtttcaaaga ctctcagcgc          3060
aaaacaagga actatcccct ggcctgtctc cattcccctt accagtccca ggtctcacct           3120
gctcctcaag atctcgaact tccctcatga tagtgcctgt gtcctcaatg gtctggatga            3180
gctgactgca attctggaga cagcaagaat acaaggcttg cacctatgct ggccctctcc           3240
agccaaccca ccaggcacat ggctcccctc acctcatgca gggcagctag gtacttgtag            3300
gctttccgaa cagcatcatc cttcttagca tcctgataag acaaagggga tctccgagat            3360
atcagcaagc cattcccccct tttccactac tctatgcccc tataagacca cccttttacta         3420 gtactttgcc ttcatcctcc acagagcaaa gctaggcccc aagcaacagt gcacctaaag            3480
gactcacaga ggggcaggca acaactcagt cccgcctcca ccctcccgga ggccagcctg            3540
ctccatacct tgaacacaag ctcatcagtc actgcaaatg tccggtcgag cttcccagag            3600
agagagttga tttccttctg cagttccttt gtgtccgaca agatctggta gaaaccaggg            3660
```

-continued

```
taactatcag tgcacatctt gggcaaggta gctgatcagt gataacactc acgtgcctat     3720
acttacatcc agtcagggcc catgtcgctg tgttggggtg actattatgt gttggagtgt     3780
gcctgaacag ctctgcctag tagtgagcat aaagtccctg tgtgatcacc cc              3832

<210> SEQ ID NO 325
<211> LENGTH: 18751
<212> TYPE: DNA
<213> ORGANISM: Mus musculus

<400> SEQUENCE: 325
gcagctgcca gatcttgaat acaaacctta aaacctcaca aacatcaagt tccagaggag       60
tctccaagtc ctagaacttc tatgacactg ttggcttcag gaaaactggt cacttcagag      120
cccaatgcta aggacccata tttcccaaaa ttgtgatctt aagcaagctg cacctccatt      180
ttgcccatcg gtctaaaaac aatacagcca tgatgagatg gacctcagag ggtgagaagt      240
gtttggctct gtctggaatg tagaaaattc tagttaaatg ttggctacca aaattatgac      300
agctgtttag aatcctaaac ctttgcaaac gggagtgttt ctttcctttt gtttgtggtt      360
ttggtttttt gttttttgttt ttttgtgttt tttgtttttt tcttttttctt tttacacgga      420 atctggctat atagccccaa gcaaccttaa actcttgatt cttctgcctc agtttctggg      480
gtgctgggat tactggtatg tgatactgga tgaaactgga acttttcaga gtagactgtt      540
acaaagttta gaatcatcag gctatggcta tattgttcct gacaggacta ggaccctggg      600
ccgctatgtg tatggttttt ttgtttgttt gttttaacaa cccagagcct tgtgcgtgtt      660
aaacaagcac tctggcactg agctgcaatg gccagccttt cttcccttg cccttcttgg      720 tgatgctggc tgcattaaca gccactgggg ctgttcccag gtgggtggct gctgggtcag      780
ggcactcagc acaaacatga tgtggggctc actcagagac tcgcagcagc ttctgggagc      840
cagccattct gagactctct gattctgtga atttgtgggg ggagtacagc ccactttttt      900
ctccatgaat tgctttccat gcctcttgcc ttctgtggaa agaaaggcta caggagtggc      960
cagctctgcc aagccttggc aacatgatgg tggtgatcat atgcatgctt gctaaggaaa     1020
tactgaggtt tggagcagaa ggaagcctct ggagacagag cactacccca cctctcccct     1080
ggctgcttcc cattcacatg gcaggcttca gatcccttct tctgttcaac ccagcgatcc     1140
tccaacgtct cacaaacaca atgctgtctc tacctgcctc gggatgcctt tgtgatttga     1200 cttatttcc ctcagttttt ttttctgac tctacacact tttgtttaag aaattgtggt       1260
ttctcatgag ccctgttatc tcattgatac ctttaccc tgtggtgagg ggaagaaatc      1320 atatttcag atgacttgta aagggcaaag aaaaaccca aaatttcaaa atttccgttt       1380
aagtctcata agaaaagaat aaacaaagta agagagcaaa gaaaaaaaaa ctacaagaac     1440 cccccccca ccctgcaatt atcagcacac acactcatca aaaaaaaatt ggattattag      1500
aagagcgagg tctgcggctt ccacgccgtg gttttcttc tcggtataaa agcaaagttg      1560
tttttgataa tgtggcagtt tcccacaagc caggctgatc ccctctagc agtccacttc      1620 accaaggtga gcgagtgtcc ctgctctccc ccaccagaca cagctctgct ggcgaaagtg     1680
gcagagaggt attgagggtg ggtgtcagga gcccaccagt acagctggaa acacccagcc     1740
actccaggta aggactttgg aaactaatac cattcatcct aaatgccaga taggtggagc     1800
agttggtcct tagacagggg caaaaagaag tactttgatt gtttgatgca cagataaaca     1860
ggattttttt ttaacatatg tctatcaact gctggtctcc aggaatgccg gagctttagg     1920
```

-continued

```
caactcaaga tgctgtccag ctataactag aaactagaag tgcatctctt gtttcttttc    1980
ctcctgctgt cttccatttc ttctcctgtc tccccctgct tctttgcctg tctctgcctt    2040
ccatcagtgc ccagtctctg tctctttccc aggctctgac tatatgcctg tctgtctctt    2100
ccagcctggc cagccacagt cccttttcttt cctcccgctc tctgactctc ggctcatctt    2160
ccttcagctg cttttgcacc cggtattgag cgcagatatt tgtacacaac tggcgcttaa    2220
taataatggc ttaagagctc tgtttttccaa aacgggcat tagttctgtg tgtcttaggt     2280
ttgtgagctg tcaggtcagt cttagcattt aactgacctt ctgcttgtgt cacgcaagat    2340
aacaccctca gtcagccaca gtttagcaaa ggactatatg actgtgagca gaatccatgt    2400
gcaaggagag caggcagttc aggacgaggg tgagctggtc tctgcaggtt tagtgctgtg    2460
gcactgtgcc tggtatatgg tgagttctca ctgtttgcta ttagcatttt taaacaaatt    2520
agaatcgtgc tatagattgg attttgtttct gctctgttca agcgatacca ttttttgtagc    2580 atactaaaat aacgaacacg tgatctttta tgtctgccgt gactgtcctc acatcaccat    2640
gaatttgatt acctgaatta agtgctgatg gtgggatatt tgggtttctt ctgattctaa    2700
aactccatac ctgactccat ggatcctgaa aatggagtag ctggggaaga aggggtgtac    2760
atcttaaggg gttttgccct ctctacaaat tgcttttcca aaacgttgtc ttattttctg    2820
ttgtttctat tcaagttaat tttaggtgtg tgttaccatt tttaatcctt ccccatcata    2880
agaaaaatga caagtattaa aattttgcat tttggttact tttaatgacc actgaccatt    2940
tgtgctctgt aggctagagt tttatgatca cattcttcat cctactaaat tgctcatgat    3000
ttttcaaaat tgctaatagc tcttaattta gaaaggataa taactattgg ctatatgtat    3060
atgacacata tttccctgaa attcatcatt tgtgtgtatg tgtattttaa ttgtattcat    3120
ttacttagtt tatgagcatg catgttcttc ctgcatgtgc accatatgtg tgcctggtgc    3180
ccacagaggc cagaagatgg tgtgggatct catgggactg gagttacaga tggttacgtg    3240
ggtgctggcg cttatgtggc ttcttttctat ggttttgtgt ttaaaagcct tttaccactt    3300
gaaaatgaga agctacctcc tctacaagag cagcagtgct cttacccatg gagccatctc    3360
tccagcccta tttgtatggg ggggggggt cttctgagac aaggtctcac tctatagccc    3420
tgactggcct aaaactcact gtatagacca ggctgacctc aaactcacaa agacccatcc    3480
atctgcctct gccttctgag aagtgggata gaagacatac accaccacgg cgggcaatca    3540
cttgcttttt ttccctatttt attgtgcttt gtaatgcatg tgtctttag gtctttagat    3600 tactcttttc ttgtggggct tctgtgtatg gttttgtgtt ttaagtcttt tgcacttgaa    3660
aatgagataa ctgttcaccc catgttggct tccagtctcc tttatggctt catttttttcc    3720 atttactgca gaggtcaaaa gtgtgggtat gggagccaga ctgtctggaa caacctagcc    3780
tcaactcaag tcatctgtgt gaattttacc caggctctta acctctctgt acctccattt    3840
cctcgtatgt actgtgatga ttataacagt acctacctca gaggatcttt ctgaggatta    3900
tttttattaa tgatggtagg tgctcagcac aaggccaaac aacaatgata gacattaaaa    3960
cgtatctctc tagtgggtct ggaaattatt ctagagcgtc tgatgacagc gacatttcaa    4020
gtgggcaggg aggtattggt gggaaagtgg gctatctacc cagtcacttt attttcccct    4080
aattgtctca gaatcatttg ttaatctgtc ctgcactgtt cctcatgttg aaatgttgtg    4140
ttcatcacaa attccattcc ctctgtgcat gggtctctgc cacggttttc tactctaatc    4200
tgctccttag tgtttattct tgtacaaagc ccacactatt tttctgatgt tgctttgcaa    4260
aacaattcaa taccagccat gggtgtctct ggcacctagc agcatcagtc ctccagccag    4320
```

-continued

```
aggccagtga ttattttcag tcctttctct cactccctct ctctctgtct ctgcatgtct    4380
gtctgtctgt atatgtctct gtcttgttca ttctttctct gtcactttc ctctaaactg      4440 ctctcactgt ctctctctat gagcttgatt cctattccat ctcatgtttc tctctatata    4500
tttctctatc tgtatctctt ctatatctgt attcacacac atatgatata tatatatata    4560
tctcaatata tatatatata tatatatata tatatatata tatatatata tatatatcaa    4620
tatatatatc tcataccata ccatacatac atacggctat atagctccat aagatttacc    4680
ccagccacga gacagaaaga tgctggcctt cctccacctc gtactcttcc ctccccagtc    4740
tagaagggca aactgggctc agagatgagc agcccccacc cccaggcctc acagagatgt    4800
tgtgtcagag ttaaatccaa gagcagatct cagaattctc agtgggacct tgactttggc    4860
aattccacat tgcaggcctt agtttacctc tcaggaccca ggaggccatt aacaggagac    4920
ctgaggtgcc cttccctctt ctacatcctc atgagttgga tccagtccat aaccatagca    4980
tggggccaaa tctcacaagc tctggtctat gtgaggttct gggcccccatg agtcagaagt   5040 cctagcggac caaagaacac tagtaacgat ggagaaatat cagttaagta tgaaccctca    5100
gagttcatac tgcattcctt gggacaacca ttctgggggcc cttccaaaaa gcctggtggt    5160
gtgctctttc catgagggcc aggccaaatg tcttcttcct cttgtccctg tatctggaag    5220
aatgttataa tttgggggaaa gttgtcccag gagagcgggt ctggagccat atgtaagtga   5280
ccatttatca gtcatagaca cttgctcagc attctgtatg tacgaacttt gcaagatggc    5340
tcctgttact gtcccaaatt agacaggagg acagaaagac cccagccttc ctccatcaca    5400
tactcttccc agtctagaag ggcaaactgg gctcagagat ggacaggaag gccccttgt     5460 cccaagaggg caaagcctga ccccagatca ggacagtaga gggttttcca atcctctgtc    5520
ataatggagc tcaggaggga gggaggctga cattccagag ccagcaagag gccttatgga    5580
gttttaagct tcctggcttt aggtggttcc catttctttg ggctctggga catcaataca    5640
cacagtaaga aggtggatcc atgcacccta cagagtctgt gttcttgaga ttctaaaatc    5700
cgttggcttt gagaaatgat atcgtacagt tctgagtttc tgttactaca gcatttgaag    5760
actcaagggg gtctcaatat ccatgaggcc tgcctaatac tcaccaagca tccaaccttg    5820
ggcccctctg gcatccaaga aagacagaat cgatagaact tgggttttgc atggtagcca    5880 gatgacgtc acctaccaca tccgctagca cccacatcac cctacctggg cctatccggc     5940
tacaggatag actagccact tctcggaacg aaacctgtgg ggtagattat ctgcccccctt    6000 ctcttcctcc ttgttgccga tgaagcccaa tgcatccggc cgccatgacg tcaatggcag    6060
aaaaatctgg ccaagttcag gttgtgacaa cagggcccag atgtagaccc cgataggaaa    6120
acatattcta tgtcccagaa acaacctcca tacagcttct aagaaacagt caaacaggaa    6180
cgccccaaca gacagtgcag gaagctggct ggccagccca gccctccagg tccctagtac    6240
cactagacag accatatcca attcaggtcc tctttctgag aatgtactga tgcatcacac    6300
agtcacacca gttccacaag tatttaagga ggagatttct tataagttct gaccaaacat    6360
aaagagcact tcaaaagtga ccatggtcca gccatatggg ttaagccaat atagtggaaa    6420
attctactca ccaaacctga tccgcatttg cttgagctac tgtaatgaag tatcacaaac    6480
tgggggactt acatagcata gaattatcat gttagcgttc tggaggctat aagaccaaga    6540
tgaagacgtc agcagggttg attcctcctg taagtcctgg cctccttctc atctctgatg    6600
ctttcctttg ctgttctttc ttggaggagc atcacctcat ggctgcctgc ctgcagtctt    6660
```

-continued

```
tcagctcatc gcatcacggt tctaggaagc cagtctcagc ttccacagac ccagactcct   6720
cttttcatgc taatgtttta gcccgtgaca cactagtctt aatacctagg ttctcatata   6780
aatctctcaa ctctgataag ccccagacat gatagcaaag aagatgcaat tgccttccaa   6840
aacccttccg tgcttccccc aggctgttct cagaagctac atgcccaaca catgtagtat   6900
atagtagaac ggagaatgac atattcacat gcacacacaa acacagcagg gaaaatgtac   6960
atatatatac ttcctagaga aaaatgaggc agtatcagcc tgaaatggtg gtttataatc   7020
ccagtactca gaatgcagaa acaaggagtt caaggacagc ctgggtatat aaggagttcc   7080
agactacaag aaaccctatc taaaaagaaa aggaggtccc aggccatgag aagactatag   7140
aattctgaac ctggctatcc tcttaattaa aatcagggta gaattctata gtcagttcaa   7200
gatctggttc cctctctgac tggaagtata ggatcctgaa aaacgaaagc cacactttta   7260
agggactgta aggtagtgag gctcagcaca gggacctggg tcaccatgta gagctttgaa   7320
gaggaaatca gaagactgca gtatggctaa gggaagaagt ggacttccaa gcttggcaga   7380
gattggagct agtttgagga gcgcccaggg accctcaatc aagcaaccct atccctcttt   7440
ttttcctggc acctgccacg ccaattccaa gacagaagaa agcttagaga agacagaccc   7500
atgctgtggc cctgagctct gcagtactga attcagctgc aagtcttccc tgcctctact   7560
gcttaccttt gcatttagcc acatctgact atcactgtat actctgctcc tccatcctct   7620
accctccatc tccagtaatg ctcctgttgt agctgcttct gccaaaaacc tagacatcat   7680
cttgaccctt tctctcatct cctccatcca agctcccggc aacttctcct gactctgcct   7740
tcagacgaga cttggaagac agtcacatct cagcagctcc tctgccgtta tccaggttgg   7800
tagcagcaac accactcgcc tcactattgc agtacacttc ccactagcac agttccctgg   7860
agccttcctg ctcacagcat ccaactgaat cttgtgaggc tatgcccaag tcattggaat   7920
aaaaagatga gaagagagtc caagacaagc cccagtagaa tcagcaaaga ctatgtggcc   7980
tgcacagagt gcagggggta ctggagggtc ccacaaacca actccccatc accccacatt   8040
cacgacagag tggtatggtg tatgtaagca agtgaggtgc tggacatgtg catgtgtaga   8100
atatatccat caatctgtgt tcctgctgtc agggtagcat atatgtatgt aagacagacc   8160
agaggtgtag ttatgaggct atcttgcacc acccctggaa tgcatgtgac tccattccac   8220
tgttatccct gcagcctgcc tctgacaaga acccaatgcc caaccctagg ccagccaagc   8280
ctatggctcc ttccttggcc cttggcccat ccccaggagt cttgccaagc tggaagactg   8340
cacccaaggg ctcagaactt ctagggacca ggggctctgg gggacccttc caaggtcggg   8400
acctgcgaag tggggcccac acctcttctt ccttgaaccc cctgccacca tcccagctgc   8460
aggtgaggcc cggggcccag aatggggtaa gcagggtggg gtacttgggc ctataggtgt   8520
cgacctttac tgtggcatgt ggcggggggg gggggggggg ctggggcaca ggaagtggtt   8580
tatgggtccc aggcaagtct gacttatgca gatattgcag ggccaagaaa atccccactc   8640
tccaggcttc agagattcaa ggctttcccc acccctccca atcctcatcc cgataggaga   8700
ccttatgatt ccatggacat agccatgtat cctcatccca ctgtgacgag atggctgggg   8760
cccaagaagg taacagtgtt ggggccagct ctaccccttg aaactgttgg accttgatac   8820
attcactctc cacgagcctc agattccact gatgtgaact ggatagttcc attgttgcta   8880
ccgtgtgaga ctttagtaaa gagctaatga atgagacaca gaactattaa gatgaggctc   8940
atggcatctc atggcatctc ccttctctct ccagctgcct acagtgcccc tagtgtcatggt  9000 ggcaccgtct ggggcccgac taggtccctc accccaccta caggcccttc tccaggacag   9060
```

-continued

```
accacacttc atgcatcagg tatggaatcg gagcaggctg ggaggaggga acaaagagga    9120
cagctgtgga gcagagcccc aagccccgct gagccatggt ccatgtgttc cccagctctc    9180
cactgtggat gcccatgccc agacccctgt gctccaagtg cgtccactgg acaacccagc    9240
catgatcagc ctcccaccac cttctgctgc cactgggggtc ttctccctca aggcccggcc    9300
tggcctgcca cctggtaaca ccttcacagt atctccaagt tctctaatct ttgagcatgt    9360
gcaatgtaaa cttttctgaa ttatagccct atggaggtat agaagggtct taagagtcac    9420
ggaaactcca acctccaaaa aaaaaaatat cagacttaga accttgaaga catagaatgc    9480
aaaaaaaacc acaaatcgct attatcagtc aaaatgccat cacttaccaa tgggcatctt    9540
taggctgtta tgtcagaagc ccttgactgt gggaacagca gagtactatg agacagagtc    9600
ttcaaggctc aggaagggga ggggcctttct ggaacaagct gtagagtcta acctgcagct    9660
ccagaagtac cctgtctcta cccacaggga tcaatgtggc cagtctggaa tgggtgtcca    9720
gggagccagc tctactctgc accttcccac gctcgggtac acccaggaaa gacaggtgag    9780
ttggcagggc tggcaagaaa cggcccctgc ccacacctca ccccacccct gcacctattc    9840
ctctgctgac atcccatatt ctcccatccc cagcaacctt ttggctgcac cccaaggatc    9900
ctacccactg ctggcaaatg gagtctgcaa gtggcctggt tgtgagaagg tcttcgagga    9960
gccagaagag tttctcaagt gagtagcctg accctaccca cagagttctg ctgtctaggc    10020
ttcacgtctc aactcaccat cctctcaatg gatgataata agaatcataa agattcagac    10080
tccatccctc cctggctctg tgatcttggg caagttatgg gtctctaggc ccagtttacc    10140
tcgcatgtat gaagagacat aataataaag gtatgtgctc atagttacct tcctgttaca    10200
cgcagaagga tctaaggcca cagagaatta agggtcaatc aagctcacac aggacctaag    10260
tgatgaatct tgaatatgaa cacaggcagc caggttccag agcccacacg cctaactgct    10320
ttgtcccgct tcccctcaca caaaacacat tcctgatcct ccaatttctg ttcctctaga    10380
tgactataga gctcttgcct ctctgctctc tatctgctgt ccctcccctt ctgtatcttg    10440
ctagtcaccc ctaacttttg gcaatggtgc gtgtttgcgt ggccaggcct ttgcatgggc    10500
tgtgcctgac acctgaaatg ccataccccct gcatacctcc tgtctaacgt catcccagca    10560
ttttggccag actcaaaggg taaataagct caggcctggc agcccagagt tgctgaagca    10620
catgtgttta aggcaagcaa gggggtgggg ggggagcac tgagcataga gaaatctccc    10680
aaagggtcta ggccgtccct aactgataca ctaagccaag aggcctgacc caccatggtc    10740
agctacatgg aatcttctcc ttactcaggc actgccaagc agatcatctc ctggatgaga    10800
aaggcaaggc ccagtgcctc ctccagagag aagtggtgca gtctctggag cagcaggtaa    10860
tgcctgcagg gtgtggctgc ggggtgtggc tgcgggaaa aaggatggga gggaggaccc    10920
tgtgagggaa ggcatgggca aaagtgtgcc tgagaacgac caggtggaag ccccactttg    10980
gtgtacatcc ccacagctgg agctggaaaa ggagaagctg ggagctatgc aggcccacct    11040
ggctgggaag atggcgctgg ccaaggctcc atctgtggtg agtaccccaa gtccagaggc    11100
agcagacttc aactgctgag gggcaagaca ggagcccata aggaccaaat gtcttcttct    11160
cacatgcaag ccctgccctg tacagaccat tcccacctaa ttaatatgcc agatccaaag    11220
acacgcctac tctgcttaca aaccttctga cctccaaaac attatgattc tgccttttca    11280
gggcacatac agaaggcagt gaactcacag ggccactgca aaaaggaaa atggagggcc    11340 ttatgttcaa atttcaagat aagctcagaa catcgaacag tgtgtgacca cacatttcac    11400
```

-continued

```
atacccagtc tcaggctgat atgagtctta tactataaca gaggtagcta ccaccatcat   11460
cctaatgcac aaatgaggac aacttaggtc aggaagattt agttgatgct cccaggttca   11520
cagttggtgc taggggattc caattctgcc cctgctcacc ccagccctag catctatggc   11580
ttcatcgcat gctcatgcct gtactctaag atgctgcttt acagagctcc accagagcct   11640
gcaattgact atagggtggt gcccttctca aaagcattga ccttactgga cacagtggca   11700
tgcacctgta gtcctggcta ctggagaggc tgaaggagga gcacttgaac cctcaagttc   11760
aaaaccagcc tggtcaacac agagacaccc tgactcttct aaaacacaaa gaaacacggt   11820
tggggagaaa cttgagaggg aaaagtgatt gccatacaag gataaggacc tgagttttgc   11880
tgggtggtgg tggcggcggc gcatgccttt gatcccagca cttgggaggc agaggcaggt   11940
ggatctctgt gagttggaag ccagcctggt ctataaagct agttccagaa cagccagagc   12000
tacacggaga aaccctgtct tgaacacctc tgacagaaaa aggacctgag tttagatgcc   12060
agcacccaca ccagatgcag cactgtaaat ctgtaatccc agcatgtgta cacacaccac   12120
acatacaaat cagatagaaa tatgaccaaa tcaggaaatg caaattgtaa aataaagtgg   12180
ggttggggaa ctggacagat agctcaggga ttaagagagc ttgctgctct ttcaggggac   12240
cagagtttgg ttcccagcac cctcagagcc gctcacagct atctctaact ccagttccag   12300
tggatccaat gcacttttct gccttccaca ggtaccaggc acacatgcga tgcccagaca   12360
tgcatgcagg caaaactccc gtatacctaa aataaaatgc aagctgactt ggcagtaatc   12420
tcagcccatc ctgtgctaca tagtacatgt tagactagcc tgtactacat gctacatagt   12480
acatgttaga ctagcctgta ctacatgcta catagtacat gttagactag cctgtactac   12540
agagcaagag cccacctaca taaatatcca accaagcaag caatcatttt ttaaagtaaa   12600
atggaagact cagtgtggtg gcgcacgcac gcctttaatc ctagaactcg ggaggcagat   12660
gcaggcagat ctctgtgagt tcgaagccag tctggtctac agagcctggt ctatacactg   12720
agctccagga cagccaagac tacacagaga aaccctgtct ggaagaaaaa aaaaatatat   12780 atatatat atatatat acataaaata aaaagtggaa gccagatgtg gtggcacaca   12840
cttataatcc tagcactcca gaggtagaac taggctagaa ggtgcaaggc caactagaga   12900
tatatagtga gactgtctca gacaaaacga aaatgaatag gcaaacactc aggaggcaga   12960
ggaagtgcat ctctgagagc tgcaggccag tcagggctac atagtaagac cctgtcaata   13020
ataataataa tggcaataat aattttaaga ccaaaataaa tagacatgga tgaaggggga   13080
aaggaatgag aagaaggaag ataagcgatg agggaggaga tagggtgaaa gtggtctgta   13140
tgtattacat acatgtacaa aattgtctaa aaacaagttt aactaataag aaaatacaaa   13200
ctaatgtttg aaaggctaca atgaaatgac aagcttaagt gtctcgatta ccacacccct   13260
cccaacccct caggcctcaa tggacaagag ctcttgctgc atcgtagcca ccagtactca   13320
gggcagtgtg ctcccggcct ggtctgctcc tcgggaggct ccagacggcg gcctgtttgc   13380
agtgcggagg cacctctggg gaagccatgg caatagttcc ttcccaggtc agtggagtcc   13440
acaccccagt gccaggggt acaaaggagc tcccccaccc ccctcacccc cactaagagc   13500
tgggaggaaa ctgcacctga gtttattagg cttagaagcc ctcaactgtt ataaatgcat   13560
agccttgggc cccgtgtttt gggggattgg agccaggcct gacctatttg gcatctgcta   13620
cttcattcag tcaccatgag ggaggagcct ggccaagtga gtccaaagag ccctctcttc   13680
cgtccccacc tccaggaagt caggtgcact caaccaagct aaccaaccct ctcccacctg   13740
tcaggcctgg gttgtgagtt taccagggac catagatatt tggtgtcagg ctggctatgc   13800
```

```
cacttgagct gcttacatgc ctttgatgta caaattactt gactcctttt taaagtgagg   13860
agagctattt ggcaggagta ctgcaaagaa gacacagctt acggcgggta ctcagtaaac   13920
agtactatgt gtgagcatag actgtccctc cccccttggt gctagtggta ggaattgaga   13980
ccttggattc ctgatgcaga caaaggtggg gtaggggggtg aggaggccaa aggctctgat   14040
ctatgccaac cttctgcaga gttcttccac aacatggact acttcaagta ccacaatatg   14100
cgaccccctt tcacctatgc cacccttatc cgatgggtaa gcagggcaat agaggcccag   14160
cagctggtgg gcggcagggg gggagttgtg gtggggagtg cttgcctcct acattgcacc   14220
aagagcagaa ttcacccatt aacaaacctc agctctgagg agcccccaaga tgtgatcctt   14280 cttgatagct tcacctcaga tctagccctc aacccaaaac tactgcaagc caggtcagtg   14340
caaagcaaac tgtaacacta caaactaccc tttcctttgt ccaccctatc tctaacatca   14400
cccttgacct catgcctcac cctattcttt ctccttcccc ttgacccaca attacaaagc   14460
tatcatagct cagagggccg agagtaggct gctccctcag ccacaaccct gaggaacatg   14520
ccccttattc cacctgactc caacttccag gccatcctgg aagccccgga gaggcagagg   14580
acactcaatg aaatctacca ttggtttact cgcatgttcg cctacttcag aaaccacccc   14640
gccacctgga aggtgagttc ctctgtacac actggcagct gggatggctc caaggatggt   14700
tagcctgggg ctagacatgt ggggaaggag caggtcagtc tcagactcag gatgactgtc   14760
aaccctgtcc ctgactgggg tcccggtccc ccttccacag aatgccatcc gccacaacct   14820
gagcctgcac aagtgctttg tgcgagtgga gagcgagaag ggagcagtgt ggaccgtaga   14880
tgaatttgag tttcgcaaga agaggagcca acgccccaac aagtgctcca atccctgccc   14940
ttgacctcaa aaccaagaaa aggtgggcgg gggaggggggc caaaaccatg agactgaggc   15000
tgtgggggca aggaggcaag tcctacgtgt acctatggaa accgggcgat gatgtgcctg   15060
ctatcagggc ctctgctccc tatctagctg ccctcctaga tcatatcatc tgccttacag   15120
ctgagagggg tgccaatccc agcctagccc ctagttccaa cctagcccca agatgaactt   15180
tccagtcaaa gagccctcac aaccagctat acatatctgc cttggccact gccaagcaga   15240
aagatgacag acaccatcct aatatttact caacccaaac cctaaaacat gaagagcctg   15300
ccttggtaca ttcgtgaact ttcaaagtta gtcatgcagt cacacatgac tgcagtccta   15360
ctgactcaca ccccaaagca ctcacccaca acatctggaa ccacgggcac tatcacacat   15420
aggtgtatat acagacccct acacagcaac agcactggaa ccttcacaat tacatccccc   15480
caaaccacac aggcataact gatcatacgc agcctcaagc aatgcccaaa atacaagtca   15540
gacacagctt gtcagaacac gctcgtgtgc acgtacacac atgcagcccc tccactctat   15600
ctcctgagtt ccatgaatac acaccgactc tccaagatgt accccacgtc tcacttgcca   15660
ctgaccccag ttccctaccc acaagcccca atccatgcct aagcgtggcc cacagaagaa   15720
cttctctttt atttgggatc caaggcccct ggccccagt gcccatccaa taaactgtgg   15780
tcagctggac aatcaccctg atcagatatg ggaacatata agcagacagc tgggtttaag   15840
atcccagcag gagaaagcgg ataccaaatg aaagagagtg ctagaacagg tgcctcagca   15900
ctgtctccag caccccaaat tcctgcctgt ggttaggaga catccatcag ggctctaggc   15960
ctctcggacc cggcccaaga ggccagcatt ctcctggcga agggctcggt agtcctcaca   16020
gatcttctcc aggttgctca aagtcttctt gcccatctct gtctcaatct aagaaaacag   16080
gatgcacact tcttcagccc ctgcaggctg ccccctctact gaactcctcc ctgctcctcc   16140
```

-continued

```
tattcccgta acagcagcct gttccttccc atcactgggc ttctgggtat gtccttccct  16200
ccactccacc taaagcagca acttctgcca tgggctctgg gaggcattag gagccgcaag  16260
ctaaaagcca gggctcagag taggctactg gctagcttca ggtcccaggc acagtgggca  16320
cgaaggcaaa gcctctagct gttagttgtc tggtttcaaa gactctcagc gcaaaacaag  16380
gaactatccc ctggcctgtc tccattcccc ttaccagtcc caggtctcac ctgctcctca  16440
agatctcgaa cttccctcat gatagtgcct gtgtcctcaa tggtctggat gagctgactg  16500
caattctgga gacagcaaga atacaaggct tgcacctatg ctggccctct ccagccaacc  16560
caccaggcac atggctcccc tcacctcatg cagggcagct aggtacttgt aggctttccg  16620
aacagcatca tccttcttag catcctgata agacaaaggg gatctccgag atatcagcaa  16680
gccattcccc cttttccact actctatgcc cctataagac cacccttac tagtactttg  16740 ccttcatcct ccacagagca aagctaggcc ccaagcaaca gtgcacctaa aggactcaca  16800
gaggggcagg caacaactca gtcccgcctc caccctcccg gaggccagcc tgctccatac  16860
cttgaacaca agctcatcag tcactgcaaa tgtccggtcg agcttccag agagagagtt  16920 gatttccttc tgcagttcct ttgtgtccga caagatctgg tagaaaccag ggtaactatc  16980
agtgcacatc ttgggcaagg tagctgatca gtgataacac tcacgtgcct atacttacat  17040
ccagtcaggg cccatgtcgc tgtgttgggg tgactattat gtgttggagt gtgcctgaac  17100
agctctgcct agtagtgagc ataaagtccc tgtgtgatca cccctatgct tgtctgccta  17160
catgagccat caatcagagc cacagtgaca tcataccta gtgatctctt ccttctgctt  17220
ccggatgttg cccacaatct ccaggatgcg ctgagtatag gccagccggg acacatcttt  17280
tggcagagtc tccagctctg acacctaggt gggaacatgg caggcgtgag cccaagccct  17340
ataccacaac caccccttaca acccagggcc ctaaagtagg ccttaccagc tgcttataga  17400
cctcctcctt ccggcgagcc tcctctgcag ctgctcgaac actgtggtgc agctcctgga  17460
tttctgccag ccgtcgagac gattccagct agcaggaacc cataggcaga aggcagtgag  17520
cagagctcag aaacagcccc ctccctcagc cccctcccta tctatcaggg cagtccatct  17580
acactcagcc cactgtgcca cttacctccc tacagtcctg gagtcttctg aggtggcggt  17640
actcagcaag aagtgggacc cggtgtttct cccactggct tgctagatgg atgagcctct  17700
gagcgctgct ctccaccaca agctggcagg agtcaaggat atgtcaagat gggctggatc  17760 catctacccca cccctctcag cccaacccca aaccccagcc cacctgcagt ttggcgaggt  17820
tggcagcccc atcaggcagc aattccaccg tcctgctctt caggcgcagg gcctgctcct  17880
gctcggccac actgagttca ctttgtcggc actcggtttc cacctggtac actcacagcc  17940
aagctcccag tcatacacac agcccacgat cccagtgagc ccattatggc cctggcccag  18000
ctcaagacct cagagaactc caaggcccct acctactaca ggctttggca tcttcagctc  18060
tgtactgaca gccagaggct ctgagaagcc ctgtaaggcc ctgcccctac acatcctcct  18120
tgatcccctg atgcccatag ctcctatgtt ccccctacaaa gcctgactga tgccagacct  18180
ataggcctat atagtctata tagacctata gtctagcaag ccatcaaccc tacatgtttc  18240
tttgcataag ttctccttag ccttcaacaa taccaaaggt ctctaggatg ctccataaac  18300
gattatggca tctatagatc tctagatgtc agatcatctc tcaaggcccc agttctgacc  18360
tggtccagcc caagtccctc tctaagcccc tcacctgcac aaggttgatt cccagggtct  18420
tcatgtcagc ttcaacctct tcaatgttgt ggttcacact cgccagctgc tcacgaaggg  18480
actctaactc ctgctcttga gctgcccgtg tgtcctgaga aacacacgcc agtctaggtg  18540
```
gagctaccaa gtccagaaga caggcaatag cccagctgac tctatgtgtg tgtctgtctg     18600
tctgtctgtc tgtctgtctt ggtctcctta cctgttcaag cctttgagag gtagctggta     18660
catctgccac ctgagctgcc tggacctggg gctcctatgg gtagaaaaag caacctgact     18720
atcacacaaa gttctatccc tcccaggcca g                                   18751

<210> SEQ ID NO 326
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 326
gtctcgtctg aaggcag                                                          17

<210> SEQ ID NO 327
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 327
ggataacggc agaggag                                                          17

<210> SEQ ID NO 328
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 328
tactggtggc tacgatg                                                          17

<210> SEQ ID NO 329
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 329
tactggtggc tacgat                                                           16

<210> SEQ ID NO 330
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 330
aaacaggccg ccgtct                                                           16

<210> SEQ ID NO 331
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 331

-continued

```
tgcaaacagg ccgccgt                                               17

<210> SEQ ID NO 332
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 332
cactgcaaac aggccgc                                               17

<210> SEQ ID NO 333
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 333
tcgcatattg tggtact                                               17

<210> SEQ ID NO 334
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 334
ggtcgcatat tgtggta                                               17

<210> SEQ ID NO 335
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 335
gatttcattg agtgtcc                                               17

<210> SEQ ID NO 336
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 336
gaacatgcga gtaaacc                                               17

<210> SEQ ID NO 337
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 337
aggcgaacat gcgagta                                               17

<210> SEQ ID NO 338
<211> LENGTH: 17
<212> TYPE: DNA
<213> ORGANISM: Artificial Sequence
```

-continued

```
<220> FEATURE:
<223> OTHER INFORMATION: antisense oligonucleotide

<400> SEQUENCE: 338
taggcgaaca tgcgagt                                                    17

<210> SEQ ID NO 339
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 339
gtaggcgaac atgcgag                                                    17

<210> SEQ ID NO 340
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 340
gtaggcgaac atgcga                                                     16

<210> SEQ ID NO 341
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 341
agtaggcgaa catgcga                                                    17

<210> SEQ ID NO 342
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 342
tcgctctcca ctcgcac                                                    17

<210> SEQ ID NO 343
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 343
tcatctacgg tccacac                                                    17

<210> SEQ ID NO 344
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 344
attcatctac ggtccac                                                    17
```

-continued

```
<210> SEQ ID NO 345
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 345
cgtaggactt gcctcct                                                          17

<210> SEQ ID NO 346
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 346
tacacgtagg acttgcc                                                          17

<210> SEQ ID NO 347
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 347
ataggtacac gtaggac                                                          17

<210> SEQ ID NO 348
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 348
tagcaggcac atcatcg                                                          17

<210> SEQ ID NO 349
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 349
ttcacgaatg taccaag                                                          17

<210> SEQ ID NO 350
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 350
gatcagttat gcctgtg                                                          17

<210> SEQ ID NO 351
<211> LENGTH: 17
<212> TYPE: DNA
<213> ORGANISM: Artificial Sequence
<220> FEATURE:
<223> OTHER INFORMATION: antisense oligonucleotide
```

<400> SEQUENCE: 351
cttgaggctg cgtatga                                        17

<210> SEQ ID NO 352
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 352
ttgcttgagg ctgcgta                                        17

<210> SEQ ID NO 353
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 353
attgcttgag gctgcgt                                        17

<210> SEQ ID NO 354
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 354
ttggagagtc ggtgtgt                                        17

<210> SEQ ID NO 355
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 355
tacatcttgg agagtcg                                        17

<210> SEQ ID NO 356
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 356
acgcttaggc atggatt                                        17

<210> SEQ ID NO 357
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 357
ttcatttggt atccgct                                        17

<210> SEQ ID NO 358

```
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 358
gtgaggacta ccgagcc                                                  17

<210> SEQ ID NO 359
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 359
atctgtgagg actaccg                                                  17

<210> SEQ ID NO 360
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 360
tgttttgcgc tgagagt                                                  17

<210> SEQ ID NO 361
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 361
ttcggaaagc ctacaag                                                  17

<210> SEQ ID NO 362
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 362
ctgttcggaa agcctac                                                  17

<210> SEQ ID NO 363
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 363
aaggatgatg ctgttcg                                                  17

<210> SEQ ID NO 364
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 364
```

-continued

```
ctcgaccgga catttgc                                          17

<210> SEQ ID NO 365
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 365
ctcgaccgga catttg                                           16

<210> SEQ ID NO 366
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 366
gctcgaccgg acattt                                           16

<210> SEQ ID NO 367
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 367
agctcgaccg gacattt                                          17

<210> SEQ ID NO 368
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 368
ggaagctcga ccggaca                                          17

<210> SEQ ID NO 369
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 369
atcttgtcgg acacaaa                                          17

<210> SEQ ID NO 370
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 370
agatcttgtc ggacaca                                          17

<210> SEQ ID NO 371
<211> LENGTH: 16
<212> TYPE: DNA
```

-continued

```
<213> ORGANISM: Artificial Sequence
<220> FEATURE:
<223> OTHER INFORMATION: antisense oligonucleotide

<400> SEQUENCE: 371
ccgtgatgcg atgagc                                                          16

<210> SEQ ID NO 372
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 372
ggagctatat agccgta                                                         17

<210> SEQ ID NO 373
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 373
tggtccgcta ggacttc                                                         17

<210> SEQ ID NO 374
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 374
catcgttact agtgttc                                                         17

<210> SEQ ID NO 375
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 375
tcttgcaaag ttcgtac                                                         17

<210> SEQ ID NO 376
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 376
ccaagttcta tcgattc                                                         17

<210> SEQ ID NO 377
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 377
agtctatcct gtagccg                                                         17
```

```
<210> SEQ ID NO 378
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 378
ccacaggttt cgttccg                                                   17

<210> SEQ ID NO 379
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 379
gtcatggcgg ccggatg                                                   17

<210> SEQ ID NO 380
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 380
actatattgg cttaacc                                                   17

<210> SEQ ID NO 381
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 381
ccgtgatgcg atgagct                                                   17

<210> SEQ ID NO 382
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 382
aagactagtg tgtcacg                                                   17

<210> SEQ ID NO 383
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 383
ccgttctact atatact                                                   17

<210> SEQ ID NO 384
<211> LENGTH: 17
<212> TYPE: DNA
<213> ORGANISM: Artificial Sequence
<220> FEATURE:
```

<223> OTHER INFORMATION: antisense oligonucleotide

<400> SEQUENCE: 384
atagtgaggc gagtggt                                                    17

<210> SEQ ID NO 385
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 385
taccactctg tcgtgaa                                                    17

<210> SEQ ID NO 386
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 386
cacacggtag caacaat                                                    17

<210> SEQ ID NO 387
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 387
tgctccgatt ccatacc                                                    17

<210> SEQ ID NO 388
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 388
ggttggagtt tccgtga                                                    17

<210> SEQ ID NO 389
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 389
gactgataat agcgatt                                                    17

<210> SEQ ID NO 390
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 390
tacatgcgag gtaaact                                                    17

-continued

```
<210> SEQ ID NO 391
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 391
ttagatcctt ctgcgtg                                                             17

<210> SEQ ID NO 392
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 392
ctggccacgc aaacacg                                                             17

<210> SEQ ID NO 393
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 393
acgttagaca ggaggta                                                             17

<210> SEQ ID NO 394
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 394
gtaagcagag taggcgt                                                             17

<210> SEQ ID NO 395
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 395
ggtaatcgag acactta                                                             17

<210> SEQ ID NO 396
<211> LENGTH: 18
<212> TYPE: DNA
<213> ORGANISM: Artificial Sequence
<220> FEATURE:
<223> OTHER INFORMATION: control oligonucleotide

<400> SEQUENCE: 396
cgtttaggct atgtactt                                                            18
```